(12) United States Patent
Charvat et al.

(10) Patent No.: US 8,716,494 B2
(45) Date of Patent: *May 6, 2014

(54) PYRROLIDINONE CARBOXAMIDE DERIVATIVES

(71) Applicant: ChemoCentryx, Inc., Mountain View, CA (US)

(72) Inventors: Trevor T. Charvat, San Jose, CA (US); Hiufung Chu, Millbrae, CA (US); Antoni Krasinski, San Jose, CA (US); Christopher W. Lange, El Cerrito, CA (US); Manmohan R. Leleti, Cupertino, CA (US); Jay P. Powers, Pacifica, CA (US); Sreenivas Punna, Sunnyvale, CA (US); Timothy J. Sullivan, San Carlos, CA (US); Solomon Ungashe, Fremont, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,921

(22) Filed: Oct. 5, 2012

(65) Prior Publication Data

US 2013/0237514 A1 Sep. 12, 2013

Related U.S. Application Data

(63) Continuation of application No. 12/887,416, filed on Sep. 21, 2010, now Pat. No. 8,293,925.

(60) Provisional application No. 61/329,046, filed on Apr. 28, 2010, provisional application No. 61/244,419, filed on Sep. 21, 2009.

(51) Int. Cl.
*C07D 207/04* (2006.01)
*A61K 31/40* (2006.01)

(52) U.S. Cl.
USPC .......................................... 548/537; 514/423

(58) Field of Classification Search
USPC .......................................... 548/537; 514/423
See application file for complete search history.

(56) References Cited

U.S. PATENT DOCUMENTS

| | | | |
|---|---|---|---|
| 6,093,737 A | 7/2000 | Anthony et al. | |
| 6,429,213 B1 | 8/2002 | Xue et al. | |
| 6,858,626 B2 | 2/2005 | Xue et al. | |
| 6,861,529 B2 | 3/2005 | Yohannes et al. | |
| 7,078,423 B2 | 7/2006 | Nivorozhkin et al. | |
| 7,087,631 B2 | 8/2006 | Nivorozhkin et al. | |
| 7,115,646 B2 | 10/2006 | Qiao | |
| 7,205,318 B2 | 4/2007 | Qiao et al. | |
| 7,244,730 B2 | 7/2007 | Suzuki et al. | |
| 7,294,624 B2 | 11/2007 | Duan et al. | |
| 7,563,786 B2 | 7/2009 | Priepke et al. | |
| 7,595,317 B2 | 9/2009 | Duan et al. | |
| 7,612,200 B2 | 11/2009 | Michelotti et al. | |
| 2005/0192292 A1 | 9/2005 | Isler et al. | |
| 2005/0245592 A1 | 11/2005 | Suzuki et al. | |
| 2009/0053192 A1 | 2/2009 | Millan et al. | |
| 2009/0093455 A1 | 4/2009 | Nagasawa et al. | |
| 2009/0105271 A1 | 4/2009 | Martinborough et al. | |
| 2009/0163545 A1 | 6/2009 | Goldfarb | |
| 2010/0075949 A1 | 3/2010 | Burdack et al. | |

FOREIGN PATENT DOCUMENTS

| | | |
|---|---|---|
| CN | 1610678 A | 4/2005 |
| WO | 03/059905 A1 | 7/2003 |
| WO | 03/068377 A1 | 8/2003 |
| WO | 2005/000793 A1 | 1/2005 |
| WO | 2005/037779 | 4/2005 |
| WO | 2008/029152 A2 | 3/2008 |
| WO | 2008/124085 A2 | 10/2008 |
| WO | 2008/157740 A2 | 12/2008 |
| WO | 2009/140549 A1 | 11/2009 |
| WO | 2010/033447 A2 | 3/2010 |

OTHER PUBLICATIONS

He, Xin et al., "Pyrrolidine Carboxamides as a Novel Class of Inhibitors of Enoyl Acyl Carrier Protein Reductase from *Mycobacterium tuberculosis*," J. Med. Chem. (2006) 49:6308-6323.
Ansorge et al., CAPLUS Abstract of WO2005037779.
Ashutosh et al., "CoMFA based de novo design of pyrrolidine carboxamides as inhibitors of enoyl acyl carrier protein reductase from *Mycobacterium tuberculosis*," J. Molecular Modeling, 2008, vol. 14(10), pp. 923-935 (retrieved on Caplus).
He, "Pyrrolidine Carboxamides as a Novel Class of Inhibitors if Enoyl Acyl Carrier Protein Reductase from *Mycobaterium tuberculosis*," J. Med. Chem, 2006, vol. 49, pp. 6308-6323.
Kadin "Synthesis and Antiinflammatory Properties of N-Substituted 4,5-Dioxopyrrolidine-3-carboxanilides," J. Med. Chem., 1976, vol. 19, pp. 172-173.
Kolobov et al., "Synthesis of 5-oxo-1-aryl-3-pyrrolidinecarboixylic acids and their derivatives," lzvestiya Vysshikh Uchebnykh Zavedenil, Khimiya I Khimicheskaya Teknologiya, 2006, vol. 49(3), (retrieved from Caplus).
Kubinyi "3D QSAR in Drug Design: Ligand-Protein Interactions and Molecular Similarity," vol. 2-3, Springer, 1998, 800 pp., TOC and pp. 243-244.
Lipp et al., CAPLUS Abstract of Chemische Berichte, 1958, 91, 2239-46.
Martensson et al., "Characterization of the human chemerin receptor-ChemR23/CMKLR1-as co-receptor for human and simian immunodeficiency virus infection, and identification of virus-binding receptor domains," Virology, 2006, vol. 355, pp. 6-17.
Simamura et al., Peptides, 2009, 30, p. 1529-1538.
Wermuth, The Practice of Medicinal Chemistry, 2d ed., 2003, 768 pages, Chapters 9-10.
International Search Report and Written Opinion, PCT application No. PCT/US2010/049718, Mailing Date Dec. 3, 2010, 8 pages.

*Primary Examiner* — Robert Havlin
(74) *Attorney, Agent, or Firm* — Kilpatrick Townsend & Stockton LLP; William B. Kezer

(57) ABSTRACT

Pyrrolidinone carboxamide compounds are provided that are useful for inhibiting the binding of ligands to the ChemR23 receptor.

25 Claims, 32 Drawing Sheets

PYRROLIDINONE CARBOXAMIDE DERIVATIVES

CROSS-REFERENCES TO RELATED APPLICATIONS

This application claims the benefit of U.S. Provisional Application Ser. Nos. 61/244,419, filed Sep. 21, 2009 and 61/329,046, filed Apr. 28, 2010, the disclosures of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is directed to novel compounds and pharmaceutical compositions that inhibit the binding of the chemoattractant peptide chemerin to the G-protein coupled receptor (GPCR) ChemR23. These compounds are useful in preventing inflammatory diseases including, but not limited to, psoriasis, dermatomyositis, systemic lupus erythematosus (SLE), arthritis, multiple sclerosis and conditions of metabolic syndrome including, but not limited to, obesity, insulin resistance, cardiovascular disease, and cholesterol transport and metabolism.

Plasmacytoid dendritic cells (pDC) represent a small (<0.5%) but versatile subset of circulating leukocytes functioning at the interface between adaptive and innate immunity. pDC are present in diverse tissue sites, often associated with general inflammation as well as lymphocyte infiltrates, and have been reported in reactive tonsils, inflamed nasal mucosa, thymus, cutaneous lesions (herpes zoster, skin blisters, psoriasis vulgaris, lupus erythematosus, contact dermatitis, but not atopic dermatitis, melanoma), peritoneal lavage fluid, and ovarian epithelial tumors.

ChemR23, also called CMKLR1, ChemerinR, and Dez is a G protein coupled receptor related to GPR-1 (38% overall amino acid identity), C3a receptor (38%), C5a anaphylatoxin receptor (36%) and formyl Met-Leu-Phe receptors (35%). ChemR23 is more distantly related to the chemokine receptors subfamily (Methner A, Hermey G, Schinke B, Hermans-Borgmeyer I. (1997) Biochem Biophys Res Commun 233: 336-42; Samson M, Edinger A L, Stordeur P, Rucker J, Verhasselt V, Sharron M, Govaerts C, Mollereau C, Vassart G, Doms R W, Parmentier M. (1998) Eur J. Immunol. 28:1689-700). ChemR23 transcripts were found to be abundant in monocyte-derived dendritic cells and macrophages, plasmacytoid DC (pDC), and natural killer (NK) cells. Low expression can also be detected by reverse transcription-PCR in CD4+ T lymphocytes. The gene encoding ChemR23 maps to the q21.2-21.3 region of human chromosome 12, outside the gene clusters identified for chemoattractant receptors. It is a putative chemoattractant receptor and it may play a crucial role in the recruitment and/or trafficking of leukocyte cell populations. ChemR23, by its specific expression in immature dendritic cell populations, as well as macrophages, is an attractive candidate receptor involved in the initiation and early regulation of immune responses.

The ligand for ChemR23, chemerin, was identified as a cDNA which is up-regulated by the treatment of skin raft cultures with the retinoic acid receptor (RAR) beta/gamma-selective anti-psoriatic synthetic retinoid, tazarotene [AGN 190168/ethyl 6-[2-(4,4-dimethylthiochroman-6-yl)-ethynyl] nicotinate] (Nagpal S, Patel S, Jacobe H, DiSepio D, Ghosn C, Malhotra M, Teng M, Duvic M, Chandraratna R A. (1997) J. Invest Dermatol 109: 91-5). Chemerin is first produced as a preprochemerin which undergoes proteolytic processing to reveal agonistic properties at ChemR23. The gene for preprochemerin is located at the 17p13.3 position. Preprochemerin cDNA is 830 bp long and encodes a putative protein product of 163 amino acids.

BRIEF SUMMARY OF THE INVENTION

The present invention provides in one aspect, compounds having Formula I:

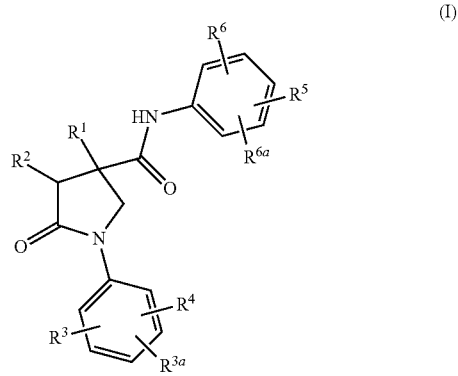

(I)

and the stereoisomers, rotamers and isotopically enriched variants thereof, wherein the substituents $R^1$, $R^2$, $R^3$, $R^{3a}$, $R^4$, $R^5$, $R^6$ and $R^{6a}$ have the meanings provided below.

In related aspects, the present invention provides pharmaceutical compositions comprising one or more of the compounds of Formula I, optionally in admixture with another therapeutic agent, as well as methods for treating diseases or conditions modulated by ChemR23.

DETAILED DESCRIPTION OF THE INVENTION

I. Abbreviation and Definitions

Figure 1A:
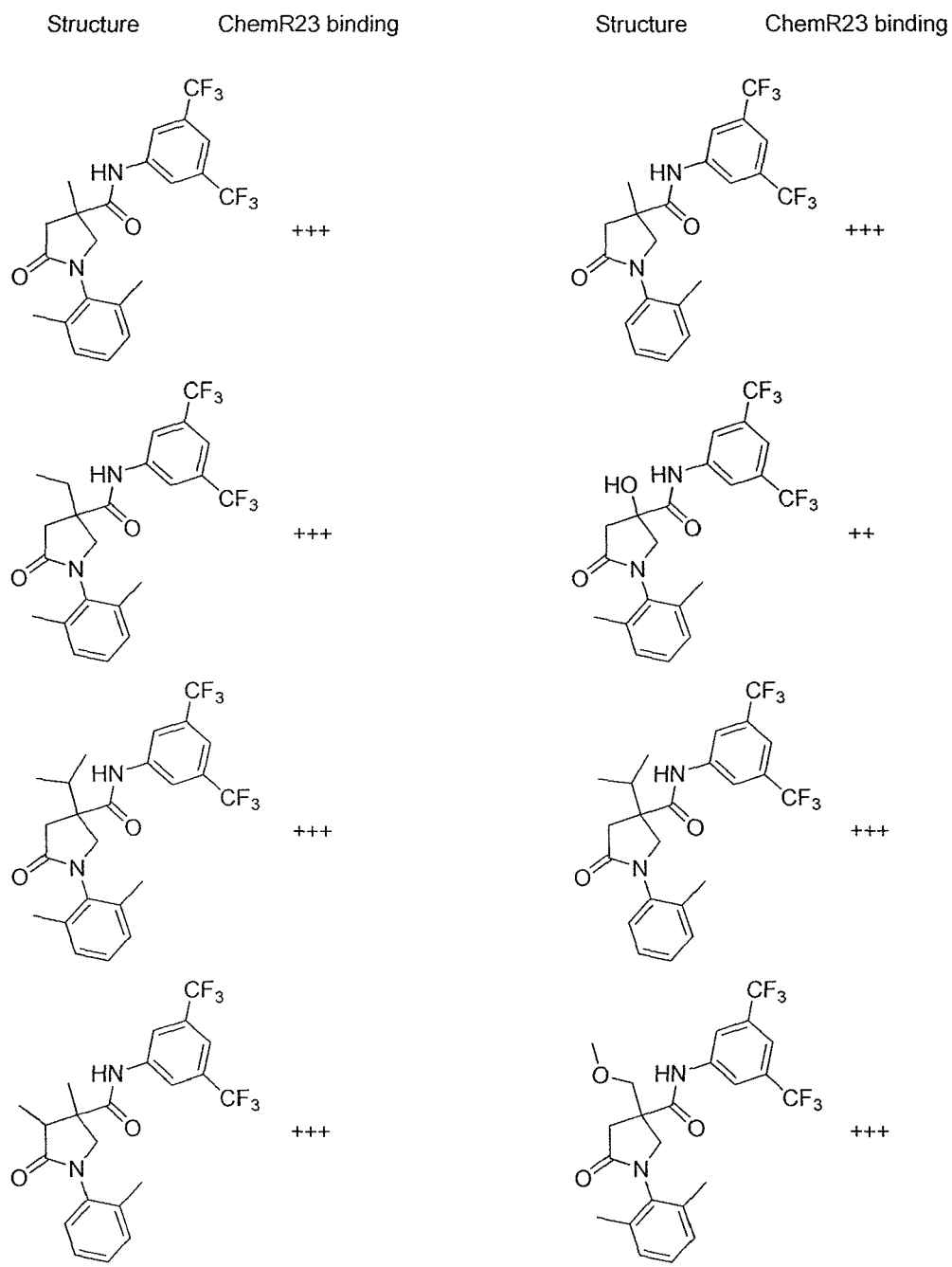
FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W, 1X, 1Y, 1Z, 1AA, 1BB, 1CC, 1DD, 1EE and 1FF provide structures and activity for compounds of the present invention, prepared as described either in the Examples or according to more general schemes below. The activity is provided as follows $IC_{50} \leq 30$ nM, +++; 30 nM<$IC_{50}\leq$300 nM, ++; and 300 nM<$IC_{50}\leq$6000 nM, +.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "〜", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The term "di-($C_{1-4}$ alkyl)amino-$C_{1-4}$ alkyl" refers to an amino group bearing two $C_{1-4}$ alkyl groups that can be the same or different (e.g., methyl, ethyl, propyl, isopropyl, n-butyl, sec-butyl, isobutyl and tert-butyl) and which is attached to the remainder of the molecule through a $C_{1-4}$ alkyl group (a one to four carbon alkylene linking group). Examples of di-($C_{1-4}$ alkyl)amino-$C_{1-4}$ alkyl groups include dimethylaminomethyl, 2-(ethyl(methyl)amino)ethyl, 3-(dimethylamino) butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroarylalkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CONR'R", —OC(O)NR'R", —NR"C(O)R', —NR'—C(O) NR"R''', —NR"C(O)$_2$R', —NH—C(NH$_2$)=NH, —NR'C (NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"ChemR23" also referred to as "ChemerinR", "CMKLR1" or "DEZ" refers to a seven-transmembrane domain presumed G-protein coupled receptor (GPCR).

II. General

Compounds of the present invention can inhibit the binding of ligands to the ChemR23 receptor and are useful in the treatment of various diseases, including psoriasis, multiple sclerosis, and metabolic syndrome.

III. Embodiments of the Invention

A. Compounds

In one aspect, the present invention provides compounds having Formula I:

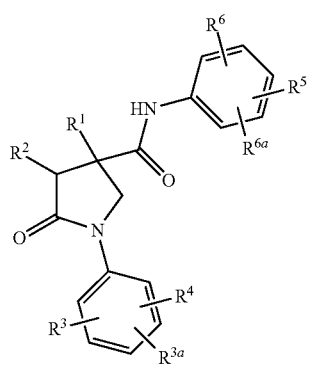

and the stereoisomers, rotamers and isotopically enriched variants thereof, wherein $R^1$ is a member selected from the group consisting of hydrogen, hydroxyl, $C_{1-8}$ alkyl, $C_{2-8}$ alkenyl, $C_{1-8}$ alkoxy, $C_{1-8}$ alkoxy-$C_{1-8}$ alkyl, $C_{1-8}$ haloalkyl, $C_{1-8}$ hydroxyalkyl, $C_{3-8}$ cycloalkyl, $C_{3-8}$ cycloheteroalkyl, $C_{3-8}$ cycloalkyl-$C_{1-3}$ alkyl, $C_{3-8}$ cycloheteroalkyl-$C_{1-3}$ alkyl, heteroaryl, heteroaryl-$C_{1-4}$ alkyl, aryloxy$C_{1-4}$ alkyl, aryl-$C_{1-2}$ alkoxy-$C_{1-4}$ alkyl, —$NR^aR^b$ and $R^aR^bN$—$C_{1-4}$ alkyl wherein $R^a$ and $R^b$ are each independently selected from the group consisting of H, $C_{1-8}$ alkyl, $C_{3-8}$ cycloalkyl, $C_{1-8}$ haloalkyl, $C_{3-8}$ cycloheteroalkyl, $C_{1-8}$ alkoxy-$C_{1-8}$ alkyl, mono- or di-($C_{1-4}$ alkyl)amino-$C_{1-4}$ alkyl, and $C_{1-8}$ hydroxyalkyl, or $R^a$ and $R^b$ are combined with the nitrogen to which each is attached to form a 4- to 7-membered ring optionally having an additional O or N as a ring member and optionally substituted with from 1 to 4 substituents selected from the group consisting of hydroxy, halogen, $C_{1-4}$ alkyl and $C_{1-4}$ haloalkyl;

$R^2$ is a member selected from the group consisting of H, $C_{1-8}$ alkyl, $C_{2-8}$ alkenyl, $C_{1-8}$ alkoxy, $C_{1-8}$ alkoxy-$C_{1-8}$ alkyl, $C_{1-8}$ haloalkyl, $C_{1-8}$ hydroxyalkyl, mono- or di-($C_{1-4}$ alkyl)amino-$C_{1-4}$ alkyl, $C_{3-8}$ cycloalkyl, $C_{3-8}$ cycloheteroalkyl, $C_{3-8}$ cycloalkyl-$C_{1-3}$ alkyl, and $C_{3-8}$ cycloheteroalkyl-$C_{1-3}$ alkyl;

or optionally, $R^1$ and $R^2$ are combined to form a four- to six-membered ring fused to the pyrrolidinone ring and having at least one ring vertex heteroatom selected from the group consisting of O, S and N; or are combined to form a three- to six-membered carbocyclic ring fused to the pyrrolidinone ring and having from zero to two double bonds joining the ring vertices;

$R^3$ and $R^{3a}$ are each members selected from the group consisting of H, halogen, $C_{1-4}$ alkyl, $C_{2-6}$ alkenyl, $C_{3-6}$ cycloalkyl, $C_{3-8}$ cycloheteroalkyl, $C_{3-8}$ cycloalkyl-$C_{1-3}$ alkyl and $C_{3-8}$ cycloheteroalkyl-$C_{1-3}$ alkyl;

$R^4$ is a member selected from the group consisting of H, halogen, $C_{1-4}$ alkyl, $C_{2-6}$ alkenyl, $C_{1-4}$ hydroxyalkyl, $C_{1-4}$ alkoxy, $C_{1-4}$ alkoxy-$C_{1-4}$ alkyl, $C_{1-6}$ haloalkyl, and mono- or di-($C_{1-4}$ alkyl)amino;

$R^5$ is a member selected from the group consisting of $CF_3$, halogen, cyano, $C_{1-4}$ alkyl, $C_{2-6}$ alkenyl, $C_{1-4}$ hydroxyalkyl, $C_{1-5}$ alkoxy, $C_{1-4}$ alkoxy-$C_{1-4}$ alkyl, $C_{1-4}$ alkoxy-$C_{1-4}$ alkoxy, $C_{3-8}$ cycloalkyl, $C_{3-8}$ cycloalkyloxy, $C_{3-8}$ cycloheteroalkyl, $C_{3-8}$ cycloheteroalkyl-$C_{1-3}$ alkyl and mono- or di-($C_{1-4}$ alkyl)amino;

$R^6$ and $R^{6a}$ are each members selected from the group consisting of hydrogen, halogen, cyano, $C_{1-4}$ alkyl, $C_{1-4}$ haloalkyl, $C_{2-6}$ alkenyl, $C_{1-4}$ hydroxyalkyl, $C_{1-5}$ alkoxy, $C_{1-4}$ alkoxy-$C_{1-4}$ alkyl, $C_{1-4}$ alkoxy-$C_{1-4}$ alkoxy, $C_{3-8}$ cycloalkyl, $C_{3-8}$ cycloalkyloxy, $C_{3-8}$ cycloheteroalkyl, $C_{3-8}$ cycloheteroalkyl-$C_{1-3}$ alkyl and mono- or di-($C_{1-4}$ alkyl)amino;

wherein any ring portions of $R^1$, $R^2$, $R^3$, $R^{3a}$, $R^4$, $R^5$, $R^6$ and $R^{6a}$, including the optional fused rings, are optionally substituted with from 1 to 3 substituents independently selected from the group consisting of halogen, $C_{1-4}$ alkyl, benzyl, oxo and $C_{1-6}$ alkoxycarbonyl, and any cycloalkyl and cycloheteroalkyl portions optionally have a double bond between ring vertices;

and pharmaceutically acceptable salts thereof.

In one group of embodiments, compounds are provided having the Formula Ia:

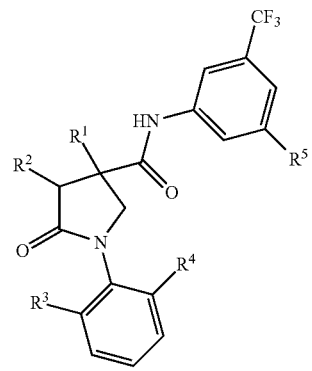

and the stereoisomers, rotamers and isotopically enriched variants thereof, wherein $R^1$ is a member selected from the group consisting of hydroxyl, $C_{1-8}$ alkyl, $C_{2-8}$ alkenyl, $C_{1-8}$ alkoxy, $C_{1-8}$ alkoxy-$C_{1-8}$ alkyl, $C_{1-8}$ haloalkyl, $C_{1-8}$ hydroxyalkyl, $C_{3-8}$ cycloalkyl, $C_{3-8}$ cycloheteroalkyl, $C_{3-8}$ cycloalkyl-$C_{1-3}$ alkyl, $C_{3-8}$ cycloheteroalkyl-$C_{1-3}$ alkyl, heteroaryl, heteroaryl-$C_{1-4}$ alkyl, aryloxy$C_{1-4}$ alkyl, aryl-$C_{1-2}$ alkoxy-$C_{1-4}$ alkyl, —$NR^aR^b$ and $R^aR^bN$—$C_{1-4}$ alkyl wherein $R^a$ and $R^b$ are each independently selected from the group consisting of H, $C_{1-8}$ alkyl, $C_{3-8}$ cycloalkyl, $C_{1-8}$ haloalkyl, $C_{3-8}$ cycloheteroalkyl, $C_{1-8}$ alkoxy-$C_{1-8}$ alkyl, mono- or di-($C_{1-4}$ alkyl)amino-$C_{1-4}$ alkyl, and $C_{1-8}$ hydroxyalkyl, or $R^a$ and $R^b$ are combined with the nitrogen to which each is attached to form a 4- to 7-membered ring optionally having an additional O or N as a ring member and optionally substituted with from 1 to 4 substituents selected from the group consisting of hydroxy, halogen, $C_{1-4}$ alkyl and $C_{1-4}$ haloalkyl;

$R^2$ is a member selected from the group consisting of H, $C_{1-8}$ alkyl, $C_{2-8}$ alkenyl, $C_{1-8}$ alkoxy, $C_{1-8}$ alkoxy-$C_{1-8}$ alkyl, $C_{1-8}$ haloalkyl, $C_{1-8}$ hydroxyalkyl, mono- or di-($C_{1-4}$ alkyl)amino-$C_{1-4}$ alkyl, $C_{3-8}$ cycloalkyl, $C_{3-8}$ cycloheteroalkyl, $C_{3-8}$ cycloalkyl-$C_{1-3}$ alkyl, and $C_{3-8}$ cycloheteroalkyl-$C_{1-3}$ alkyl;

or optionally, $R^1$ and $R^2$ are combined to form a four- to six-membered ring fused to the pyrrolidinone ring and having at least one ring vertex heteroatom selected from the group consisting of O, S and N;

$R^3$ is a member selected from the group consisting of H, halogen, $C_{1-4}$ alkyl, $C_{2-6}$ alkenyl, $C_{3-6}$ cycloalkyl, $C_{3-8}$ cycloheteroalkyl, $C_{3-8}$ cycloalkyl-$C_{1-3}$ alkyl and $C_{3-8}$ cycloheteroalkyl-$C_{1-3}$ alkyl;

$R^4$ is a member selected from the group consisting of H, halogen, $C_{1-4}$ alkyl, $C_{2-6}$ alkenyl, $C_{1-4}$ hydroxyalkyl, $C_{1-4}$ alkoxy, $C_{1-4}$ alkoxy-$C_{1-4}$ alkyl, $C_{1-6}$ haloalkyl, and mono- or di-($C_{1-4}$ alkyl)amino;

$R^5$ is a member selected from the group consisting of $CF_3$, halogen, cyano, $C_{1-4}$ alkyl, $C_{2-6}$ alkenyl, $C_{1-4}$ hydroxyalkyl, $C_{1-5}$ alkoxy, $C_{1-4}$ alkoxy-$C_{1-4}$ alkyl, $C_{1-4}$ alkoxy-$C_{1-4}$ alkoxy, $C_{3-8}$ cycloalkyl, $C_{3-8}$ cycloalkyloxy, $C_{3-8}$ cycloheteroalkyl, $C_{3-8}$ cycloheteroalkyl-$C_{1-3}$ alkyl and mono- or di-($C_{1-4}$ alkyl)amino;

wherein any ring portions of $R^1$, $R^2$, $R^3$, $R^4$ and $R^5$ are optionally substituted with from 1 to 3 substituents independently selected from the group consisting of halogen, $C_{1-4}$ alkyl, benzyl, oxo and $C_{1-6}$ alkoxycarbonyl, and any cycloalkyl and cycloheteroalkyl portions optionally have a double bond between ring vertices; and pharmaceutically acceptable salts thereof.

In one embodiment, the compounds of Formula Ia are those compounds wherein $R^3$ is methyl. In another embodiment, $R^3$ is methyl, and $R^4$ is H or $C_{1-4}$ alkyl. In still another embodiment, $R^2$ is H or $C_{1-8}$ alkyl, $R^3$ is methyl, and $R^4$ is H or $C_{1-4}$ alkyl. In yet another embodiment, $R^5$ is $CF_3$. In a select group of embodiments, the compounds of Formula Ia are those compounds wherein $R^3$ is methyl and $R^5$ is $CF_3$.

In another group of embodiments, the compounds of Formula Ia are those represented by Formula Ib,

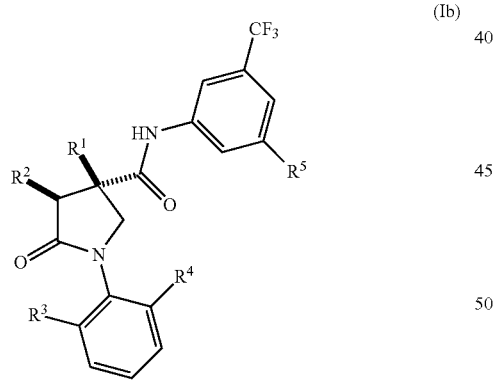

(Ib)

wherein $R^1$, $R^2$, $R^3$, $R^4$ and $R^5$ have the meanings provided with reference to Formula Ia. Within the embodiments of Formula Ib, a selected group of compounds are those in which $R^1$ is selected from —$NR^aR^b$ and $R^aR^bN$—$C_{1-4}$ alkyl. In one selected embodiment, $R^1$ is —$NR^aR^b$. In another selected embodiment, $R^1$ is $R^aR^bN$—$C_{1-4}$ alkyl. In other embodiments, $R^3$ and $R^4$ are each methyl. In another selected group of compounds, $R^5$ is $CF_3$, CN or cyclopropyl. In another group of embodiments of Formula Ib, $R^1$ is mono- or di-($C_{1-4}$ alkyl)amino-$C_{1-4}$ alkyl, and $R^3$ is methyl. Particularly preferred are the compounds wherein $R^1$ is di($C_{1-4}$ alkyl)aminomethyl. In still another group of embodiments of Formula Ib, $R^2$ and $R^3$ are each methyl.

In another group of embodiments, compounds are provided having Formula Ic:

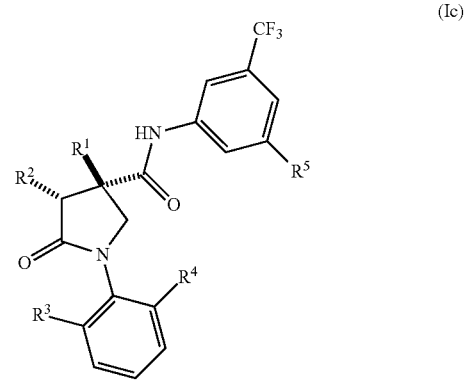

(Ic)

wherein $R^1$, $R^2$, $R^3$, $R^4$ and $R^5$ have the meanings provided with reference to Formula Ia. In one selected group of embodiments of Formula Ic, $R^2$ is H, and $R^3$ and $R^4$ are each methyl. In another selected group of embodiments, $R^5$ is $CF_3$.

Specific embodiments of the invention are compounds selected from

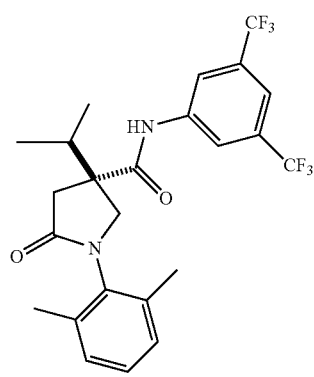

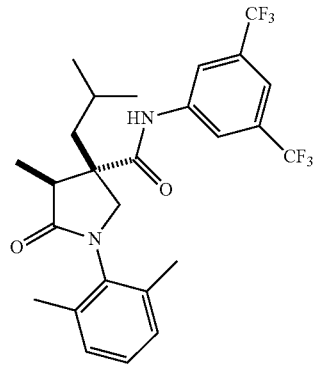

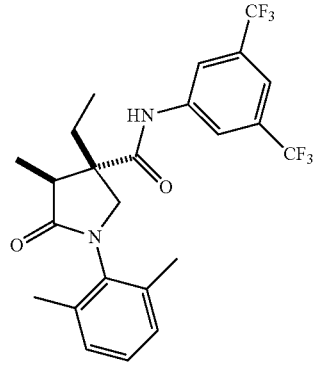

-continued

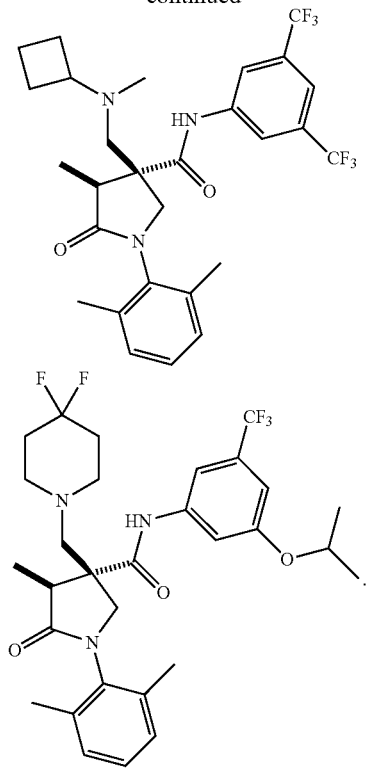

Figure 1B:
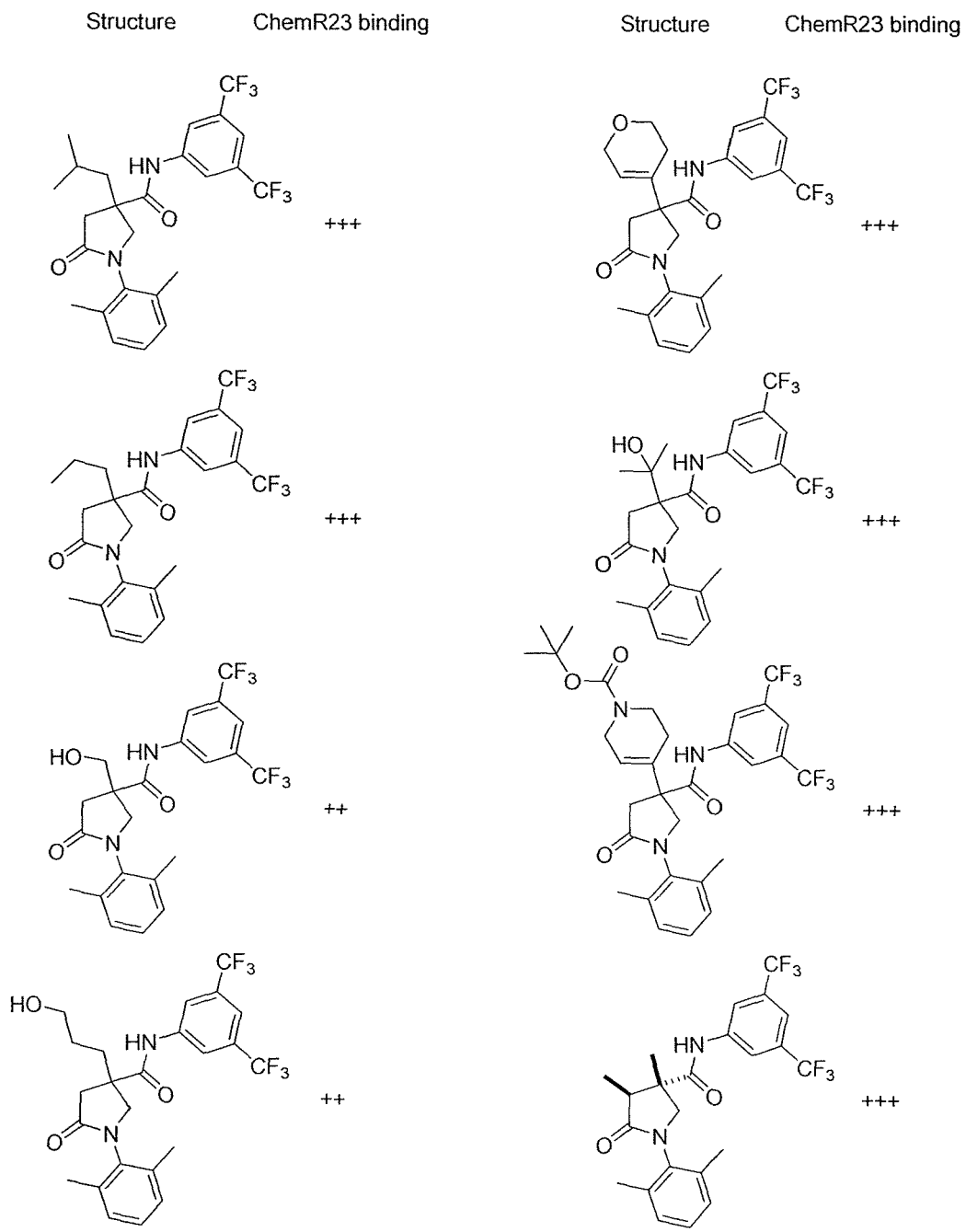
Figure 1C:
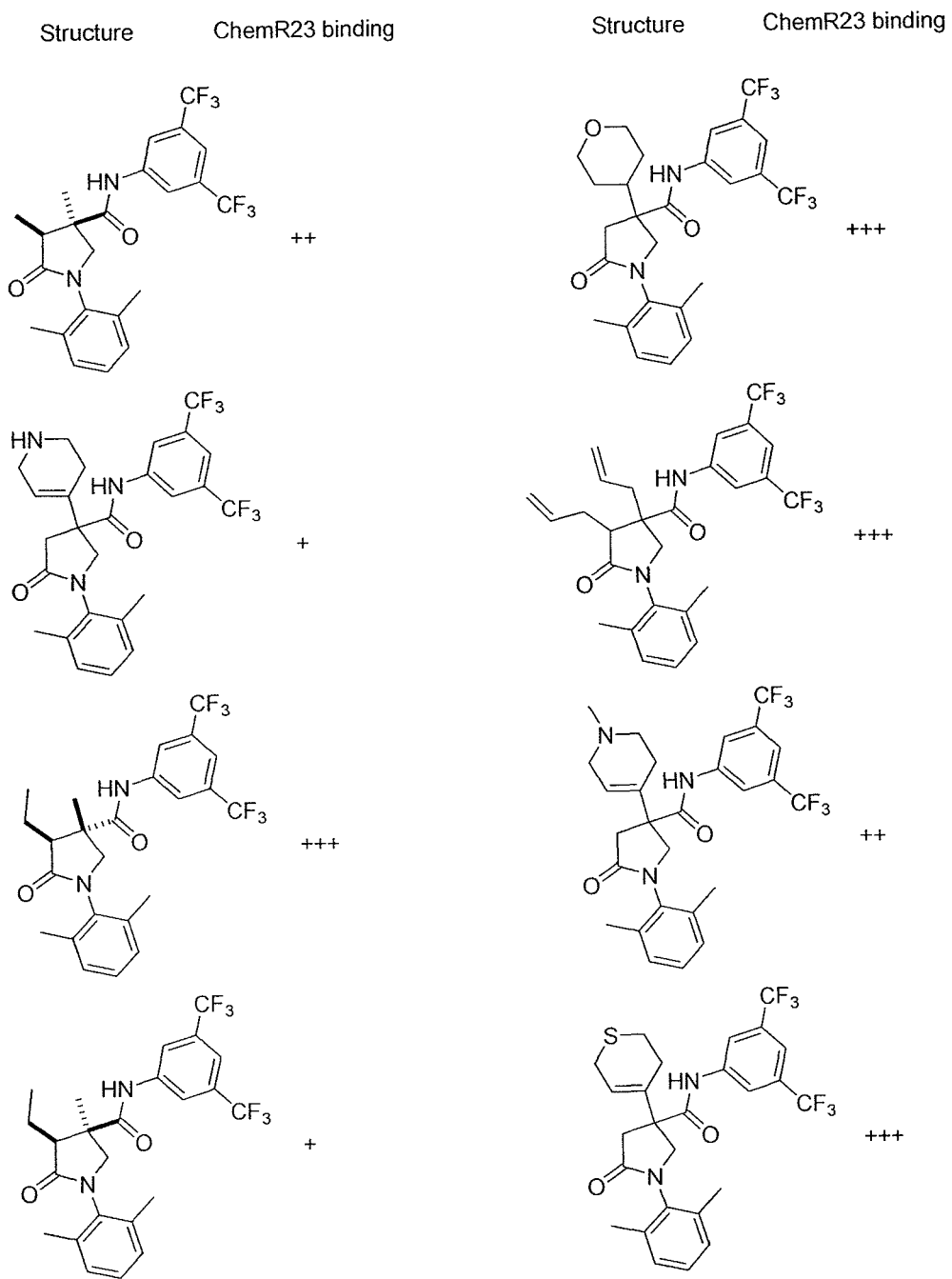
Figure 1D:
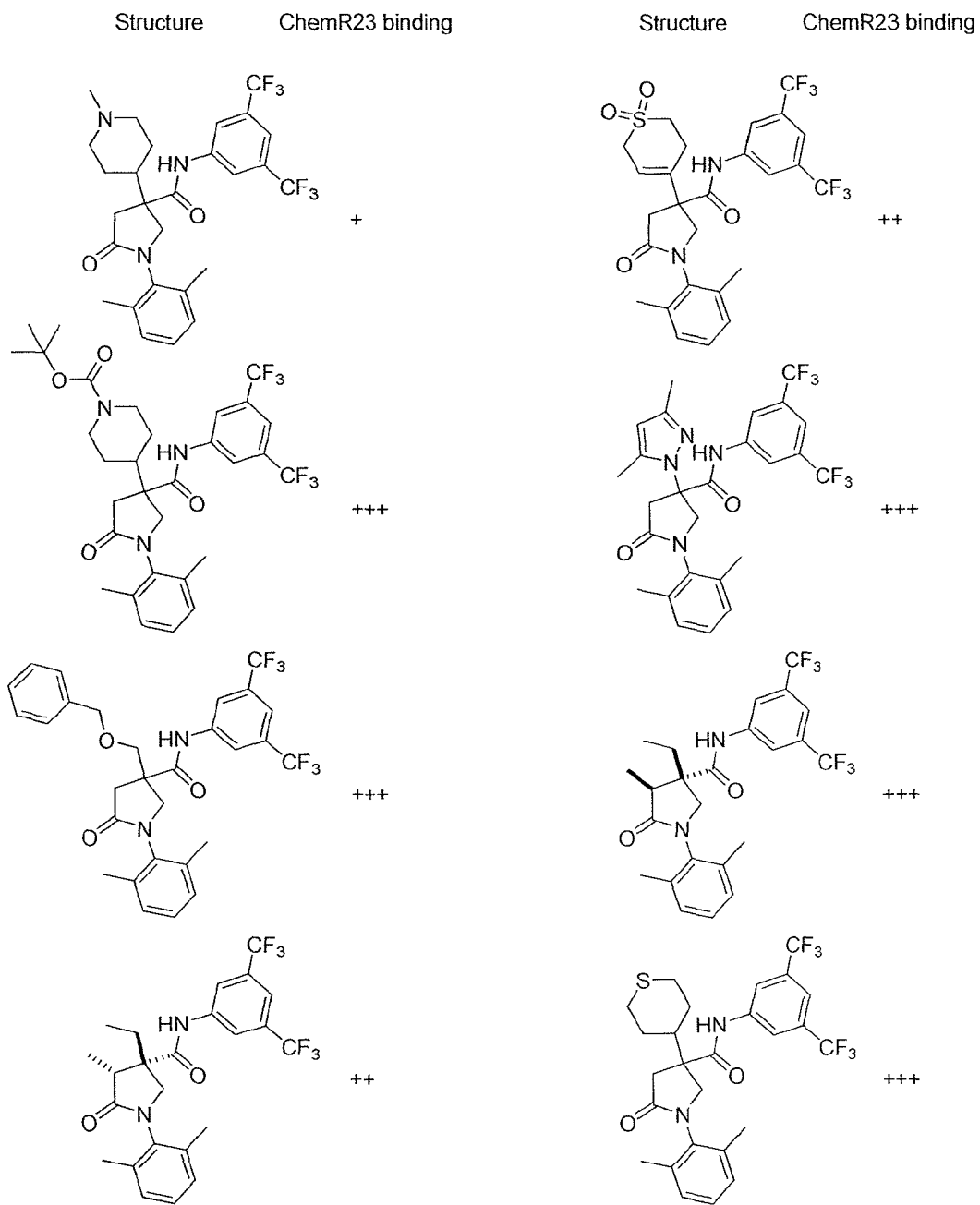
Figure 1E:
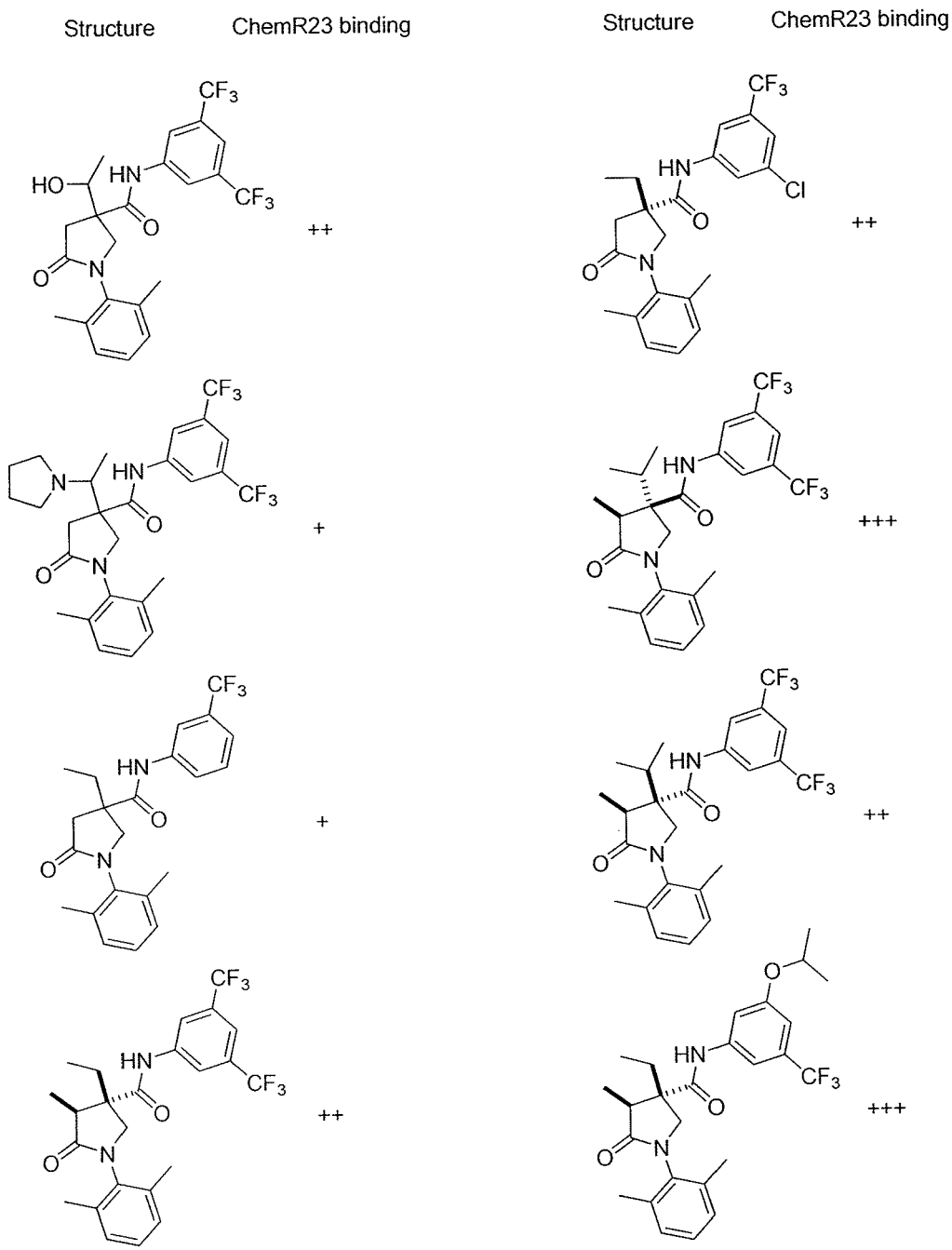
Figure 1F:
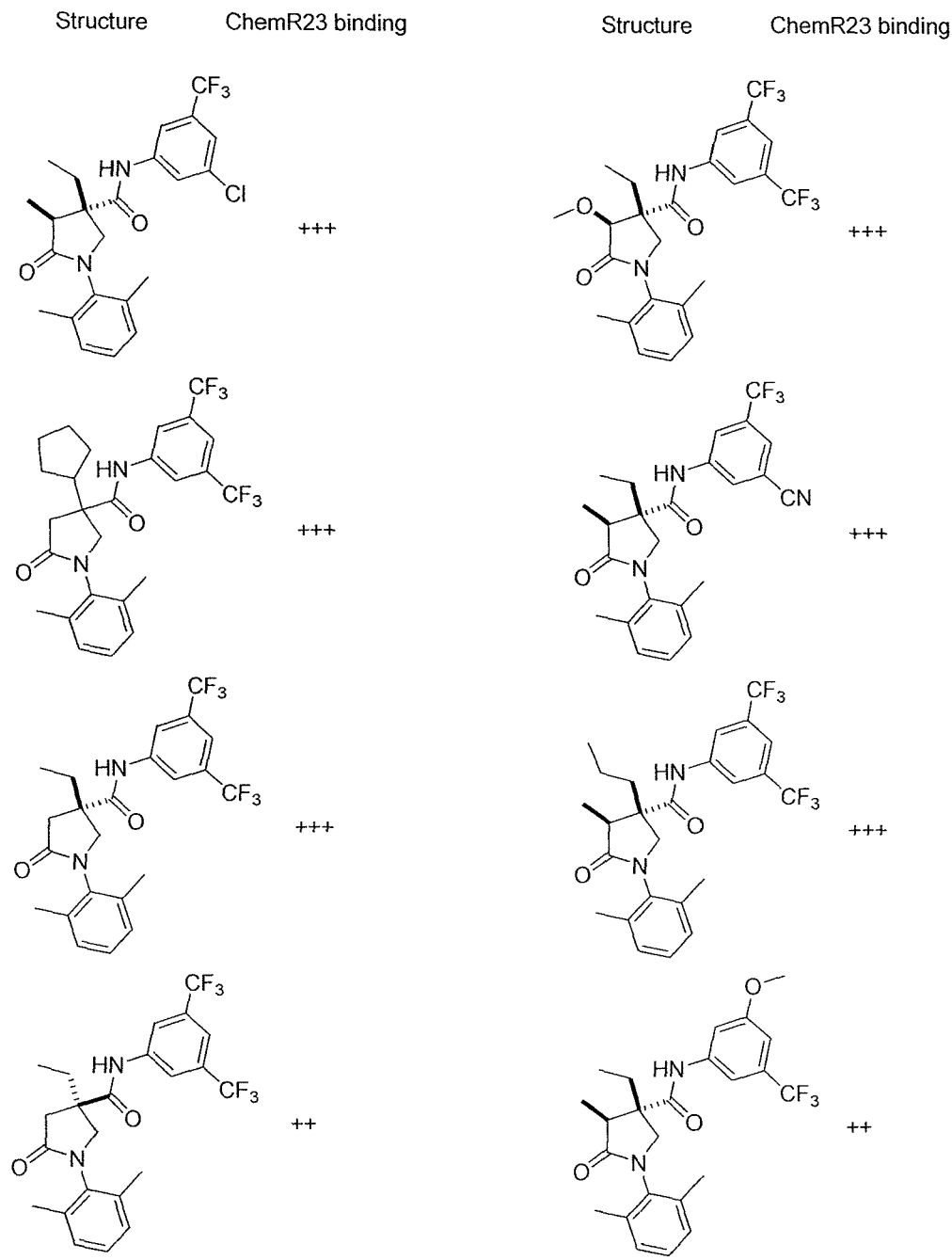
Figure 1G:
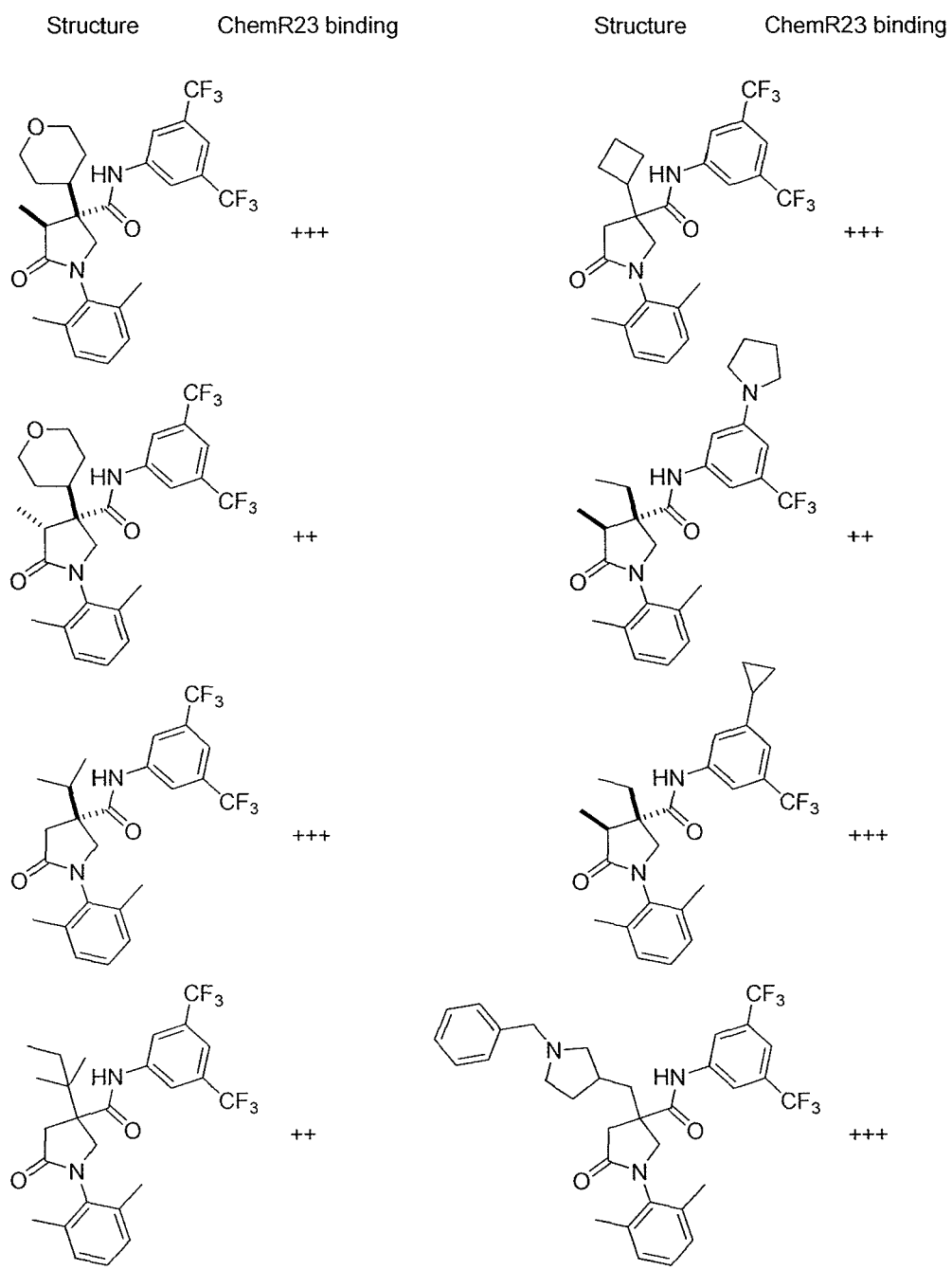
Figure 1H:
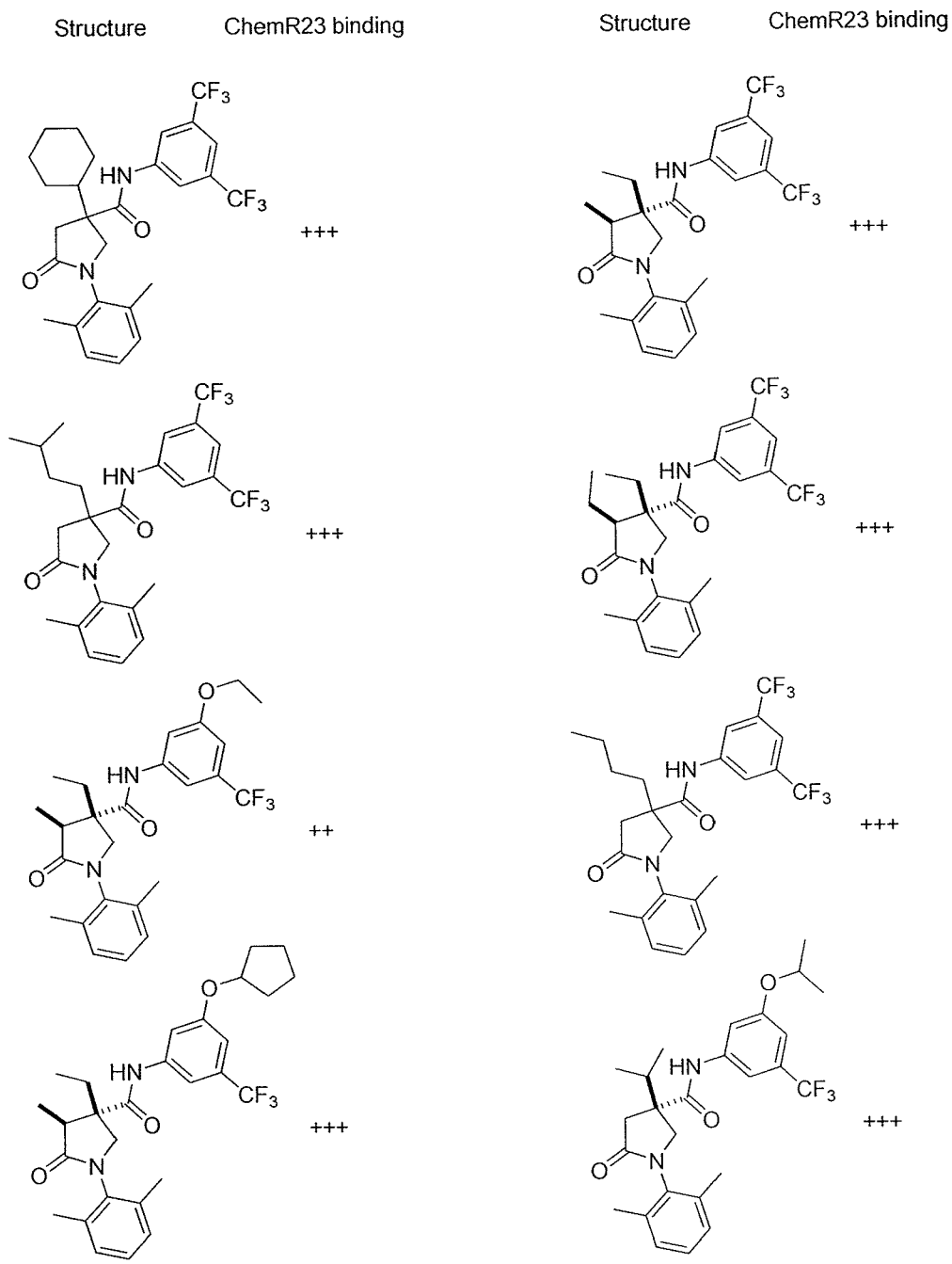
Figure 1I:
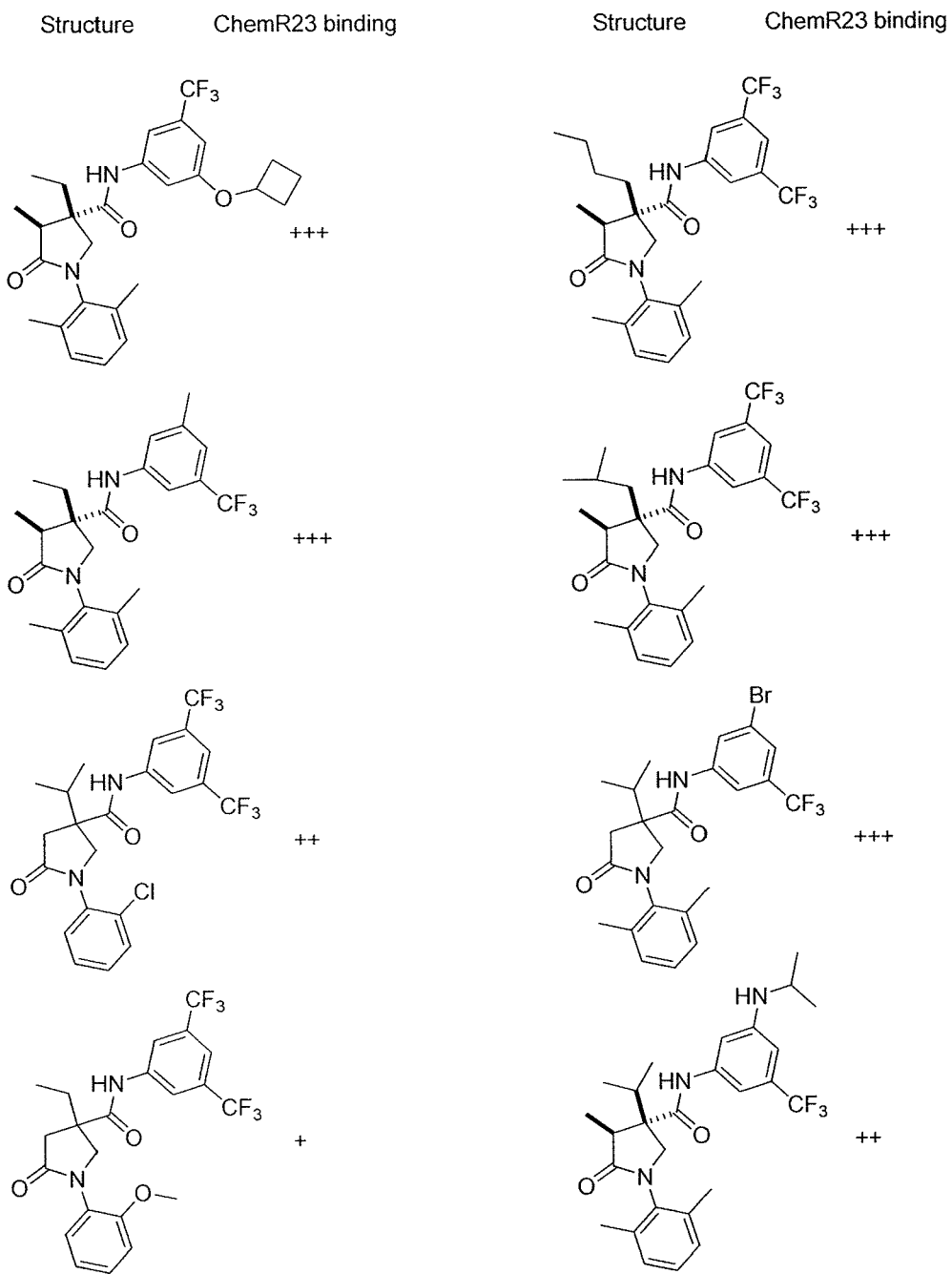
Figure 1J:
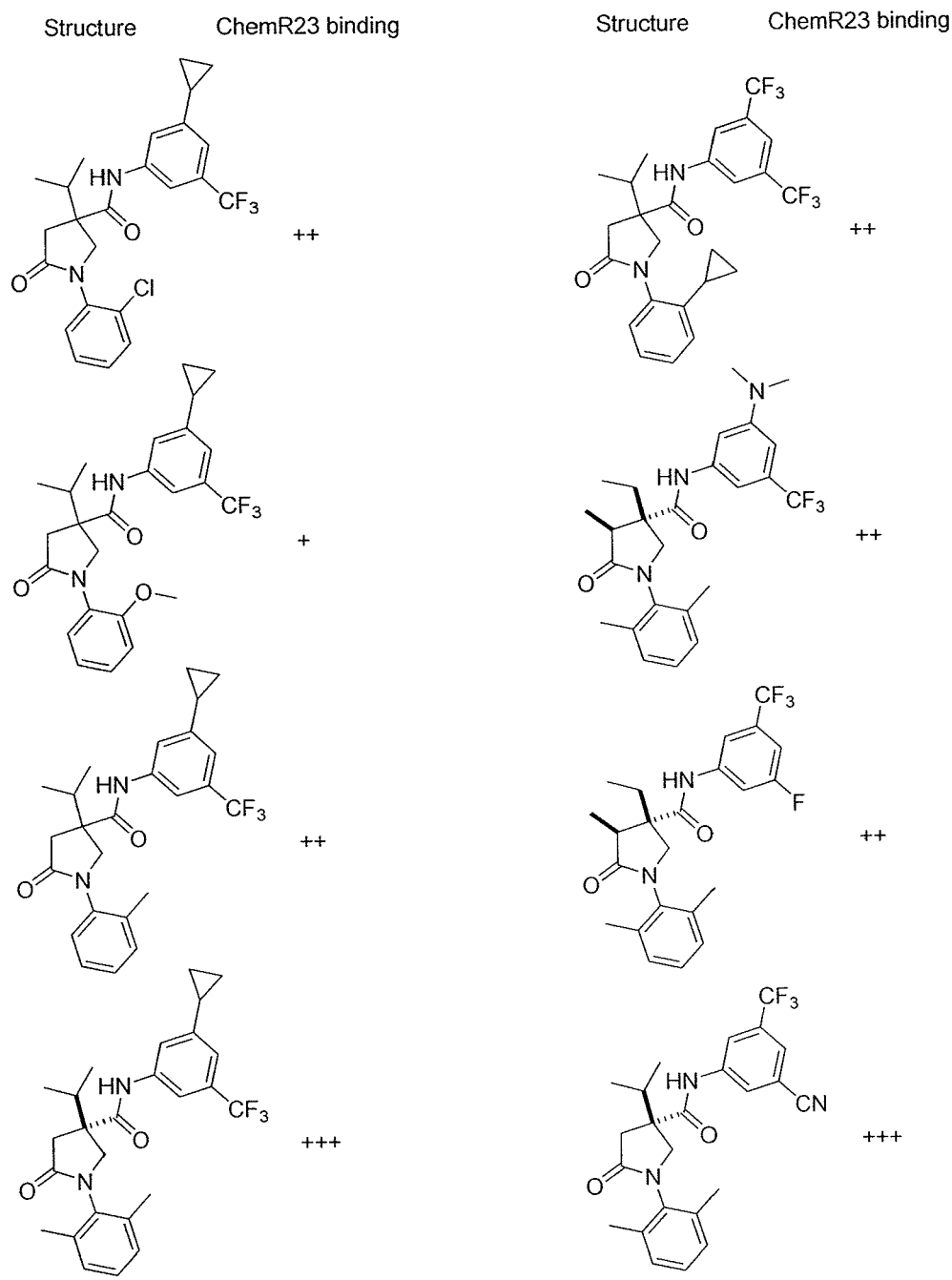
Figure 1K:
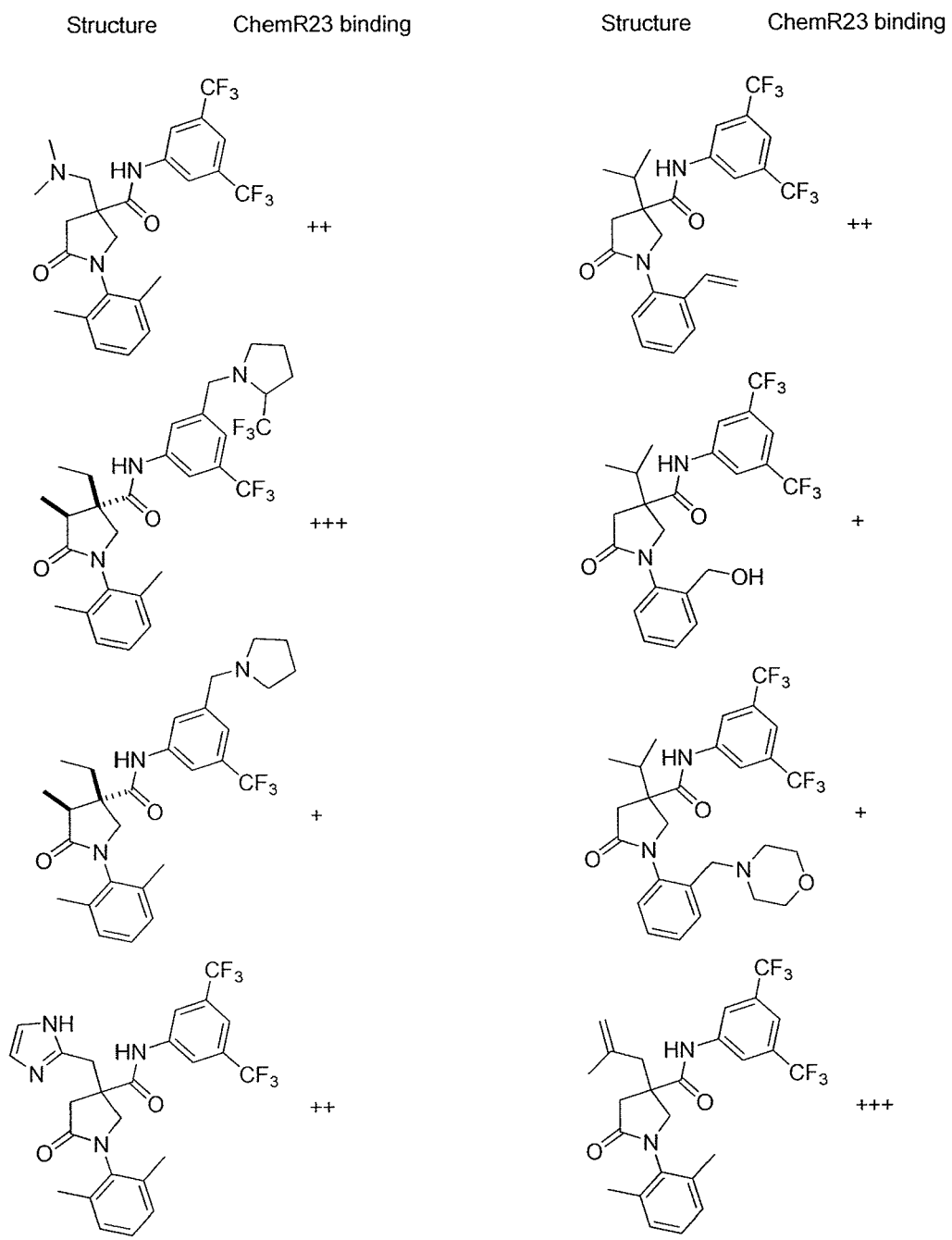
Figure 1L:
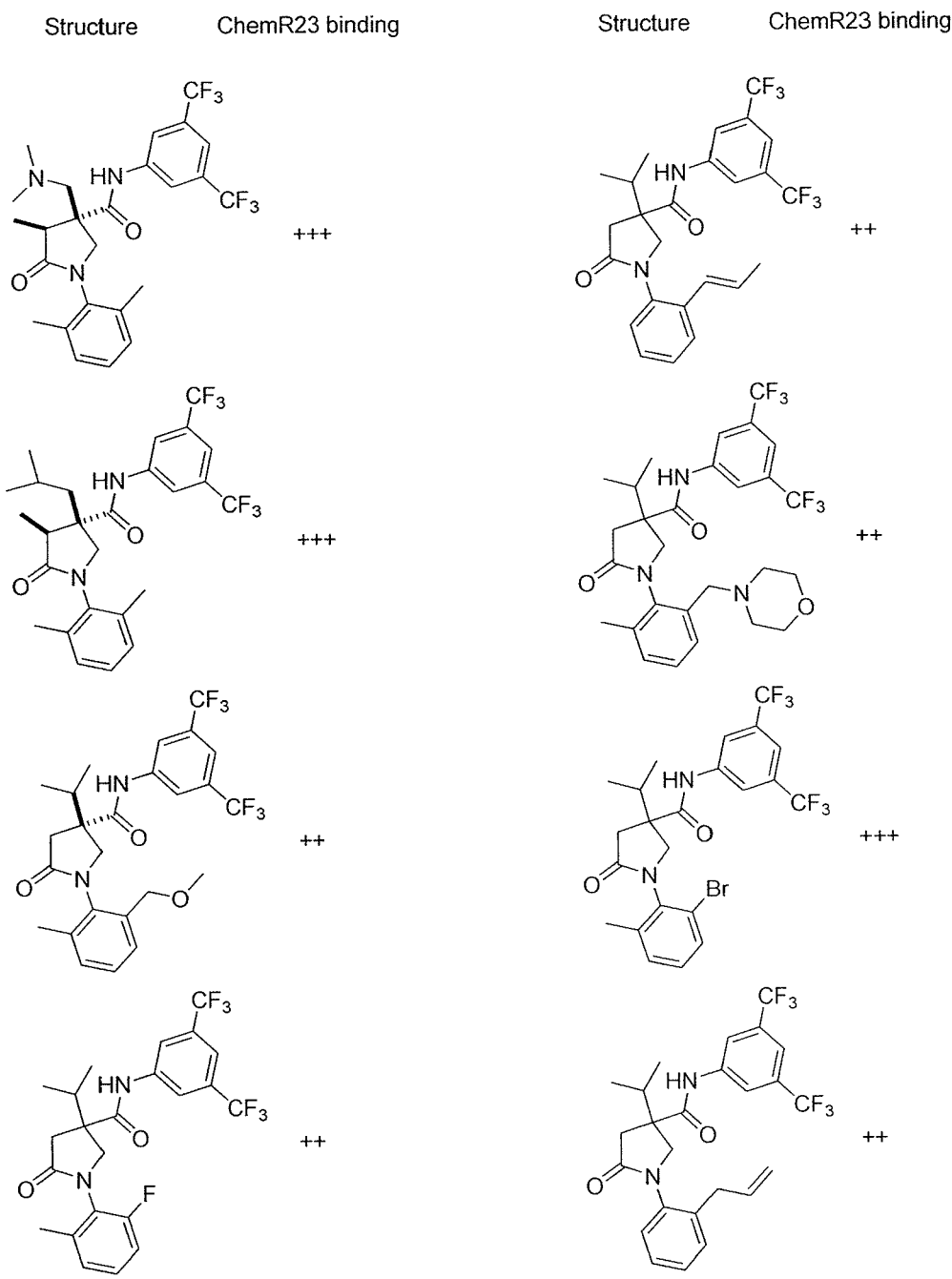
Figure 1M:
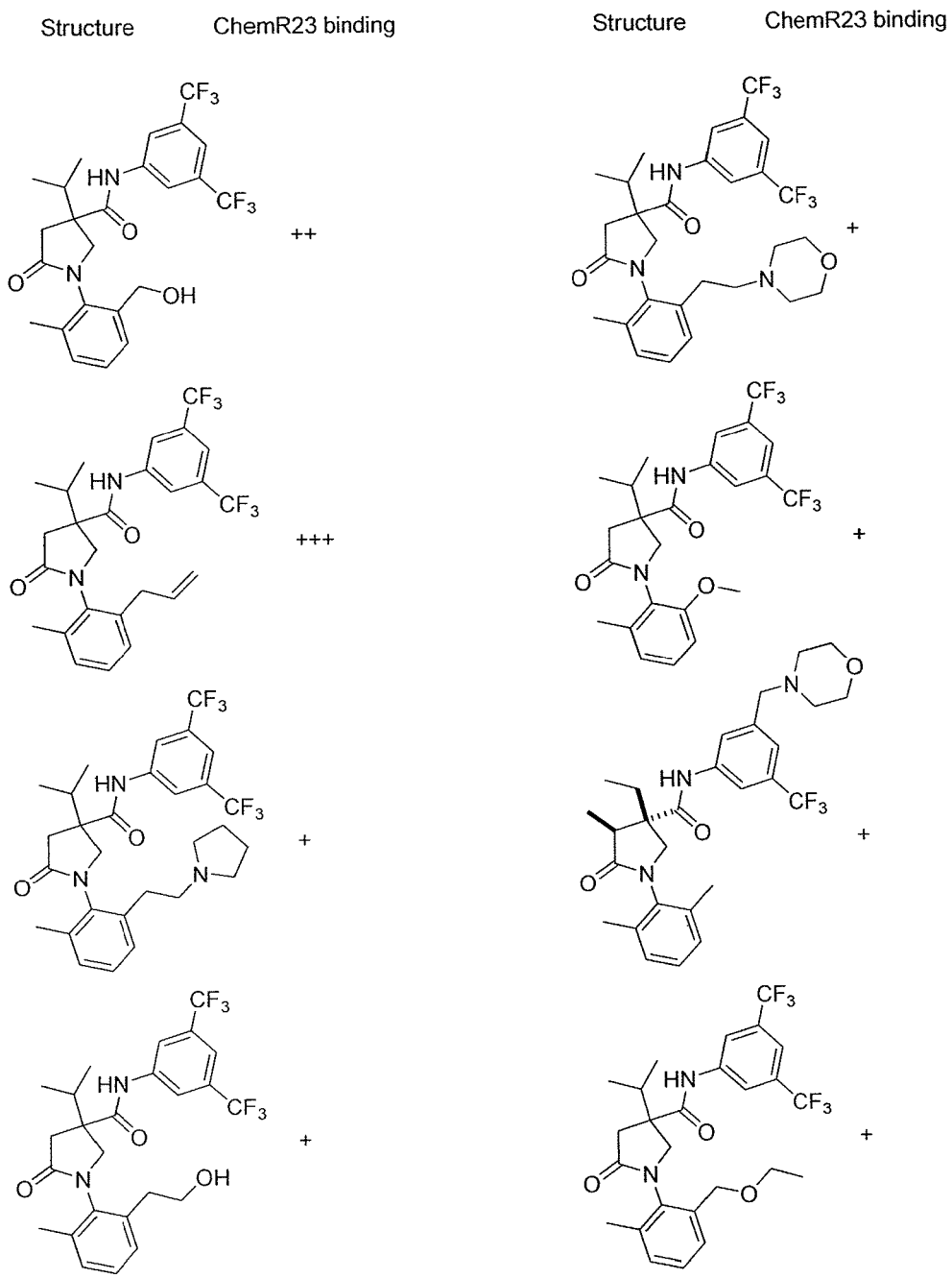
Figure 1N:
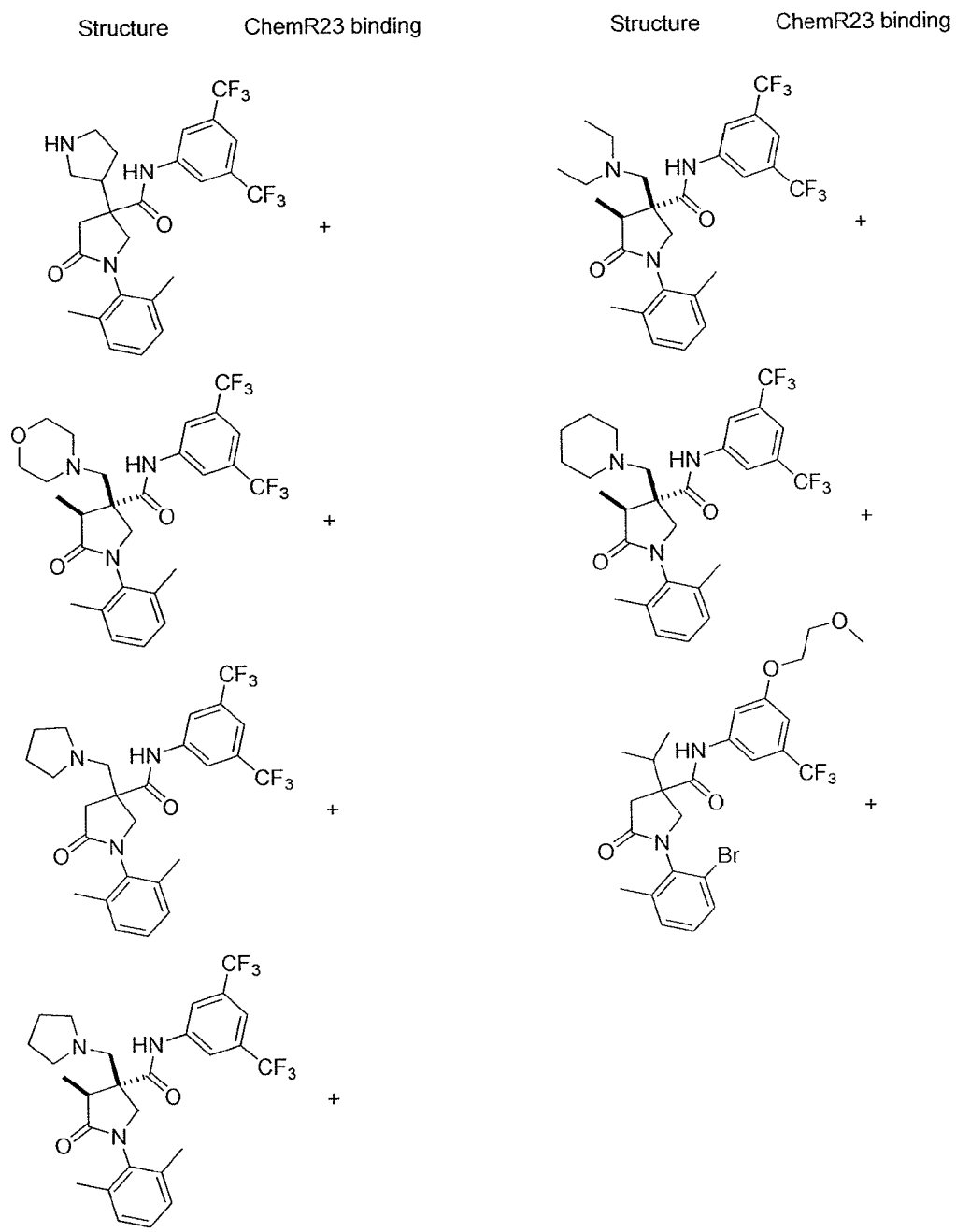
Figure 1O:
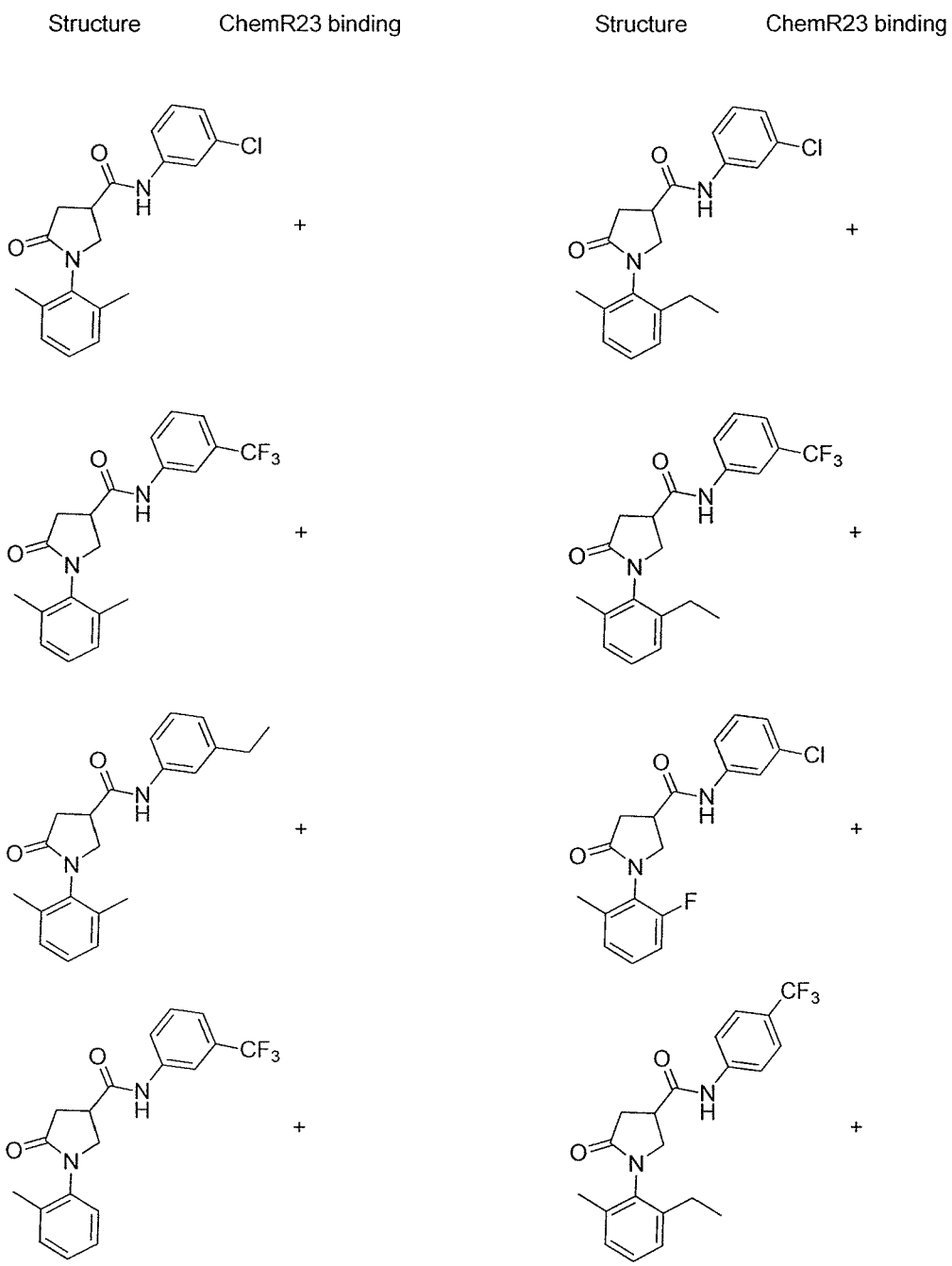
Figure 1P:
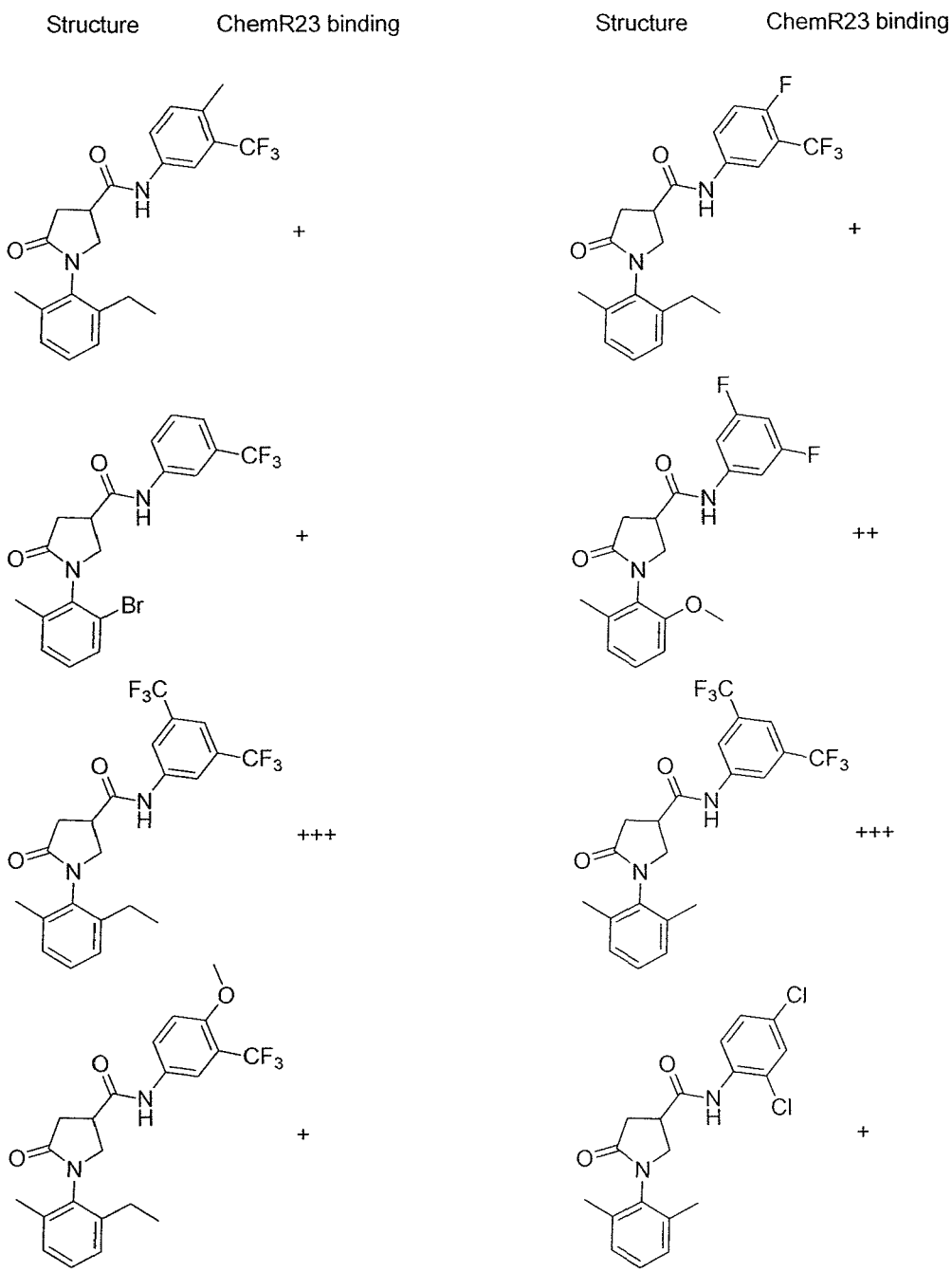
Figure 1Q:
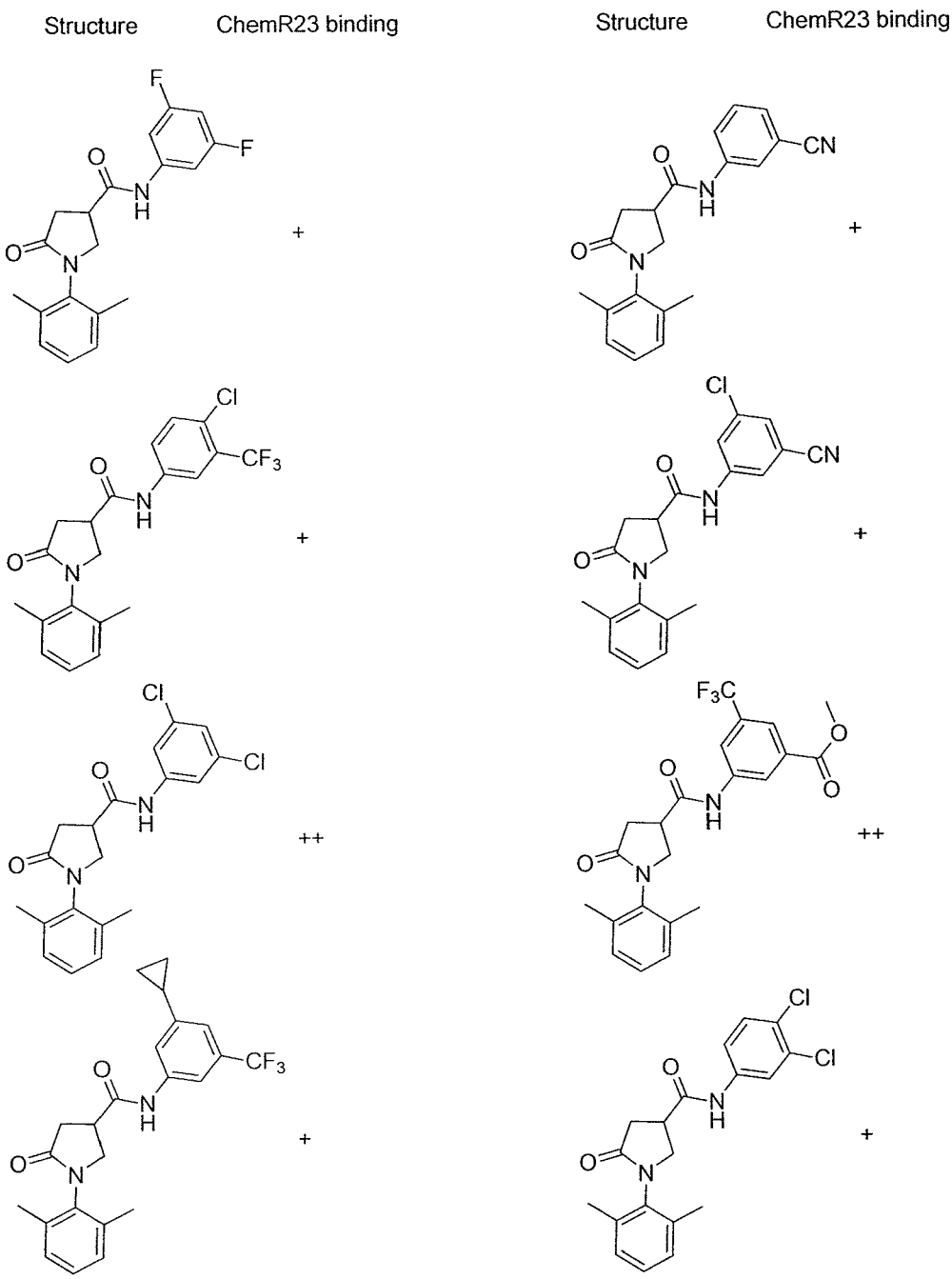
Figure 1R:
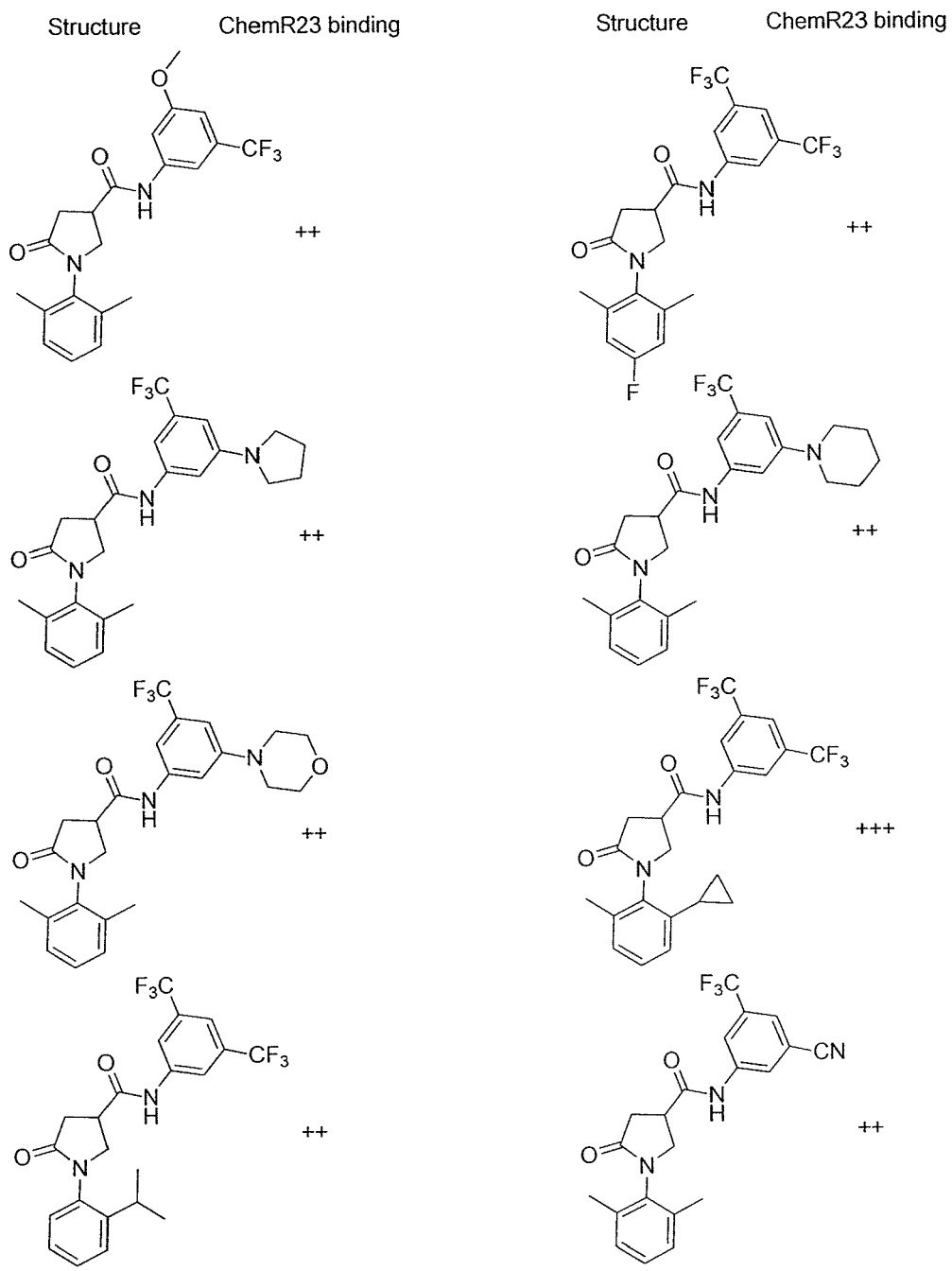
Figure 1S:
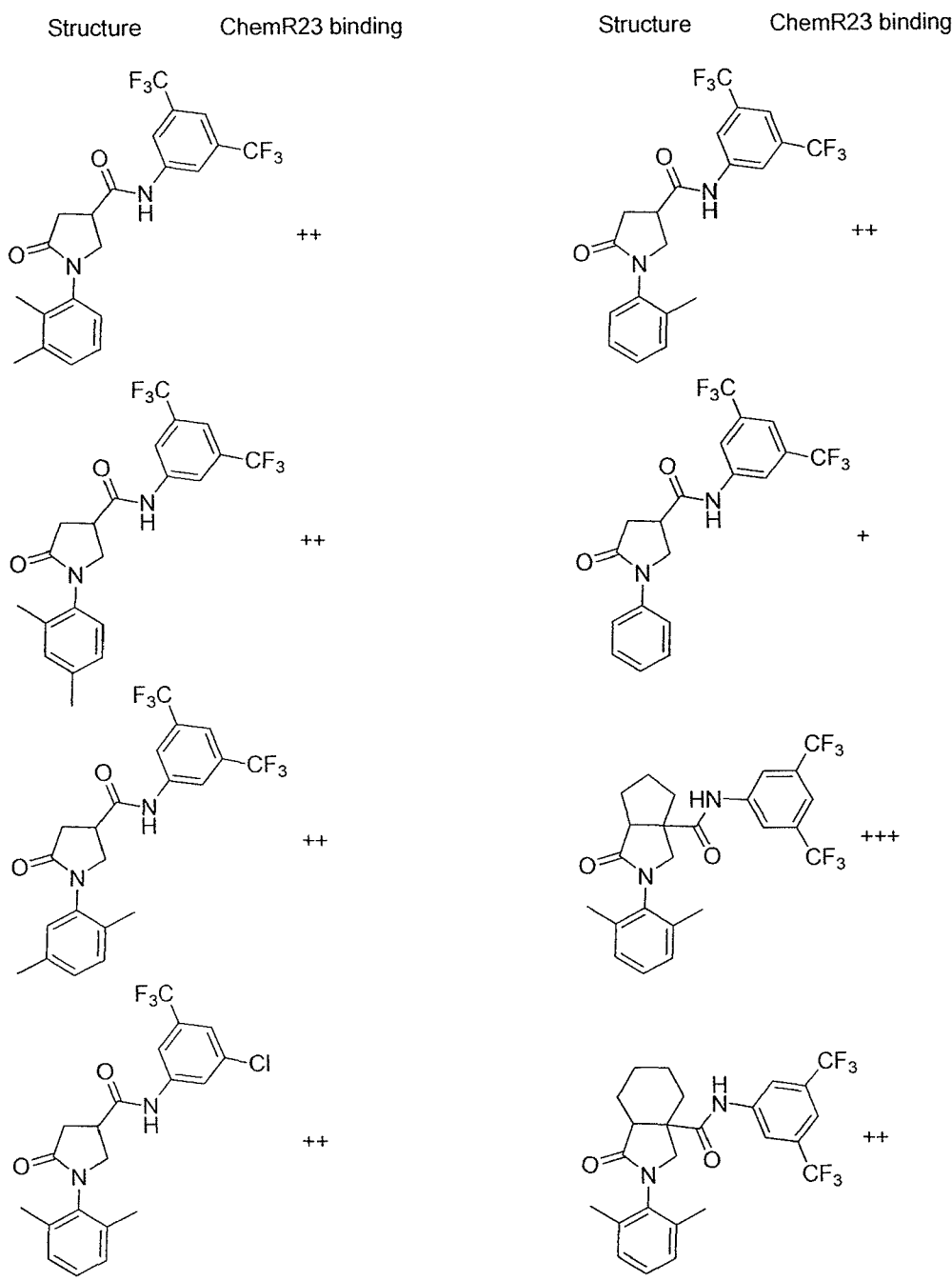
Figure 1T:
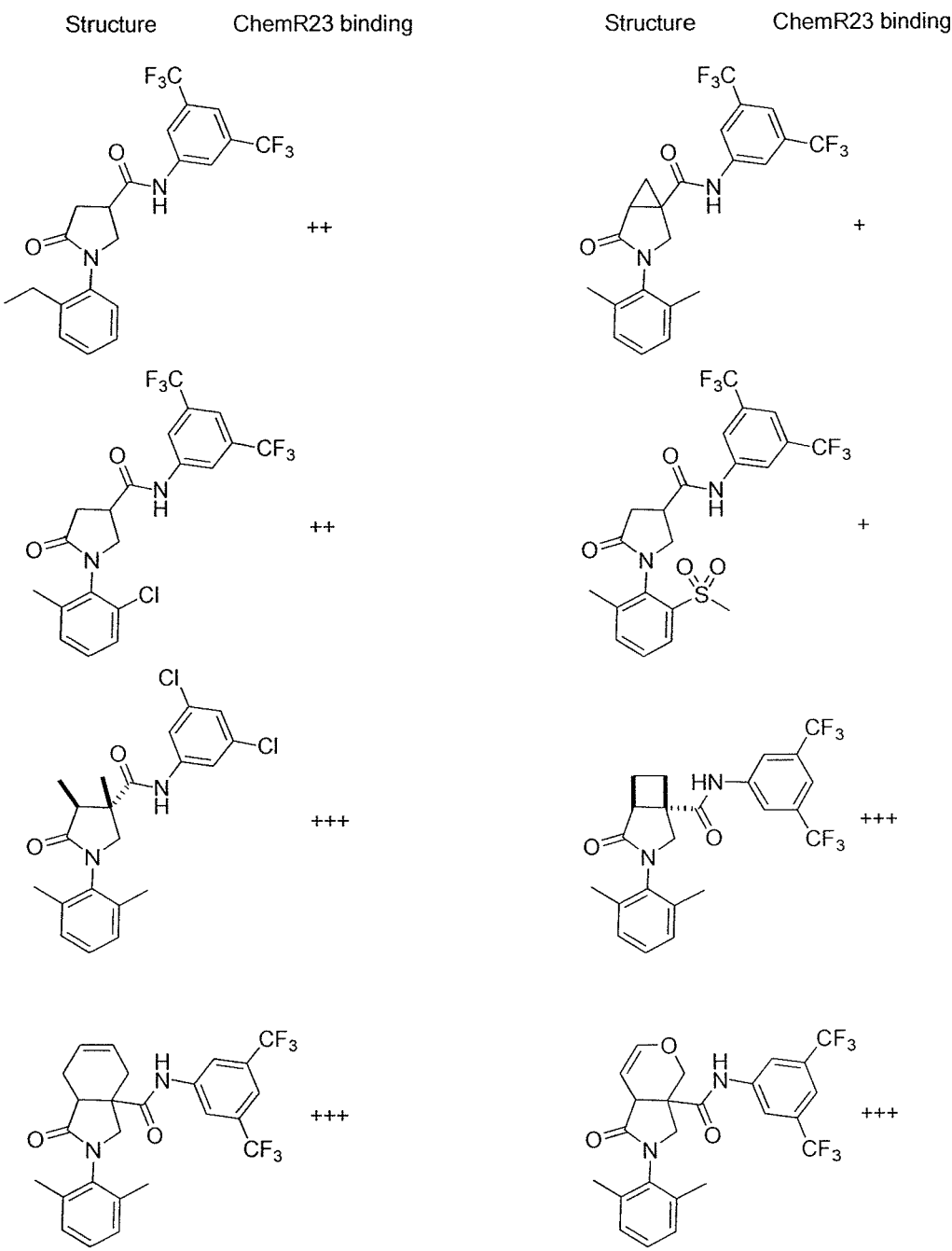
Figure 1U:
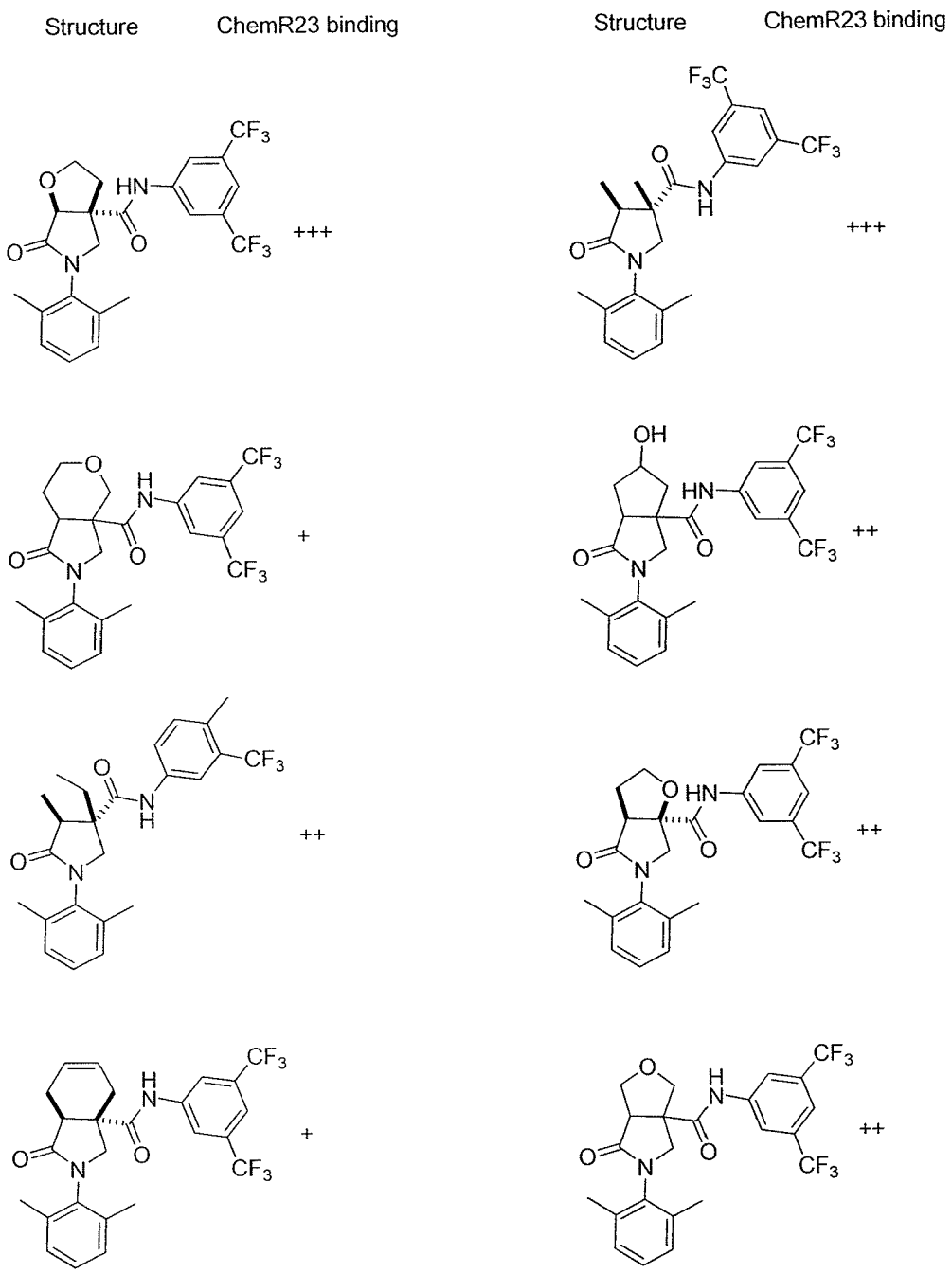
Figure 1V:
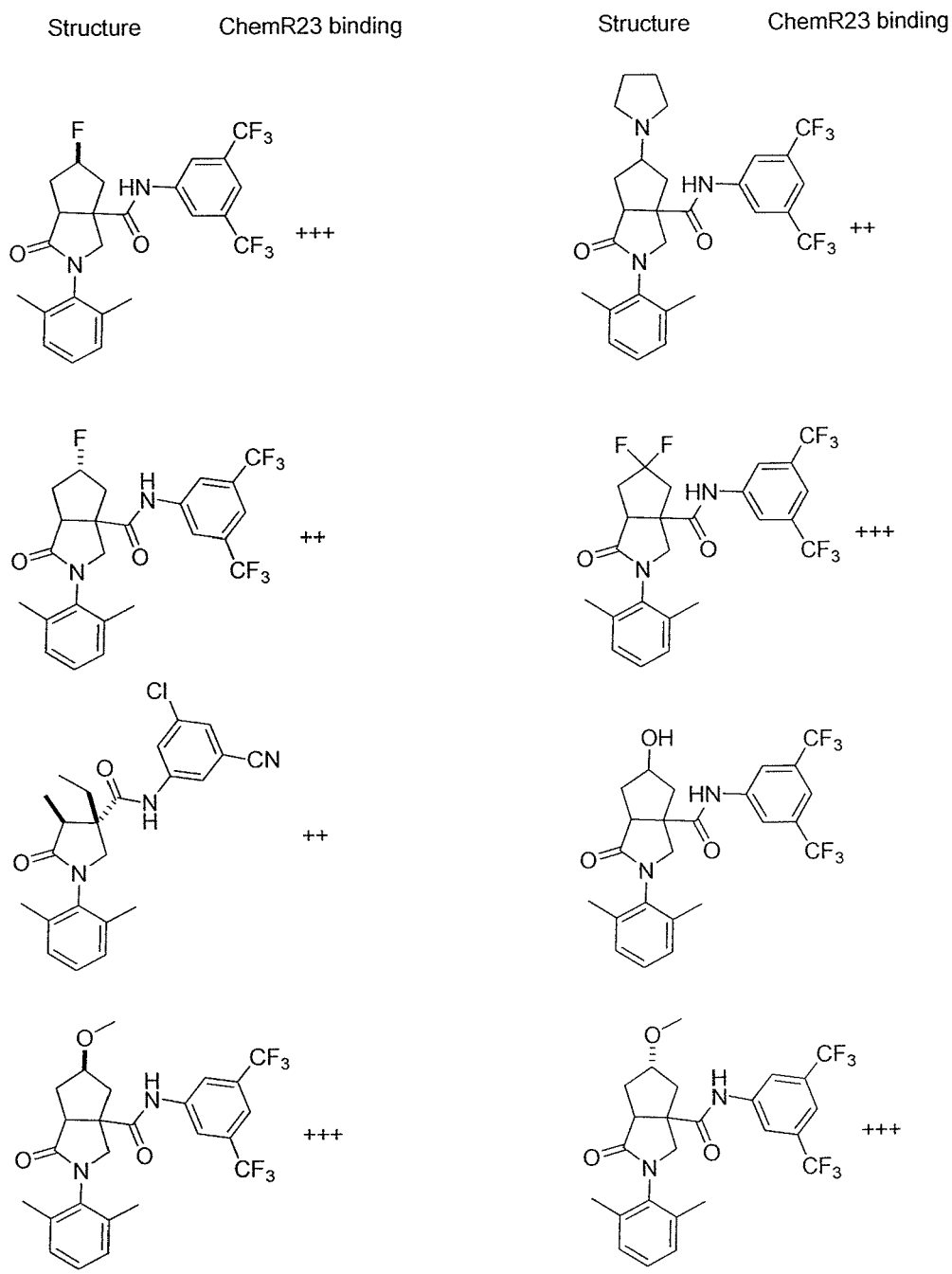
Figure 1W:
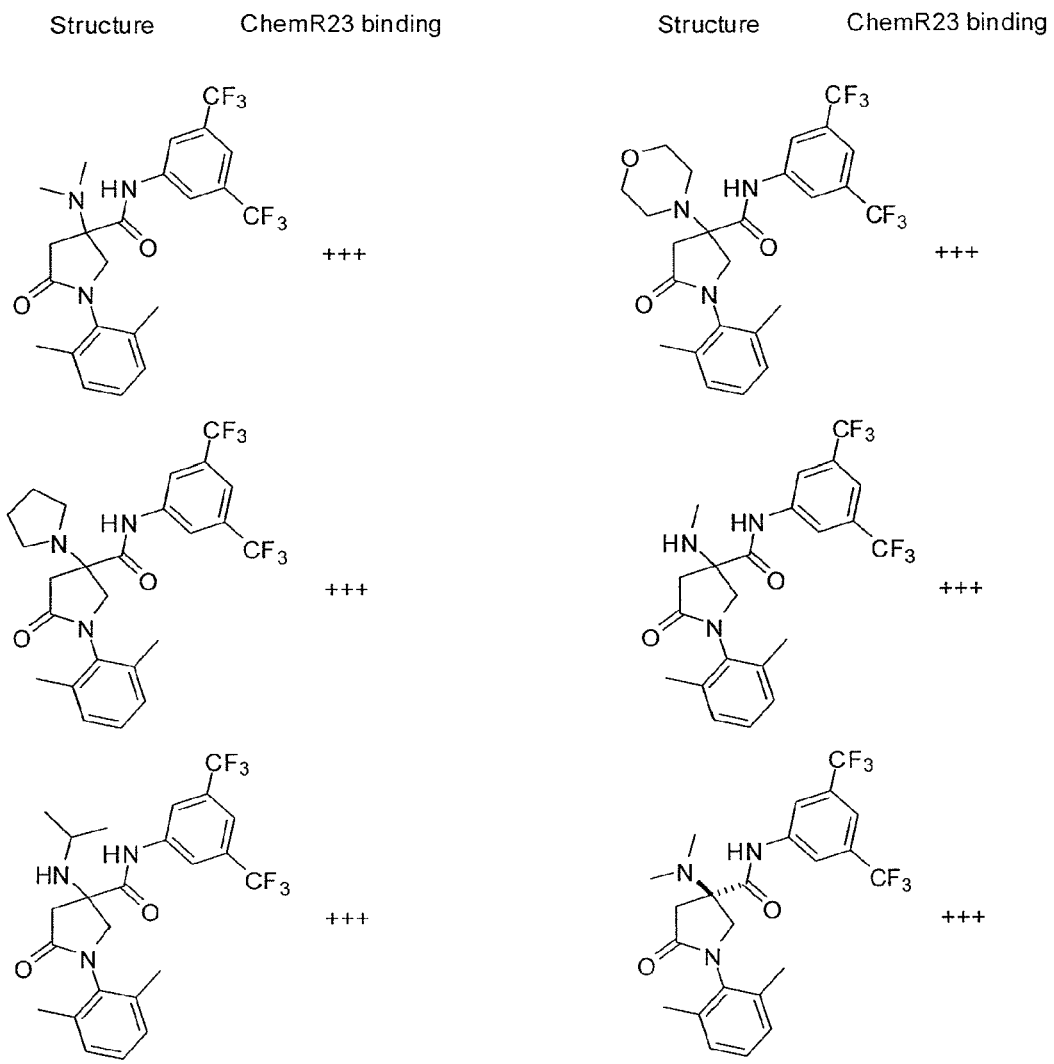
Figure 1X:
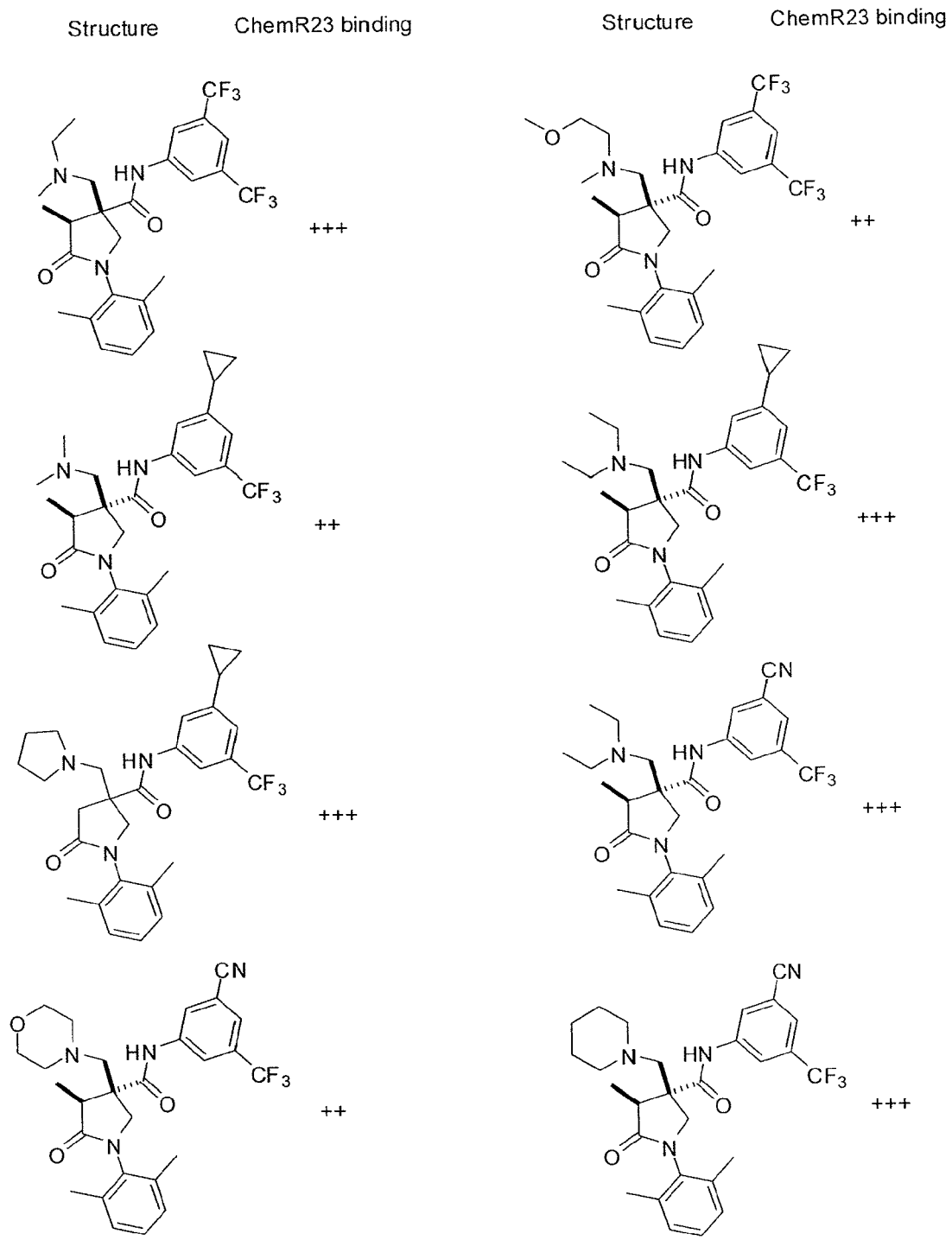
Figure 1Y:
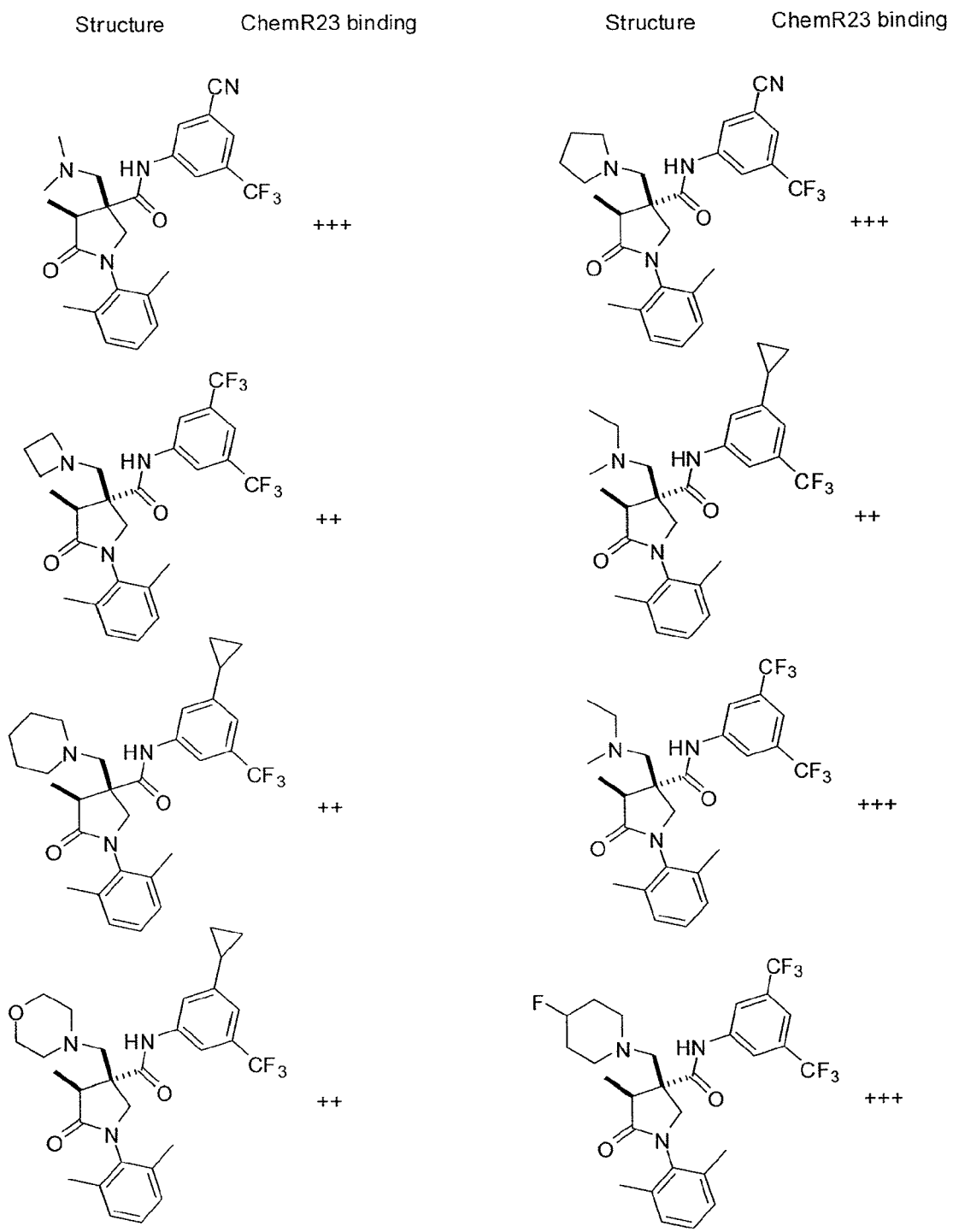
Figure 1Z:
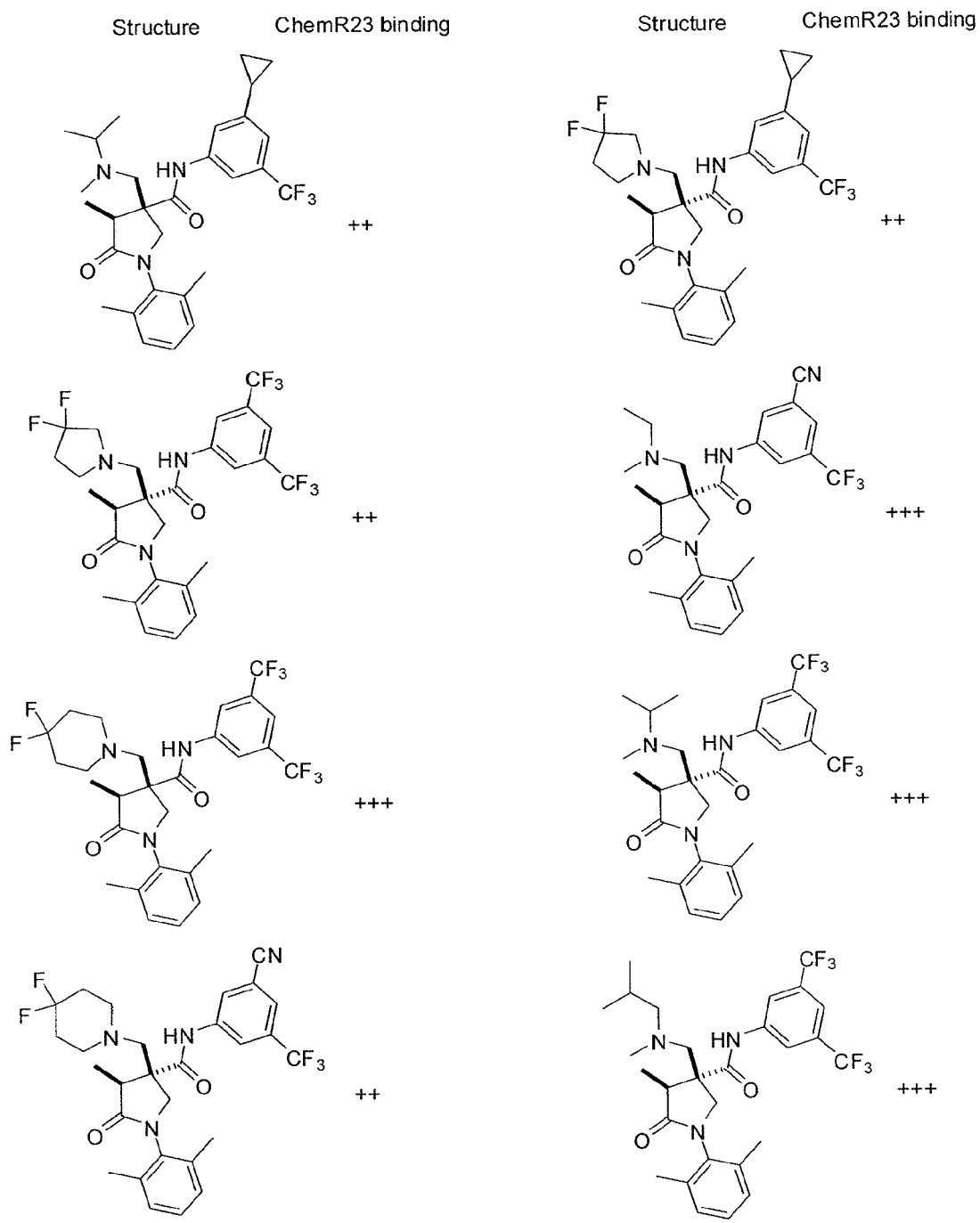
Figure 1A:
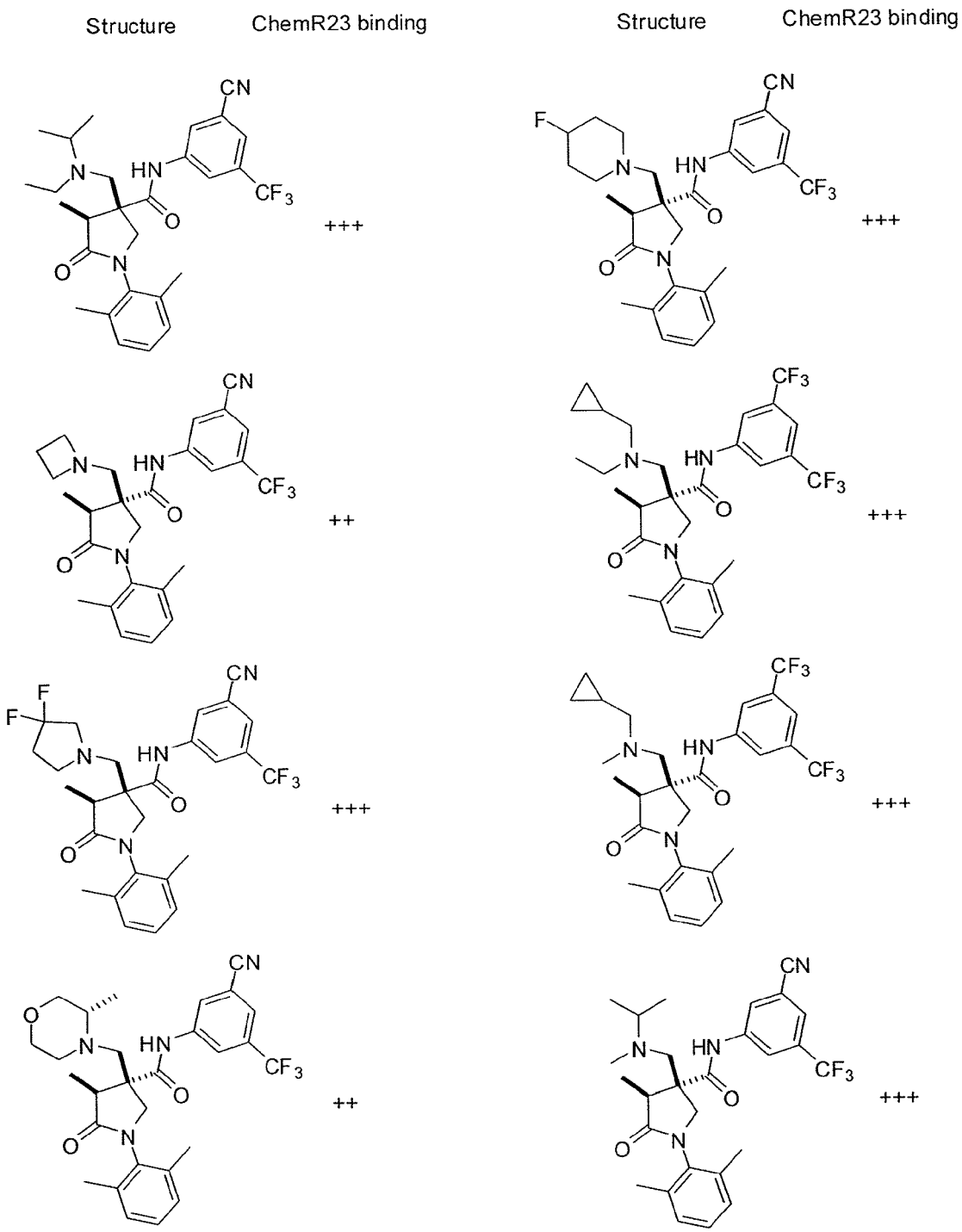
Figure 1B:
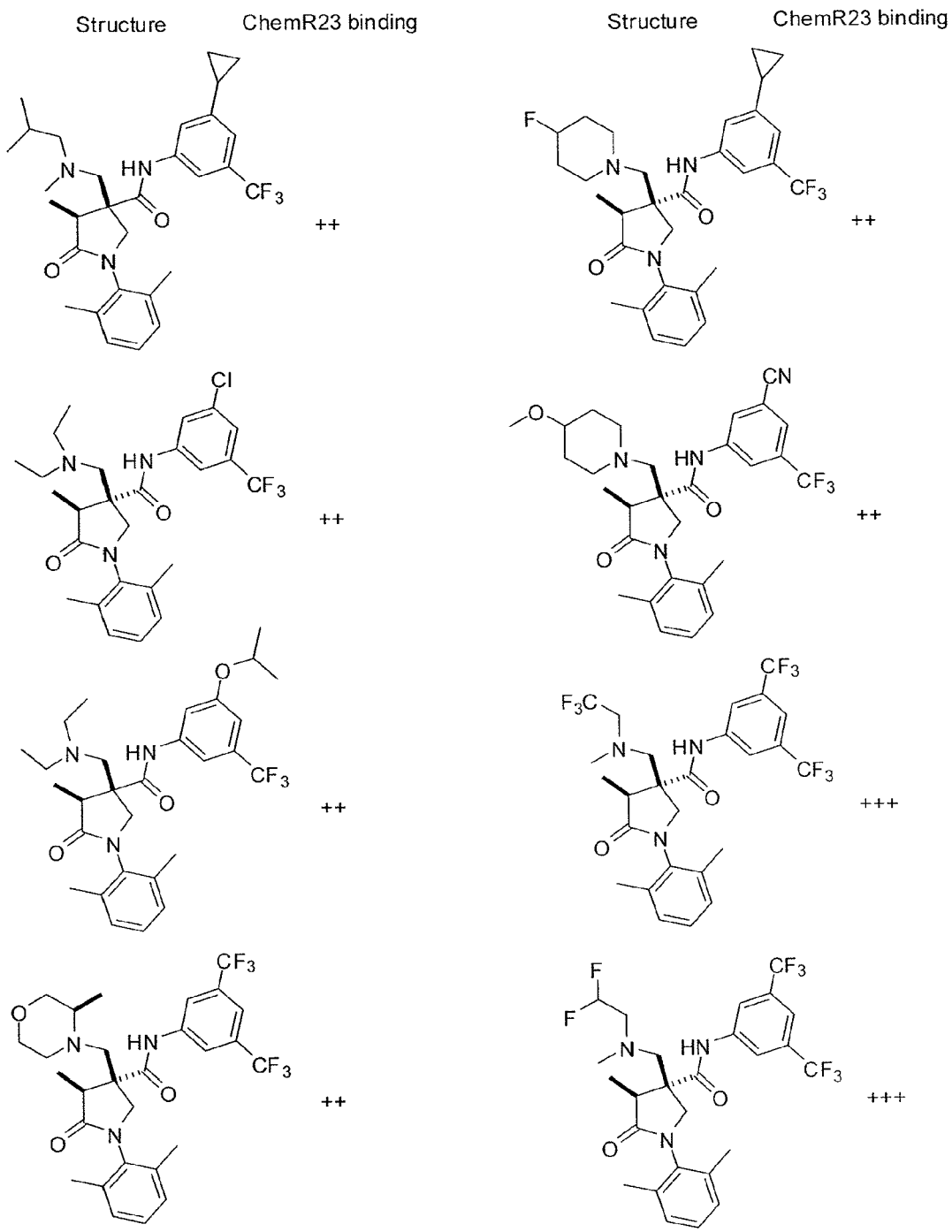
Figure 1C:
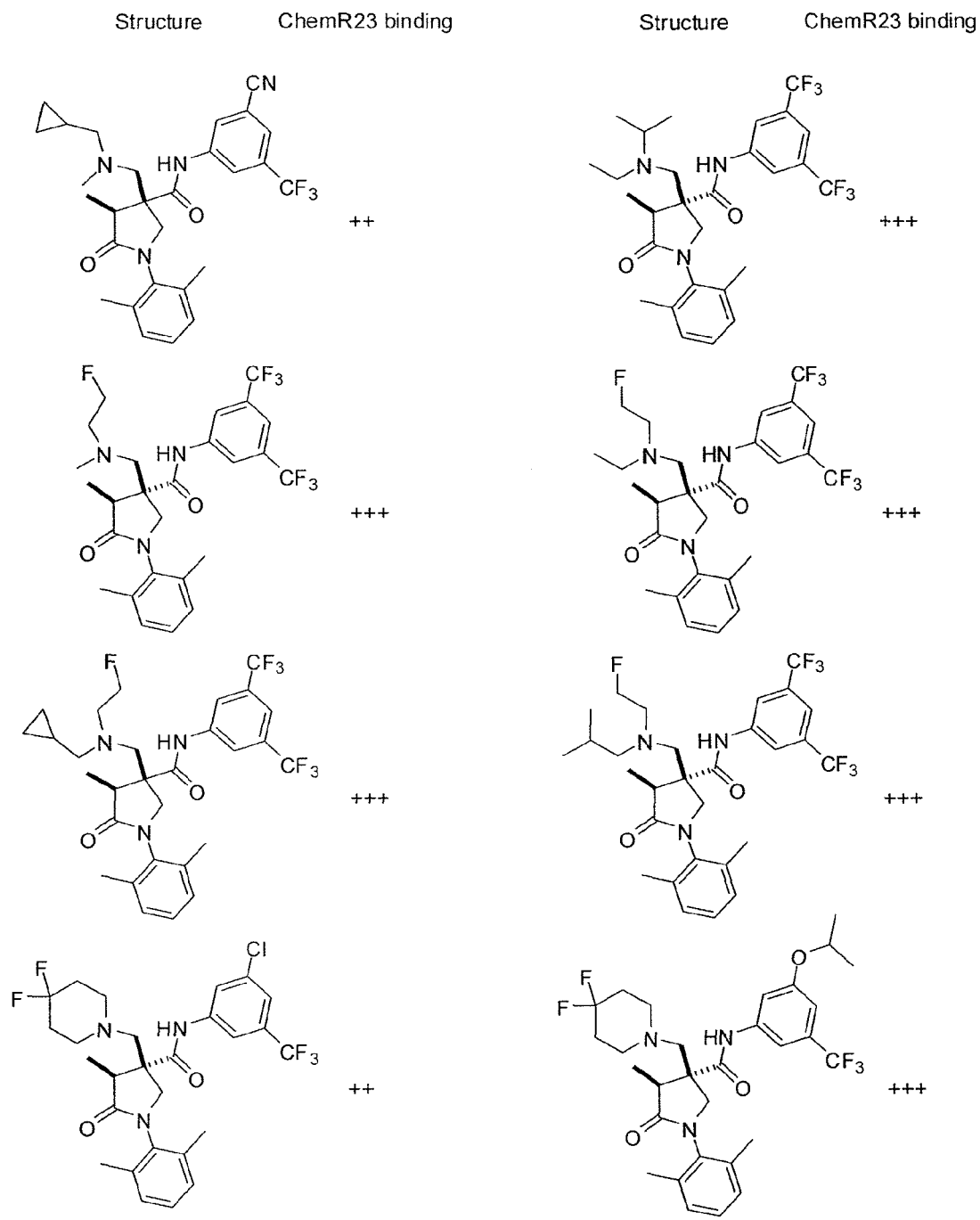
Figure 1D:
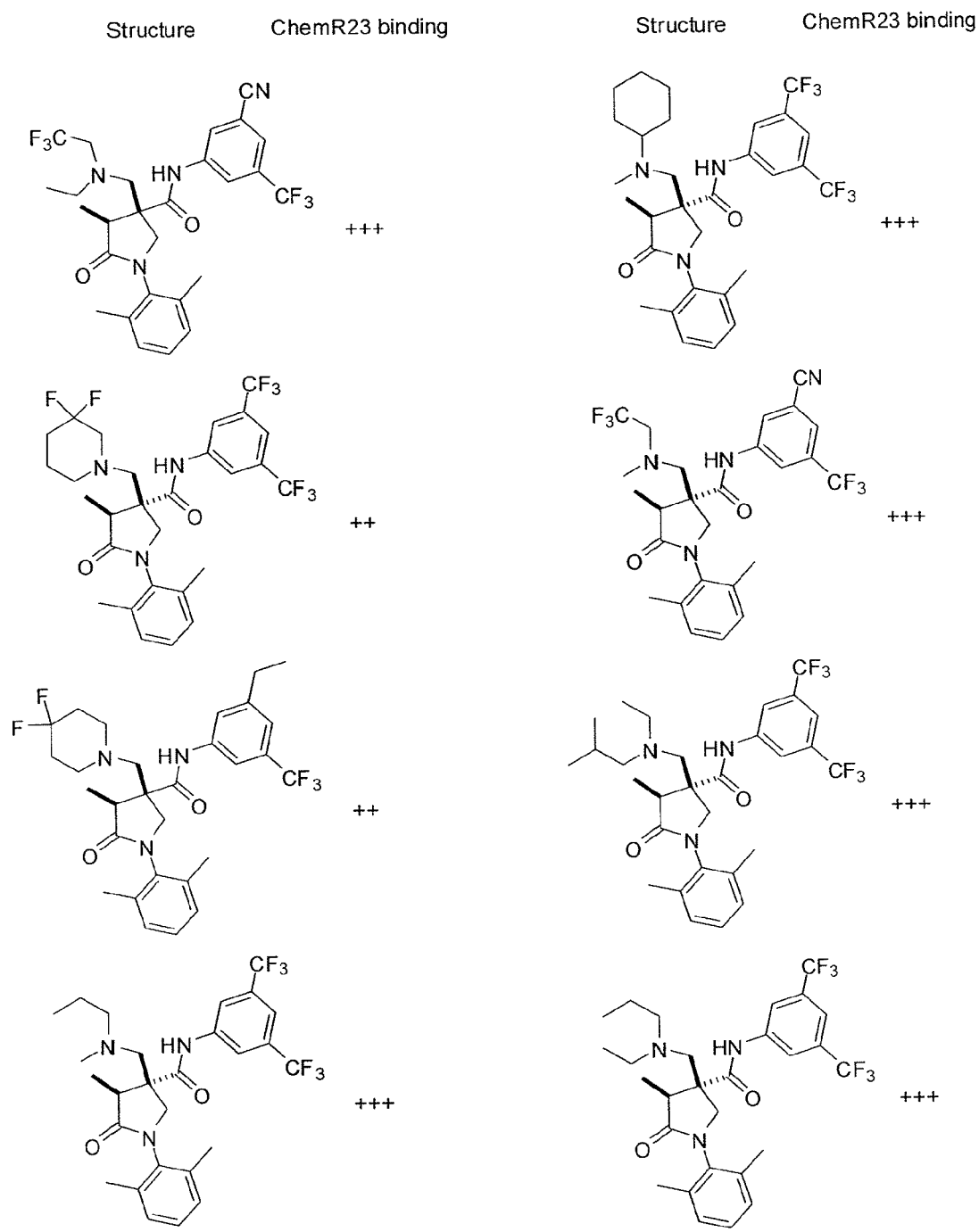
Figure 1E:
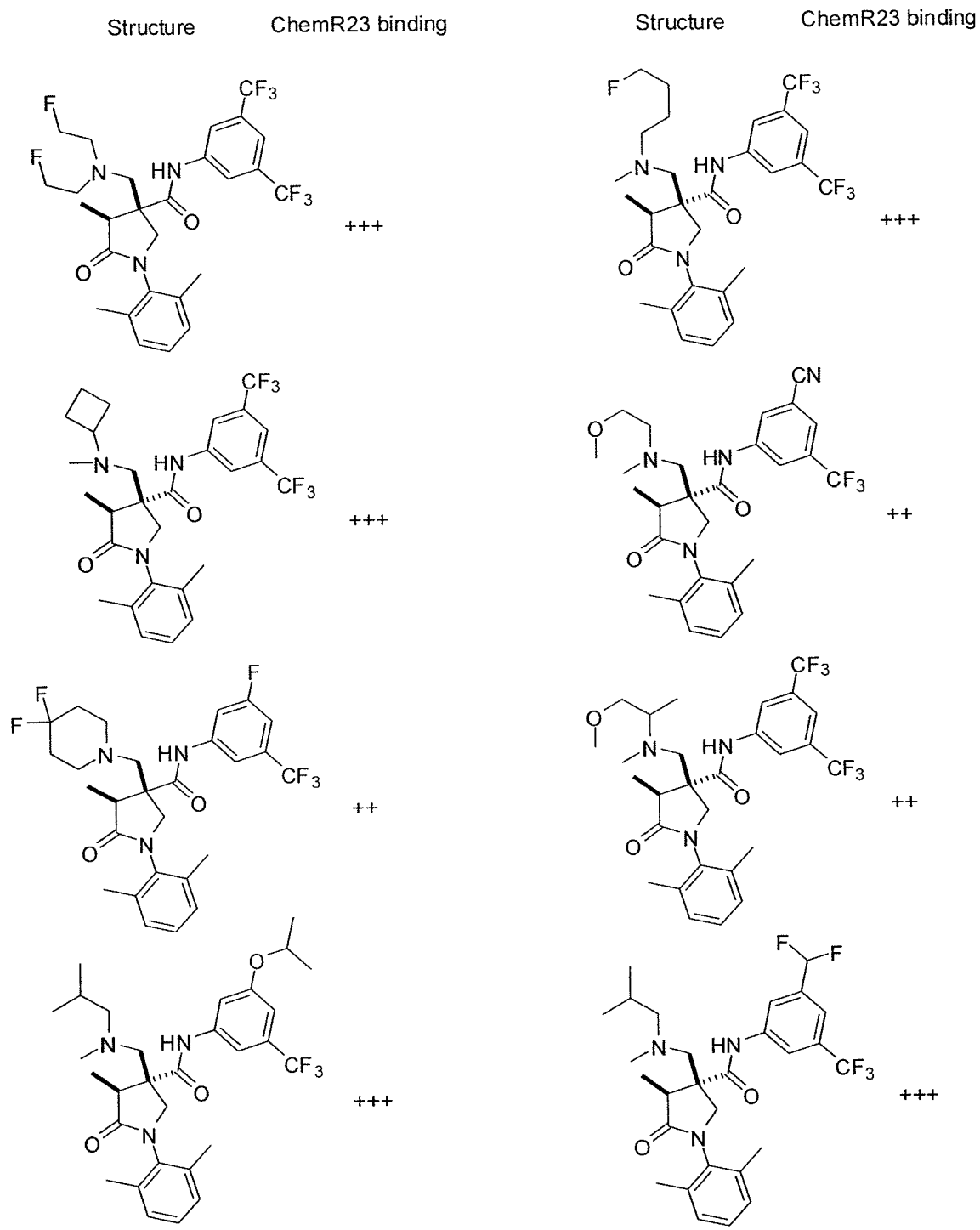
Figure 1F:
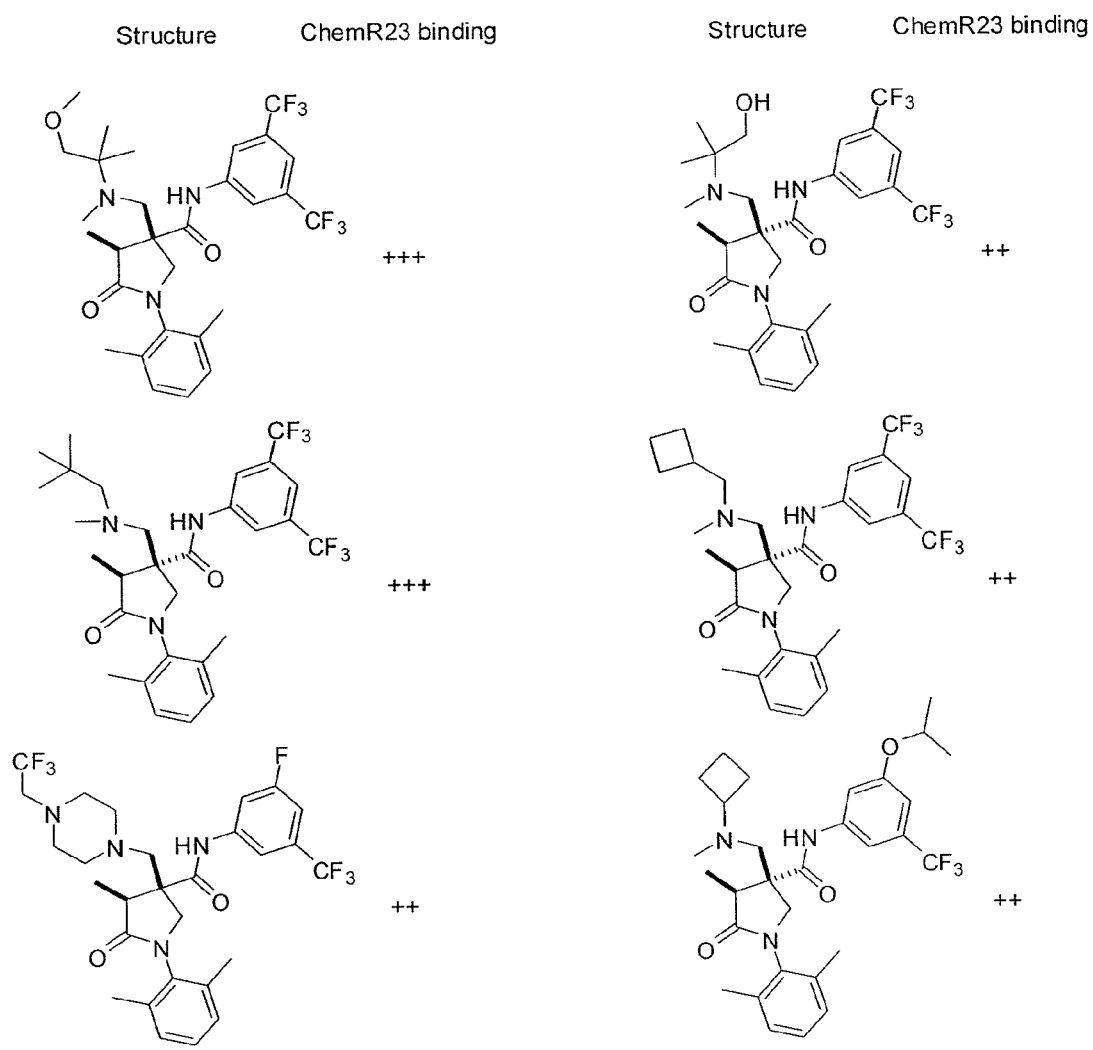

Still other selected embodiments are any of the compounds provided in FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W, 1X, 1Y, 1Z, 1AA, 1BB, 1CC, 1DD, 1EE and 1FF.

Preparation of Compounds

Certain compounds of the invention can be prepared following methodology as described below. Compounds can also be prepared as shown in the synthetic procedures outlined in the Examples section of this document. In addition the syntheses of certain intermediate compounds that are useful in the preparation of compounds of the invention are described below.

Those skilled in the art will recognize that there are a variety of methods available to synthesize molecules represented in the claims. In general, useful methods for synthesizing compounds represented in the claims consist of four parts, which may be done in any order: Formation of the pyrrolidinone ring, installation of the substituents at C3 and C4 of the pyrrolidinone ring, formation of the aniline amide bond, and installation and/or modification of functional groups on the various substituents.

Several methods for the preparation of claimed compounds are illustrated below (eq. 1-7).

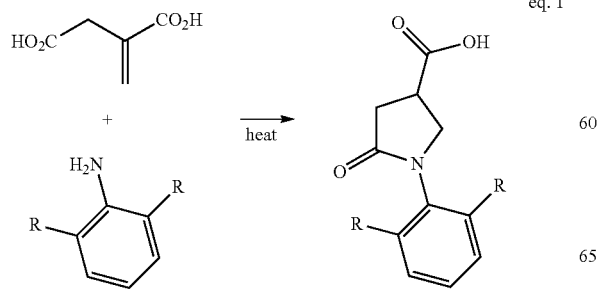

eq. 1

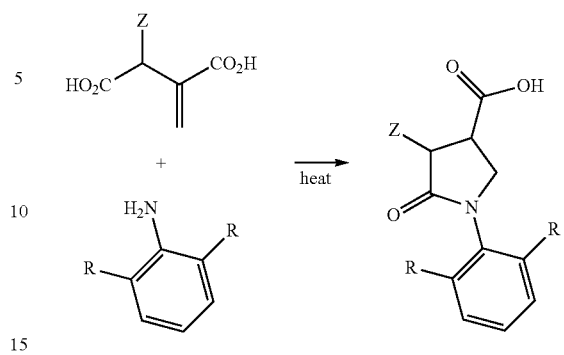

eq. 2

Equations 1-2 demonstrate some methods of forming the pyrrolidinone ring. Equations 3-5 demonstrate methods to introduce substitution into the ring via treatment with base followed by alkylation with suitable electrophiles. Conversion of the ester to the corresponding aniline amide then results in the compounds of the invention (equations 6 and 7).

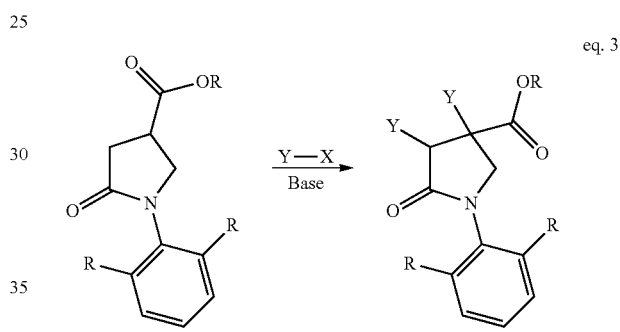

eq. 3

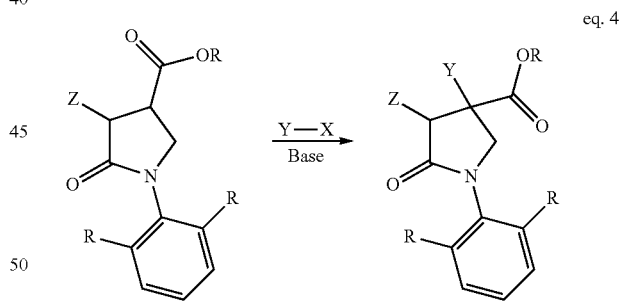

eq. 4

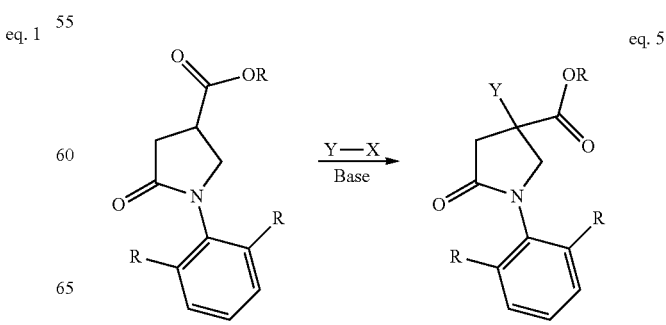

eq. 5

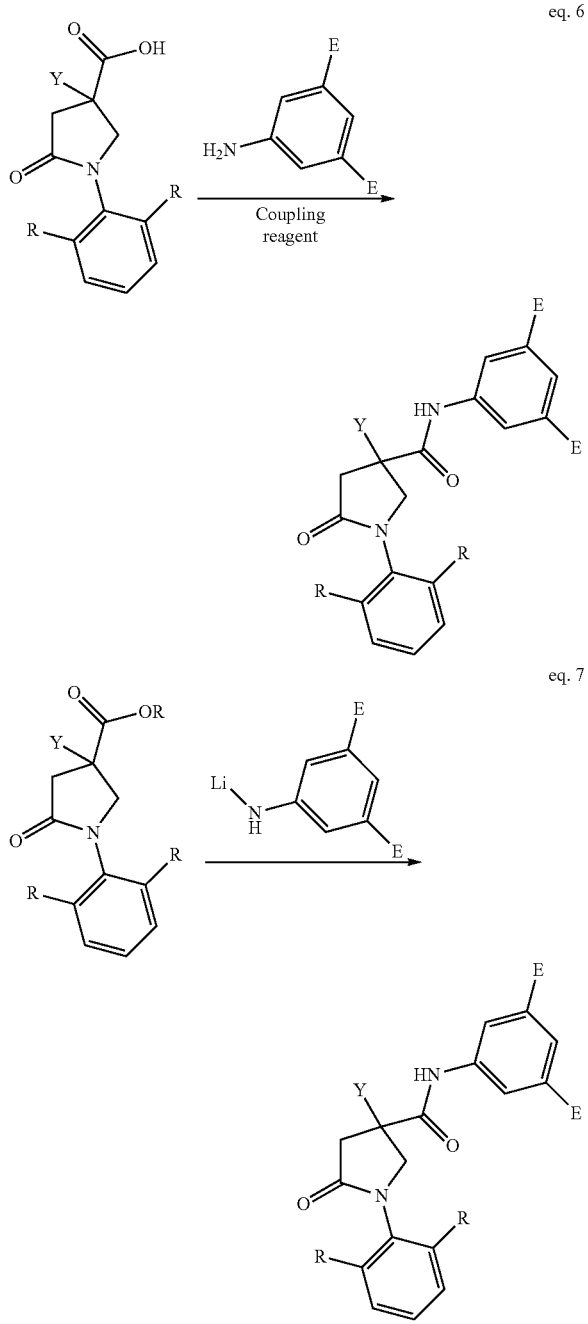

A variety of methods described above have been used to prepare compounds of the invention, some of which are described in the examples.

B. Compositions

In addition to the compounds provided above, compositions for modulating ChemR23 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

C. Methods of Use

While not wishing to be bound by any particular theory, the compounds and compositions of the present invention are considered to provide a therapeutic effect by binding to the ChemR23 receptor. Therefore, the compounds and compositions of the present invention can be used in the treatment or prevention of diseases or disorders in a mammal in which the inhibition of natural ligand binding to the ChemR23 receptor would provide a therapeutic effect.

In one embodiment, a preferred method of inhibiting the binding of the chemokine ligands to a ChemR23 receptor includes contacting one or more of the previously mentioned compounds with a cell that expresses the ChemR23 receptor for a time sufficient to inhibit the binding of the natural chemokine ligands to the ChemR23 receptor.

In some embodiments, the compounds and compositions of the invention are administered to a subject having inflammatory skin disease. In some cases, ChemR23 modulators are administered to treat psoriasis, systemic lupus erythematosus, discoid lupus erythematosus, dermatomyositis, lichen planus, bullous pemphigoid, as well as brain and neuronal dysfunction, such as multiple sclerosis and demyelinating diseases; rheumatoid arthritis; atherosclerosis; type II diabetes, insulin resistance, obesity, metabolic syndrome, dyslipidemia, cardiovascular disease, as well as other disorders and diseases described herein.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with ChemR23 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including psoriasis, dermatomyositis, inflammatory bowel disease, rheumatoid arthritis, osteoarthritis, psoriatic arthritis, polyarticular arthritis, multiple sclerosis, allergic diseases, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IV. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; $Pd_2$ $dba_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 1-(2,6-dimethylphenyl)-3-isopropyl-5-oxo-pyrrolidine-3-carboxylic acid [3,5-bis(trifluoromethyl)phenyl]amide

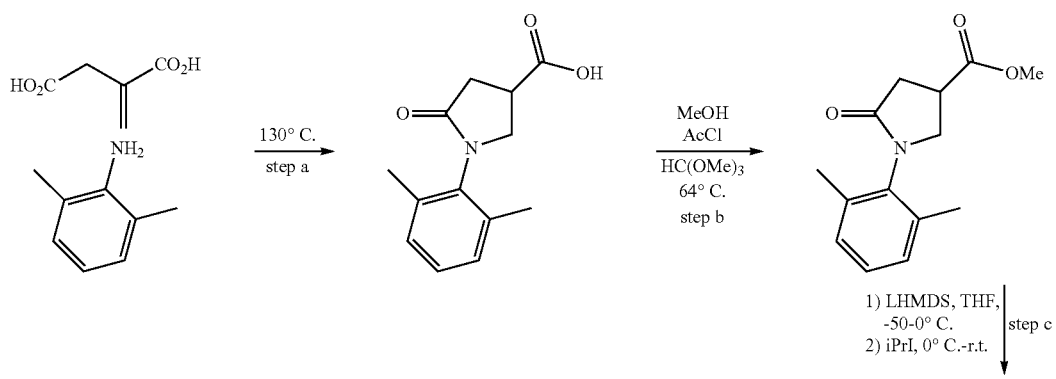

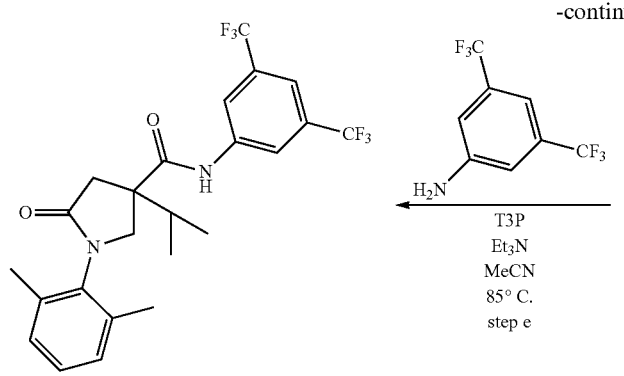
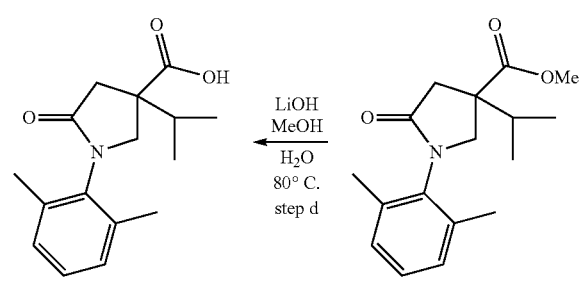

a) A mixture of 2,6-dimethylaniline (121 g, 1 mol) and itaconic acid (130 g, 1 mol) was heated to 130° C. for 45 min in a flask open to the atmosphere, letting the generated steam vent. The heating source was removed and 0.8 L of ethyl acetate was added under vigorous stirring, while the mixture was still hot (allowing initially for some reflux). The mixture was then let to cool to room temperature while stirring. The solids were filtered off, washed with 0.4 L of ethyl acetate and dried in air to give 164 g (70% yield) of colorless crystals. LC-MS $R_t$ (retention time): 0.54 min, MS: (ES) m/z 234 (M+H$^+$).

b) Acetyl chloride (2.40 g, 30.9 mmol) was added dropwise to 400 mL of methanol. 1-(2,6-dimethylphenyl)-5-oxo-pyrrolidine-3-carboxylic acid (144 g, 618 mmol, prepared in step a above) was added to the solution followed by trimethyl orthoformate (67 mL, 618 mmol). The mixture was heated to 64° C. for 1 h and then concentrated in vacuo to give 152 g (99% yield) of pure product as an oil. LC-MS $R_t$ (retention time): 1.49 min, MS: (ES) m/z 248 (M+H$^+$).

c) LHMDS (1.0 M in THF, 15.3 mL, 15.3 mmol) was added to the solution of 1-(2,6-dimethylphenyl)-5-oxo-pyrrolidine-3-carboxylic acid methyl ester (3.44 g, 13.9 mmol) in THF (7 mL) in a reaction flask cooled to −50° C. under nitrogen atmosphere. The reaction mixture was allowed to warm up to 0° C., whereupon 2-iodopropane (2.78 mL, 27.8 mmol) was added. The reaction mixture was allowed to warm up to room temperature and was kept stirring for 2 h. 20 mL of half-saturated aqueous ammonium chloride solution was added, followed by 100 mL of CH$_2$Cl$_2$. The organic layer was concentrated in vacuo on silica gel and purified by flash chromatography (SiO$_2$, 20-60% EtOAc/hexanes) to give 1.65 g of the desired compound (41% yield). LC-MS $R_t$ (retention time): 2.24 min, MS: (ES) m/z 290 (M+H$^+$).

d) Lithium hydroxide (96 mg, 4.00 mmol) was added to a solution of the ester from step c (115 mg, 0.40 mmol) in methanol (1 mL) and water (1 ml) at room temperature. The mixture was heated in a sealed vial to 80° C. for 1 h, at which time the reaction was completed. The organic solvent was removed in vacuo. To the resulting solution 4.0 mL of 1 M aqueous hydrochloric acid was added and the mixture was stirred at room temperature for 15 minutes. The white solids were filtered off, washed with additional 5 mL of water and vacuum-dried to give 93 mg of the product (85% yield). LC-MS: $R_t$ (retention time): 1.74 min, MS: (ES) m/z 276 (M+H$^+$).

e) 3,5-Bis(trifluoromethyl)aniline (42.0 mg, 0.185 mmol) was added to a solution of the acid prepared above (51.0 mg, 0.185 mmol) and triethylamine (6 equiv.) in acetonitrile (1 mL). T3P (50% solution, 235 mg, 0.370 mmol) was then added and the solution was allowed to stir at 85° C. for 16 h. The reaction mixture was concentrated in vacuo and redissolved in CH$_2$Cl$_2$. The solution was concentrated in vacuo on silica gel and purified by flash chromatography (SiO$_2$, 20-80% EtOAc/hexanes) to give 7.0 mg of the desired compound (8% yield) as a white solid. $^1$H NMR (400 MHz, DMSO-d$_6$) δ 0.96 (d, J=6.8, 3H), 0.97 (d, J=6.8, 3H), 1.98 (s, 3H), 2.16 (s, 3H), 2.38 (qq, J=6.8, 6.8, 1H), 2.69 (d, J=17.2, 1H), 3.05 (d, J=17.2, 1H), 3.67 (d, J=10.8, 1H), 3.98 (d, J=10.8, 1H), 7.03-7.15 (m, 3H), 7.80 (s, 1H), 8.35 (s, 2H), 10.31 (s, 1H). LC-MS: $R_t$ (retention time)=2.94 min, MS: (ES) m/z 487 (M+H$^+$).

Example 2

Synthesis of (3R)-1-(2,6-dimethylphenyl)-3-isopropyl-5-oxo-pyrrolidine-3-carboxylic acid [3,5-bis(trifluoromethyl)phenyl]amide

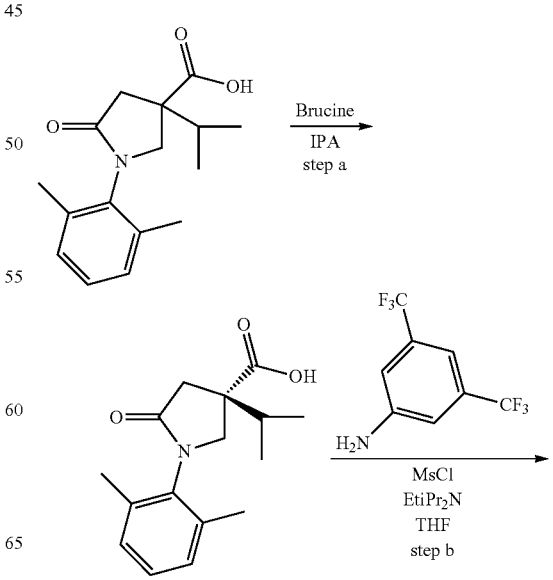

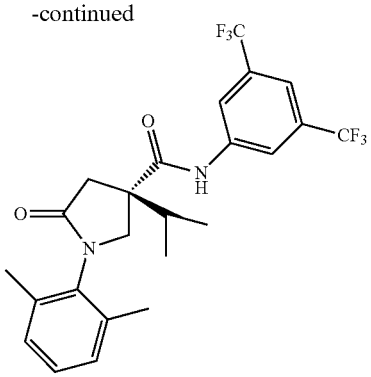

a) A mixture of 1-(2,6-dimethylphenyl)-3-isopropyl-5-oxo-pyrrolidine-3-carboxylic acid (prepared as in example 1 step d, 2.47 g, 8.97 mmol) and brucine (3.98 g, 10.09 mmol) in IPA (20 mL) was heated to 80° C. until the solution became clear. The solution was let cool to room temperature and seeded with diastereopure crystals, then it was let to stand at room temperature for 6 days, followed by cooling down to 0° C. and aging for another 4 h. The crystals were filtered off at 0° C., washed with cold IPA into a separate flask and saved as seeds for future batches. The mother liquor (not containing the washes) was diluted with 40 mL of 1 M aqueous hydrochloric acid and 40 mL of diethyl ether and stirred vigorously for 15 minutes. Subsequent phase separation gave an organic layer, which was dried over anhydrous magnesium sulfate, filtered and concentrated in vacuo to give 1.20 g of enantioenriched acid (ee=76.2%). The solid was recrystallized from a mixture of hot toluene (25 mL) and dioxane (3 mL) to give 0.90 g of further enriched acid (ee=97.3%). Recrystallization was repeated two more times to obtain 0.75 g of enantiopure (ee>99.8%) acid (30% yield) as colorless crystals. LC-MS $R_t$ (retention time): 1.86 min, MS: (ES) m/z 276 (M+H$^+$).

b) Methanesulfonyl chloride (167 mg, 1.45 mmol) was added dropwise to a solution of enantiopure (3R)-1-(2,6-dimethylphenyl)-3-isopropyl-5-oxo-pyrrolidine-3-carboxylic acid (182 mg, 0.661 mmol, prepared in step a above), N,N-diisopropylethylamine (374 mg, 2.90 mmol) and 3,5-bis(trifluoromethyl)aniline (331 mg, 1.45 mmol) in THF (4 mL). Stirring at room temperature for 1 h allowed the reaction to reach completion, whereupon 5 mL of 0.3 M aqueous hydrochloric acid and 10 mL of DCM were added and the mixture was stirred vigorously for 5 min. The separated organic phase was concentrated in vacuo on silica gel and purified by flash chromatography (SiO$_2$, 25-60% EtOAc/hexanes) to give an off-white residue, which was recrystallized from a mixture of hot ethyl acetate (2 mL) and hexanes (7 mL) to give 203 mg of the desired compound (63% yield) as colorless crystals. $^1$H NMR (400 MHz, CDCl$_3$) δ 1.09 (d, J=7.4, 3H), 1.11 (d, J=7.4, 3H), 2.13 (s, 3H), 2.23 (s, 3H), 2.26 (qq, J=7.4, 7.4, 1H), 2.81 (d, J=17.2, 1H), 3.09 (d, J=17.2, 1H), 3.61 (d, J=10.4, 1H), 4.17 (d, J=10.4, 1H), 7.02-7.18 (m, 3H), 7.64 (s, 1H), 7.86 (s, 1H), 8.05 (s, 2H). LC-MS: $R_t$ (retention time)= 3.10 min, MS: (ES) m/z 487 (M+H$^+$).

Example 3

Synthesis of 1-(2,6-dimethylphenyl)-3-methyl-5-oxo-pyrrolidine-3-carboxylic acid [3,5-bis(trifluoromethyl)phenyl]amide

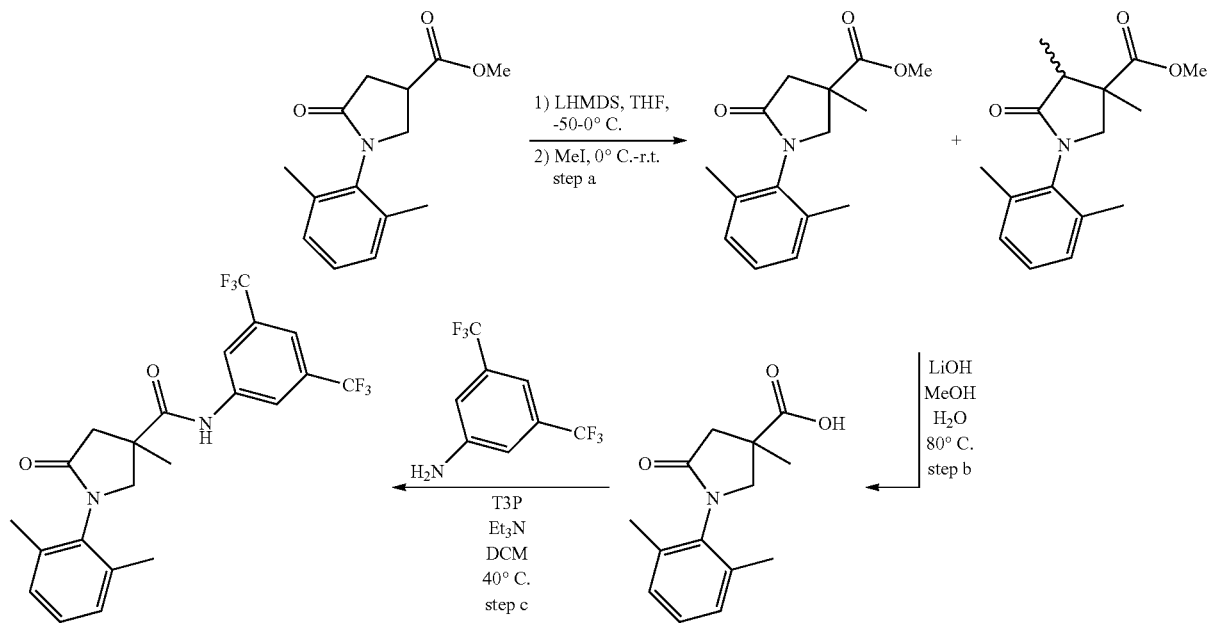

a) LHMDS (1.0 M in THF, 26.9 mL, 26.9 mmol) was added to the solution of 1-(2,6-dimethylphenyl)-5-oxo-pyrrolidine-3-carboxylic acid methyl ester (5.53 mg, 22.4 mmol, prepared in example 1 step b in THF (20 mL) in a reaction flask cooled to −50° C. under nitrogen atmosphere. The reaction mixture was allowed to warm up to 0° C., and then cooled to −20° C., whereupon iodomethane (7.0 mL, 5 equiv.) was added. The reaction mixture was allowed to warm up to room temperature and was kept stirring for 15 min. 50 mL of half-saturated aqueous ammonium chloride solution was added and the mixture was extracted with two 50 mL portions of CH$_2$Cl$_2$. The combined organic layers were concentrated in vacuo on silica gel and purified by flash chromatography ($SiO_2$, 30-100% EtOAc/hexanes) to give 4.00 g of the desired compound (68% yield). LC-MS $R_t$ (retention time): 1.87 min, MS: (ES) m/z 262 (M+H$^+$).

As a minor product 0.54 g of a mixture of diastereoisomeric 1-(2,6-dimethylphenyl)-3,4-dimethyl-5-oxo-pyrrolidine-3-carboxylic acid methyl esters was isolated (8.8% yield). LC-MS $R_t$ (retention time): 2.10 min, MS: (ES) m/z 276 (M+H$^+$).

Examples 4 and 5

Synthesis of (3S*,4S*)-1-(2,6-dimethylphenyl)-4-methyl-5-oxo-pyrrolidine-3-carboxylic acid [3,5-bis(trifluoromethyl)phenyl]amide and (3S*,4R*)-1-(2,6-dimethylphenyl)-4-methyl-5-oxo-pyrrolidine-3-carboxylic acid [3,5-bis(trifluoromethyl)phenyl]amide

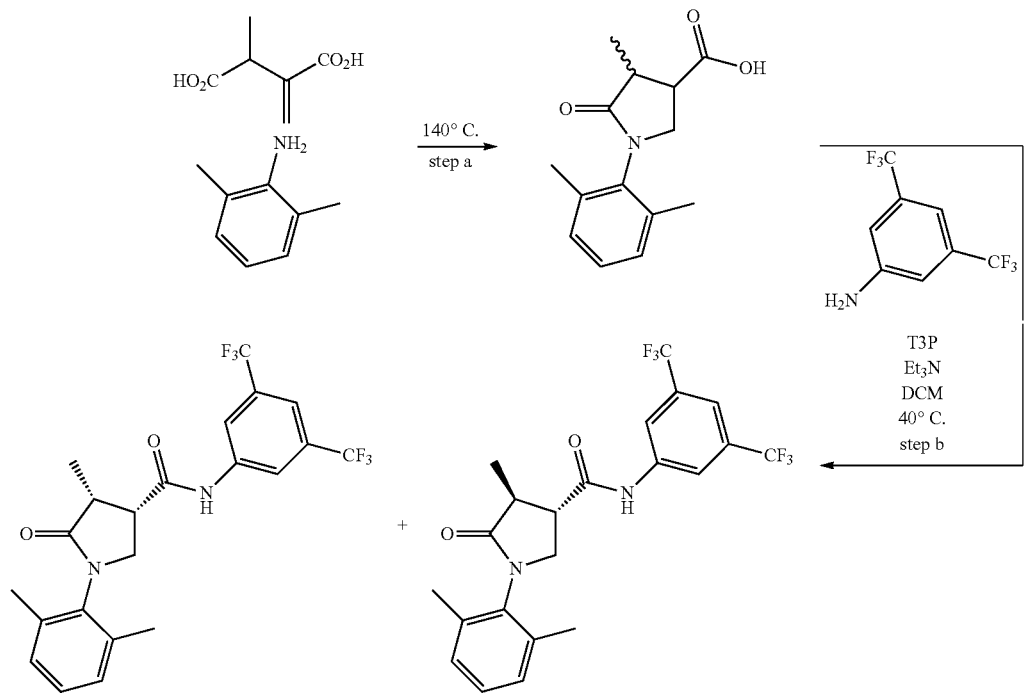

b) Lithium hydroxide (81 mg, 3.38 mmol) was added to a solution of the ester from step a (146 mg, 0.56 mmol) in methanol (1 mL) and water (1 ml) at room temperature. The mixture was heated in a sealed vial to 80° C. for 30 min, at which time the reaction was completed. The organic solvent was removed in vacuo. To the resulting solution 0.28 mL of 12 M aqueous hydrochloric acid was added and the mixture was stirred at room temperature for 15 minutes. The white solids were filtered off, washed with additional 5 mL of water and vacuum-dried to give 120 mg of the product (87% yield). LC-MS: $R_t$ (retention time): 0.92 min, MS: (ES) m/z 248 (M+H$^+$).

c) 3,5-Bis(trifluoromethyl)aniline (56.0 mg, 0.243 mmol) was added to a solution of the acid prepared above (60.0 mg, 0.243 mmol) and triethylamine (6 equiv.) in $CH_2Cl_2$ (1 mL). T3P (50% solution, 309 mg, 0.486 mmol) was then added and the solution was allowed to stir at 40° C. for 16 h. The solution was concentrated in vacuo on silica gel and purified by flash chromatography ($SiO_2$, 30-100% EtOAc/hexanes) to give an off-white residue, which was recrystallized from a mixture of hot ethyl acetate (2 mL) and hexanes (2 mL) to give 37 mg of the desired compound (33% yield) as colorless crystals. $^1$H NMR (400 MHz, DMSO-$d_6$) δ □ 1.63 (s, 3H), 2.04 (s, 3H), 2.18 (s, 3H), 2.49 (d, J=16.4, 1H), 3.12 (d, J=16.4, 1H), 3.48 (d, J=10.2, 1H), 4.02 (d, J=10.2, 1H), 7.05-7.18 (m, 3H), 7.79 (s, 1H), 8.35 (s, 2H), 10.22 (s, 1H). LC-MS: $R_t$ (retention time)=2.78 min, MS: (ES) m/z 459 (M+H$^+$).

a) A mixture of 2,6-dimethylaniline (426 mg, 3.52 mmol) and β-methylitaconic acid (507 mg, 3.52 mmol, prepared according to a procedure described by Leitner et al, *J. Am. Chem. Soc.* 1993, 115, 152-159) was heated to 140° C. for 1 h in a flask open to the atmosphere, letting the generated steam vent. The heating source was removed and 3 mL of ethyl acetate was added under vigorous stirring, while the mixture was still hot (allowing initially for some reflux). The mixture was then let to cool to room temperature while stirring. The solution was concentrated in vacuo on silica gel and purified by flash chromatography ($SiO_2$, 50-100% EtOAc/hexanes) to give 410 mg of the desired compound (47% yield) as a white solid. LC-MS $R_t$ (retention time): 0.84 min, MS: (ES) m/z 248 (M+H$^+$).

b) 3,5-Bis(trifluoromethyl)aniline (66.0 mg, 0.287 mmol) was added to a solution of the acid prepared in step a above (71.0 mg, 0.287 mmol) and triethylamine (6 equiv.) in DCM (1 mL). T3P (50% solution, 365 mg, 0.574 mmol) was then added and the solution was allowed to stir at 40° C. for 16 h. The solution was concentrated in vacuo on silica gel and purified by flash chromatography ($SiO_2$, 30-100% EtOAc/hexanes) to give 40 mg of the first-eluting isomer, (3S*,4S*), (31% yield) as a white solid. $^1$H NMR (400 MHz, DMSO-$d_6$) δ □ 1.27 (d, J=7.6, 3H), 2.14 (s, 3H), 2.15 (s, 3H), 2.82-2.91 (m, 1H), 3.14-3.23 (m, 1H), 3.64-3.78 (m, 2H), 7.08-7.19 (m, 3H), 7.79 (s, 1H), 8.29 (s, 2H), 10.83 (s, 1H). LC-MS: $R_t$ (retention time)=2.79 min, MS: (ES) m/z 459 (M+H$^+$)

The second-eluting isomer, (3S*,4R*), was obtained in 15% yield (19 mg) as a white solid. $^1$H NMR (400 MHz, DMSO-d$_6$) δ □ 11.13 (d, J=7.2, 3H), 2.13 (s, 3H), 2.23 (s, 3H), 3.00-3.09 (m, 1H), 3.57-3.65 (m, 1H), 3.65-3.73 (m, 1H), 3.73-3.79 (m, 1H), 7.07-7.18 (m, 3H), 7.78 (s, 1H), 8.27 (s, 2H), 10.81 (s, 1H). LC-MS: R$_t$ (retention time)=2.80 min, MS: (ES) m/z 459 (M+H$^+$).

Example 6

Synthesis of (3aR*,6aS*)-5-(2,6-dimethylphenyl)-6-oxohexahydrofuro[2,3-c]pyrrole-3a-carboxylic acid [3,5-bis(trifluoromethyl)phenyl]amide

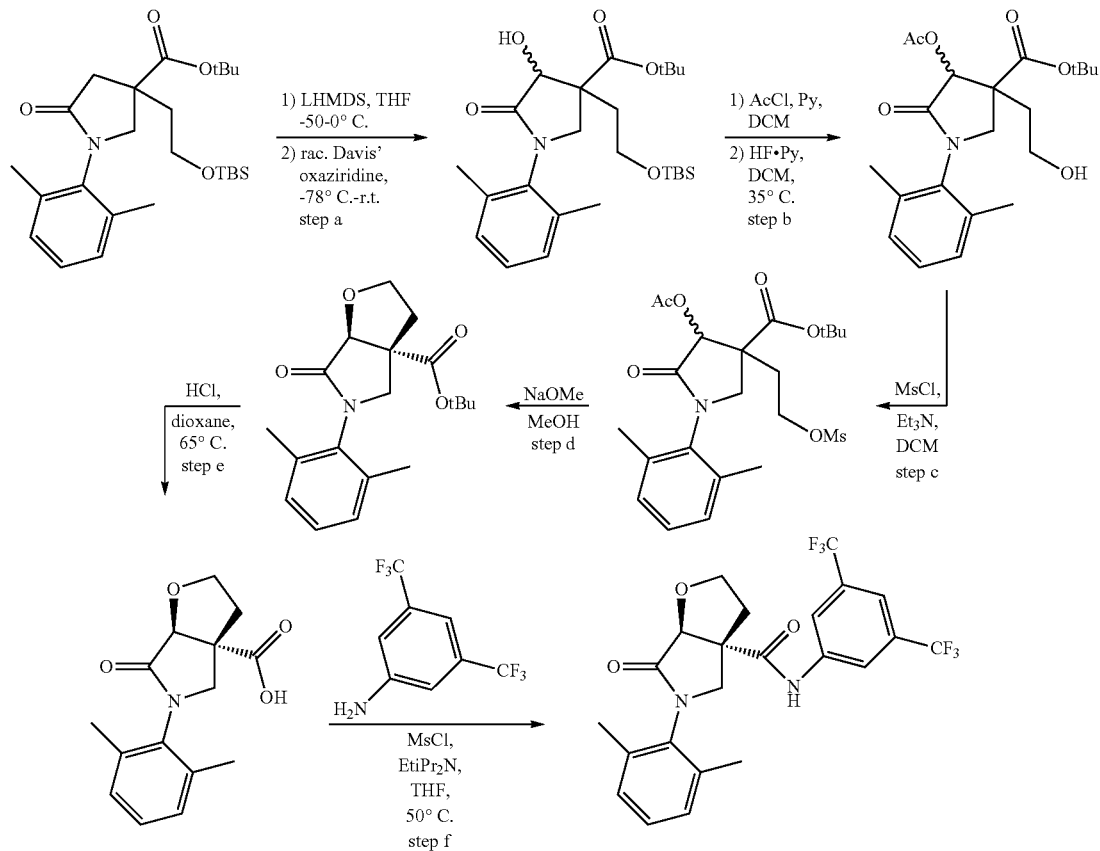

a) LHMDS (1.0 M in THF, 4.54 mL, 4.54 mmol) was added to the solution of 3-[2-(tert-butyldimethylsilanyloxy)ethyl]-1-(2,6-dimethylphenyl)-5-oxo-pyrrolidine-3-carboxylic acid tert-butyl ester (prepared in example 6 step a, 1.69 g, 3.78 mmol) in THF (2 mL) in a reaction flask cooled to −50° C. under nitrogen atmosphere. The reaction mixture was allowed to warm up to 0° C., then immediately cooled to −78° C., whereupon a solution of (±)-(camphorylsulfonyl)-oxaziridine (1.27 g, 5.56 mmol) in THF (6 mL) was added dropwise. The reaction mixture was allowed to warm up to room temperature and was kept stirring for 1 h. 20 mL of half-saturated aqueous ammonium chloride solution was added, followed by 100 mL of hexanes. The organic layer was concentrated in vacuo on silica gel and purified by flash chromatography (SiO$_2$, 5-50% EtOAc/hexanes) to give 1.46 g of a residue. That solid was redissolved in 30 mL of hexanes. The suspension was filtered and the solid was discarded. The filtrate was concentrated in vacuo to give 1.38 g of the desired compound (79% yield, 80:20 mixture of diastereoisomers observed by $^1$H NMR). LC-MS R$_t$ (retention time): 3.23 min, MS: (ES) m/z 464 (M+H$^+$).

b) Acetyl chloride (334 μL, 4.68 mmol) was added dropwise to a solution containing the alcohol prepared in step a above (1.38 g, 2.98 mmol) and pyridine (721 μL, 8.94 mmol) in CH$_2$Cl$_2$ (10 mL) in a polypropylene vial. The solution was allowed to react for 30 minutes, whereupon hydrogen fluoride-pyridine complex (70 wt % HF, 300 μL, 11.9 mmol) was added at room temperature. The mixture was heated to 35° C. for 3 h. The solution was concentrated in vacuo on silica gel and purified by flash chromatography (SiO$_2$, 30-80% EtOAc/hexanes) to give 909 mg of the desired compound (78% yield). LC-MS: R$_t$ (retention time): 2.05, 2.21 min (80:20 mixture of diastereoisomers), MS: (ES) m/z 392 (M+H$^+$).

c) Methanesulfonyl chloride (234 μL, 3.00 mmol) was added dropwise to a solution of the alcohol prepared in step b above (905 mg, 2.31 mmol) and triethylamine (451 μL, 4.17 mmol) in CH$_2$Cl$_2$ (4 mL). The solution was aged at room temperature for 10 minutes, concentrated in vacuo on silica gel and purified by flash chromatography (SiO$_2$, 30-80% EtOAc/hexanes) to give 912 mg of the desired compound (84% yield). LC-MS R$_t$ (retention time): 2.37 min, MS: (ES) m/z 470 (M+H$^+$).

d) Sodium hydride (60%, 28 mg, 0.704 mmol) was added to the solution of the mesylate prepared in step c above (300 mg, 0.640 mmol) in methanol (15 mL). The reaction mixture was aged at room temperature for 2 h, whereupon acetic acid (45 mg, 0.75 mmol) was added. The mixture was concentrated in vacuo on silica gel and purified by flash chromatography (SiO$_2$, 20-80% EtOAc/hexanes) to give 142 mg of the desired compound (67% yield). LC-MS R$_t$ (retention time): 2.28 min, MS: (ES) m/z 332 (M+H$^+$).

e) The bicyclic compound prepared in step d (71 mg, 0.215 mmol) was dissolved in a 4 N solution of hydrogen chloride in dioxane (2 mL). The resulting solution was heated to 65° C. for 5 h in a sealed vessel, followed by concentration in vacuo to give 59 mg of the carboxylic acid. LC-MS $R_t$ (retention time): 0.58 min, MS: (ES) m/z 276 (M+H$^+$).

f) Methanesulfonyl chloride (49 mg, 0.428 mmol) was added dropwise to a solution of the carboxylic acid prepared in step e above (59 mg, 0.215 mmol), N,N-diisopropylethylamine (139 mg, 1.08 mmol) and 3,5-bis(trifluoromethyl)aniline (98 mg, 0.428 mmol) in THF (0.5 mL). Stirring at 50° C. for 1 h allowed the reaction to reach completion. 4 mL of water and 8 mL of CH$_2$Cl$_2$ were added and the mixture was stirred vigorously for 5 min. The separated organic phase was concentrated in vacuo on silica gel and purified twice by flash chromatography (SiO$_2$, 20-80% EtOAc/hexanes) to give 60 mg of the desired compound (57% yield) as a white solid. $^1$H NMR (400 MHz, DMSO-d$_6$) δ ☐ 2.10 (s, 3H), 2.18 (s, 3H), 2.38-2.48 (m, 1H), 2.57-2.67 (m, 1H), 3.70 (d, J=11.0, 1H), 3.82-3.90 (m, 1H), 4.08 (d, J=11.0, 1H), 4.08-4.16 (m, 1H), 4.98 (s, 1H), 7.08-7.20 (m, 3H), 7.80 (s, 1H), 8.34 (s, 2H), 10.36 (s, 1H). LC-MS: $R_t$ (retention time)=2.66 min, MS: (ES) m/z 487 (M+H$^+$).

Example 7 and 8

Synthesis of (3S*,4S*)-1-(2,6-dimethylphenyl)-3,4-dimethyl-5-oxo-pyrrolidine-3-carboxylic acid [3,5-bis(trifluoromethyl)phenyl]amide and (3S*,4R*)-1-(2,6-dimethylphenyl)-3,4-dimethyl-5-oxo-pyrrolidine-3-carboxylic acid [3,5-bis (trifluoromethyl)phenyl]amide a) Lithium hydroxide (283 mg, 11.8 mmol) was added to a solution of a diastereoisomeric mixture of 1-(2,6-dimethylphenyl)-3,4-dimethyl-5-oxo-pyrrolidine-3-carboxylic acid methyl esters, prepared in example 3 step a (540 mg, 1.96 mmol) in methanol (5 mL) and water (5 ml) at room temperature. The mixture was heated to 50° C. for 2 h, at which time the reaction was completed. The organic solvent was removed in vacuo. To the resulting solution 11.8 mL of 1 M aqueous hydrochloric acid was added and the mixture was stirred at room temperature for 1 hour. The white solids were filtered off, washed with additional 10 mL of water and vacuum-dried to give 480 mg of the product (94% yield). LC-MS: $R_t$ (retention time): 1.32 min, MS: (ES) m/z 262 (M+H$^+$).

b) Methanesulfonyl chloride (328 mg, 2.86 mmol) was added dropwise to a solution of the carboxylic acid prepared in step a above (311 mg, 1.19 mmol), N,N-diisopropylethylamine (738 mg, 5.72 mmol) and 3,5-bis(trifluoromethyl)aniline (654 mg, 2.86 mmol) in THF (1.5 mL). Stirring at 75° C. for 2 h allowed the reaction to reach completion. 5 mL of water and 10 mL of CH$_2$Cl$_2$ were added and the mixture was stirred vigorously for 5 min. The separated organic phase was concentrated in vacuo on silica gel and purified by flash chromatography (SiO$_2$, 25-80% EtOAc/hexanes) to give of the first-eluting isomer. It was recrystallized from hot ethyl acetate (2 mL) and hexanes (2 mL) to give 82 mg (15% yield) of a white solid (3S*,4S*). $^1$H NMR (400 MHz, DMSO-d$_6$) δ ☐ 1.18 (d, J=7.6, 3H), 1.51 (s, 3H), 2.06 (s, 3H), 2.19 (s, 3H), 3.14 (q, J=7.6, 1H), 3.51 (d, J=10.0, 1H), 3.93 (d, J=10.0, 1H), 7.06-7.18 (m, 3H), 7.78 (s, 1H), 8.36 (s, 2H), 10.06 (s, 1H). LC-MS: $R_t$ (retention time)=2.84 min, MS: (ES) m/z 473 (M+H$^+$).

The second-eluting isomer, (3S*,4R*), was obtained in 31% yield (174 mg) as a white solid after subsequent recrystallization from hot ethyl acetate (5 mL). $^1$H NMR (400 MHz, DMSO-d$_6$) δ ☐ 1.19 (d, J=7.4, 3H), 1.69 (s, 3H), 2.12 (s, 3H), 2.19 (s, 3H), 2.61 (q, J=7.4, 1H), 3.28 (d, J=10.4, 1H), 4.20 (d,

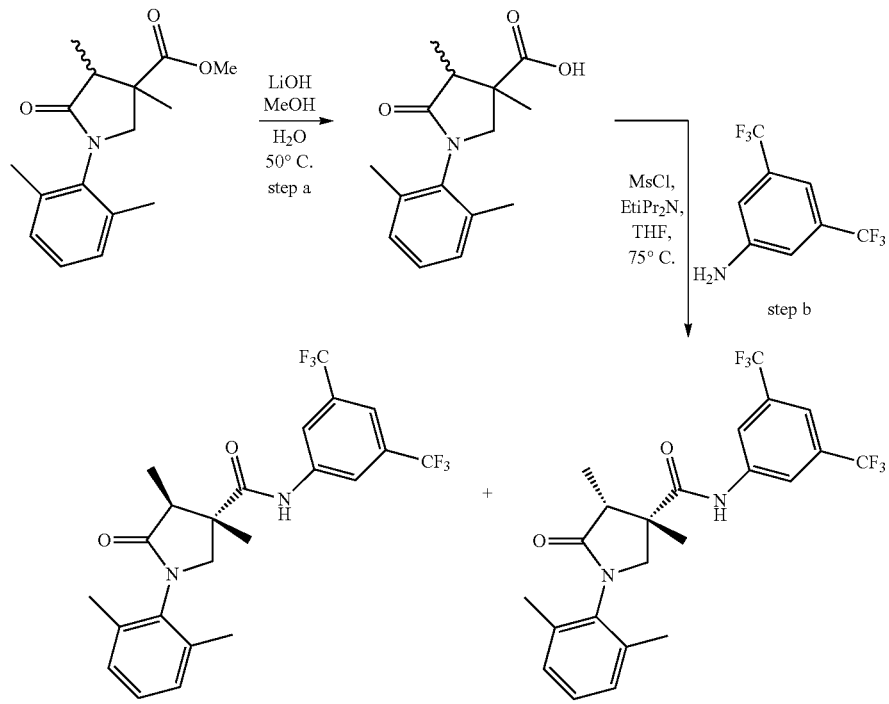

J=10.4, 1H), 7.06-7.18 (m, 3H), 7.79 (s, 1H), 8.36 (s, 2H), 10.15 (s, 1H). LC-MS: $R_t$ (retention time)=2.89 min, MS: (ES) m/z 473 (M+H$^+$).

Example 9

Synthesis of (±)-1-(2,6-dimethylphenyl)-3-hydroxymethyl-5-oxo-pyrrolidine-3-carboxylic acid [3,5-bis(trifluoromethyl)phenyl]amide

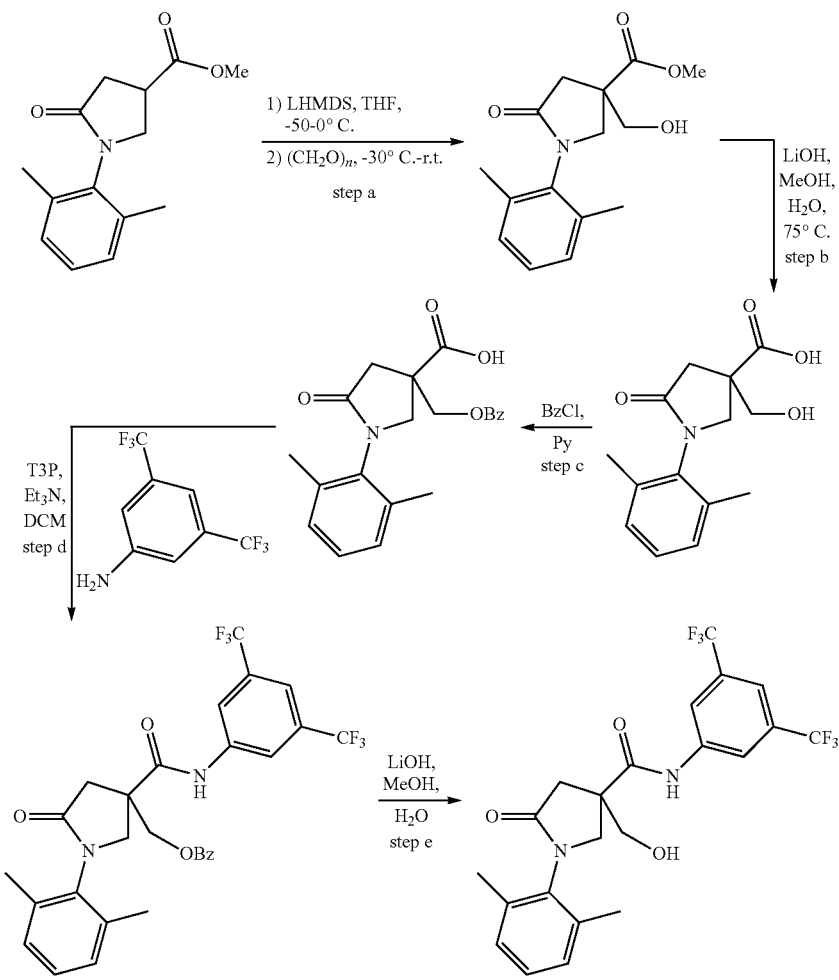

a) LHMDS (1.0 M in THF, 2.4 mL, 2.4 mmol) was added to the solution of 1-(2,6-dimethylphenyl)-5-oxo-pyrrolidine-3-carboxylic acid methyl ester (prepared in example 1 step b, 432 mg, 1.75 mmol) in THF (1 mL) in a reaction flask cooled to −50° C. under nitrogen atmosphere. The reaction mixture was allowed to warm up to 0° C., and then cooled back to −30° C., whereupon solid paraformaldehyde (263 mg, 8.75 mmol) was added. The reaction mixture was allowed to warm up to room temperature and was kept stirring for 1 h. 5 mL of half-saturated aqueous ammonium chloride solution was added, followed by 10 mL of CH$_2$Cl$_2$. The organic layer was concentrated in vacuo on silica gel and purified by flash chromatography (SiO$_2$, 40-100% EtOAc/hexanes) to give 136 mg of the desired compound (28% yield). LC-MS $R_t$ (retention time): 0.81 min, MS: (ES) m/z 278 (M+H$^+$).

b) Lithium hydroxide (71 mg, 2.94 mmol) was added to a solution of the ester from step a (136 mg, 0.49 mmol) in methanol (1 mL) and water (1 ml) at room temperature. The mixture was heated in a sealed vial to 75° C. for 1 h, at which time the reaction was completed. To the resulting solution 2.7 mL of 1 M aqueous hydrochloric acid was added and the solvent was removed in vacuo. LC-MS: $R_t$ (retention time): 0.39 min, MS: (ES) m/z 264 (M+H$^+$).

c) The dry residue from step b was dissolved/suspended in pyridine (2 mL). Benzoyl chloride (300 μL, 2.58 mmol) was added in three portions over 45 minutes. The solvent was removed in vacuo and the residue taken up in diethyl ether (10 mL) and water (10 mL). The mixture was acidified to pH=4 with 1 N aqueous hydrochloric acid. The organic layer solvent was removed in vacuo. LC-MS: $R_t$ (retention time): 2.07 min, MS: (ES) m/z 368 (M+H$^+$).

d) 3,5-Bis(trifluoromethyl)aniline (600 mg, 2.62 mmol) was added to a suspension of the benzoate prepared above and triethylamine (1.6 mL, 11.5 mmol) in CH$_2$Cl$_2$ (2 mL). T3P (50% solution, 2.3 mL, 3.87 mmol) was then added and the solution was allowed to stir at room temperature for 4 h. The solution was concentrated in vacuo on silica gel and purified by flash chromatography (SiO$_2$, 20-80% EtOAc/hexanes) to give 19 mg of the desired compound as an off-white solid. LC-MS: $R_t$ (retention time): 3.03 min, MS: (ES) m/z 579 (M+H$^+$).

e) Lithium hydroxide (2.5 mg, 0.104 mmol) was added to a solution of the benzoate from step d (10 mg, 0.017 mmol) in methanol (0.2 mL) and water (0.2 ml) at room temperature. The mixture was aged at room temperature for 2 h, at which time the reaction was completed. To the resulting solution 0.11 mL of 1 M aqueous hydrochloric acid was added and the solvent was removed in vacuo. The residue was purified by flash chromatography (SiO$_2$, 30-100% EtOAc/hexanes) to give 4 mg of the desired compound as an off-white solid. $^1$H NMR (400 MHz, DMSO-d$_6$) δ ☐ 2.07 (s, 3H), 2.16 (s, 3H), 2.61 (d, J=16.8, 1H), 3.02 (d, J=16.8, 1H), 3.58 (d, J=10.2, 1H), 3.86 (d, J=5.2, 2H), 3.98 (d, J=10.2, 1H), 5.54 (t, J=5.2, 1H), 7.05-7.18 (m, 3H), 7.78 (s, 1H), 8.36 (s, 2H), 10.17 (s, 1H). LC-MS: R$_t$ (retention time): 2.57 min, MS: (ES) m/z 475 (M+H$^+$).

LC-MS method: Agilent Zorbax SB-C18, 2.1×50 mm, 5μ, 35° C., 1 mL/min flow rate, a 2.5 min gradient of 20% to 100% B with a 1.0 min wash at 100% B; A=0.1% formic acid/5% acetonitrile/94.9 water, B=0.1% formic acid/5% water/94.9 acetonitrile Example 10

Synthesis of 3,4-dimethyl-5-oxo-1-o-tolyl-pyrrolidine-3-carboxylic acid (3,5-bis-trifluoromethyl-phenyl)amide solid was collected by filtration and rinsed with hexanes to give the desired acid in 55% yield (10.7 g). LC-MS R$_t$ (retention time): 0.41 min, MS: (ES) m/z 220.2 (M+H$^+$).

b) TMSCHN$_2$ (2.0 M in Et$_2$O, 7 mL, 14 mmol) was added to a solution of acid from step a (0.75 g, 3.4 mmol) in MeOH (17 mL) at 0° C. The reaction was stirred at room temperature for 15 min and quenched with acetic acid (~0.5 mL). The solution was concentrated under reduced pressure. The residue was purification by flash chromatography (SiO$_2$, 0-40% hexanes/EtOAc) to give the desired product in 99% yield (0.79 g). LC-MS R$_t$ (retention time): 0.99 min, MS: (ES) m/z 234.1 (M+H$^+$).

c) Lithium bis(trimethylsily)amide (1.0 M in THF, 5.1 mL, 5.1 mmol) was added to a solution of ester from step b (0.79 g, 3.4 mmol) in THF (36 mL) in a reaction flask at −50° C. and stirred for 5 min. The reaction was warmed to 0° C., and followed by the addition of MeI (2.5 g, 18 mmol). The reaction was then stirred at room temperature for 2 h. The reaction was then quenched with saturated NH$_4$Cl. The layers were separated and the aqueous layer was extracted with EtOAc (3×). The combined organic layers were dried (MgSO$_4$) and concentrated under reduced pressure. The residue was purified by flash chromatography (SiO$_2$, 0-50% hexanes/EtOAc) to give the desired compound 29% yield (0.27 g). LC-MS R$_t$ (retention time): 2.25 min, MS: (ES) m/z 262.3 (M+H$^+$).

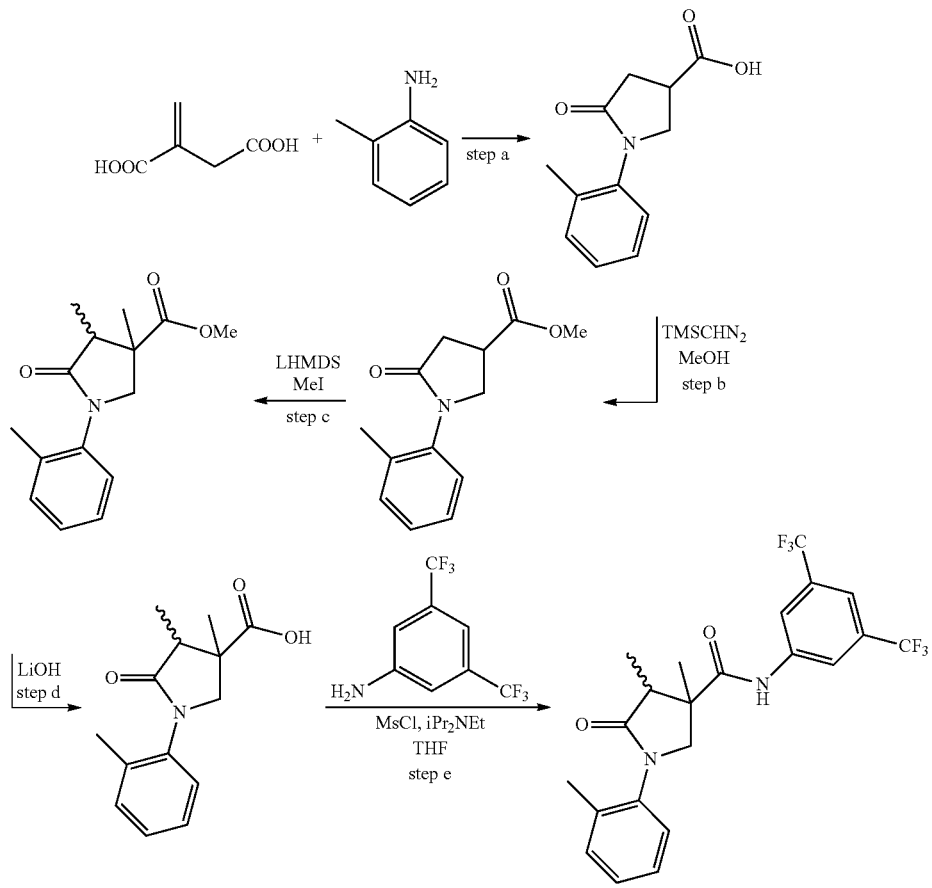

a) Itaconic acid (12.1 g, 93 mmol) was added to a solution of 2-methylaniline (10 g, 93 mmol) and the reaction was heated at 140° C. for 1 h. The solution was then cooled to 65° C. and EtOAc (100 mL) was added to produce a solid. The d) Lithium hydroxide (1.0 M in H$_2$O, 10 mL, 10 mmol) was added to a solution of the ester from step c (0.27 g, 1.03 mmol) in MeOH (5 ml). The resulting solution was heated at 75° C. for 18 h. The solution was concentrated under reduced pressure to give 1/4 of the original volume and 6 M aqueous HCl (~1 mL) was added dropwise to adjust the pH to about 4. The aqueous layer was then extracted with EtOAc (3×). The combined organic layers were dried (MgSO$_4$) and concentrated under reduced pressure to give the crude product (0.075 g, 28%). LC-MS: R$_t$ (retention time): 1.02 min and 1.15 min (two diastereomers), MS: (ES) m/z 248.2 (M+H$^+$).

e) Methanesulfonic acid (0.04 g, 0.43 mmol) and iPr$_2$NEt (0.11 mL, 0.63 mmol) were added to a solution of the acid from step d (0.075 g, 0.29 mmol) in THF (2.9 ml) at room temperature. The resulting mixture was stirred at room temperature for 5 min, followed by addition of 3,5-bis(trifluoromethyl)aniline (0.066 g, 0.29 mmol). The reaction was heated at 75° C. until the reaction was completed (4 h). The mixture was concentrated under reduced pressure. Purification by flash chromatography (SiO$_2$, 0-75% hexanes/EtOAc) to give the desired product as a 2:1 mixture of diastereomers in 23% yield (0.031 g). $^1$H NMR (400 MHz, DMSO-d$_6$): δ 10.11 (s, 0.7H), 10.09 (s, 0.3H), 8.36 (s, 2H), 7.79 (s, 1H), 7.26-7.21 (m, 4H), 4.28 (d, J=10.0 Hz, 0.3H), 4.13 (d, J=10.0 Hz, 0.7H), 3.54 (d, J=9.6 Hz, 0.7H), 3.38 (d, J=10.4 Hz, 0.3H), 3.14 (q, J=7.2 Hz, 0.7H), 2.62 (q, J=7.2 Hz, 0.3H), 2.17 (s, 1H), 2.15 (s, 2H), 1.63 (s, 1H), 1.45 (s, 2H), 1.16 (d, J=7.2 Hz, 1H), 1.15 (d, J=7.2 Hz, 2H). LC-MS: R$_t$ (retention time): 2.28 min, MS: (ES) m/z 459.4 (M+H$^+$).

Example 11

Synthesis of 1-(2,6-dimethylphenyl)-3-methoxymethyl-5-oxo-pyrrolidine-3-carboxylic acid (3,5-bis-trifluoromethylphenyl)amide a) Lithium bis(trimethylsily)amide (1.0 M in THF, 1.9 mL, 1.9 mmol) was added to a solution of 1-(2,6-dimethylphenyl)-5-oxo-pyrrolidine-3-carboxylic acid methyl ester (0.4 g, 1.6 mmol) in THF (16 mL) in a reaction flask at −50° C. and stirred 5 min. The reaction was then warmed to 0° C., followed by addition of MOMBr (0.29 g, 4.0 mmol). The reaction was stirred at room temperature for 2 h and quenched with saturated NH$_4$Cl. The layers were separated and the aqueous layer was extracted with EtOAc (3×). The combined organic layers were dried (MgSO$_4$) and concentrated under reduced pressure. The residue was purified by flash chromatography (SiO$_2$, 0-60% hexanes/EtOAc) to give the desired compound in 43% yield (0.2 g). LC-MS: R$_t$ (retention time): 1.83 min, MS: (ES) m/z 292.3 (M+H$^+$).

b) Lithium hydroxide (1.0 M in H$_2$O, 6.8 mL, 6.8 mmol) was added to a solution of the ester from step a (0.2 g, 0.68 mmol) in MeOH (3 ml). The resulting solution was heated at 75° C. for 2 h. The solution was concentrated under reduced pressure to give 1/4 of the original volume and 6 M aqueous HCl (~0.5 mL) was added drop wise to adjust the pH to about 4. The aqueous layer was extracted with EtOAc (3×). The combined organic layers were dried (MgSO$_4$) and concentrated under reduced pressure to give the crude product (0.18 g, 96%). LC-MS: R$_t$ (retention time): 1.11, MS: (ES) m/z 278.3 (M+H$^+$).

c) Methanesulfonic acid (0.038 g, 0.32 mmol) and iPr$_2$NEt (0.1 mL, 0.59 mmol) were added to a solution of the acid from step b (0.075 g, 0.27 mmol) in THF (2.7 ml) at room temperature. The resulting mixture was stirred at room temperature for 5 min, followed by the addition of 3,5-bis(trifluoromethyl)aniline (0.06 g, 0.27 mmol). The reaction was heated at 75° C. until the reaction was completed (3 h). The mixture

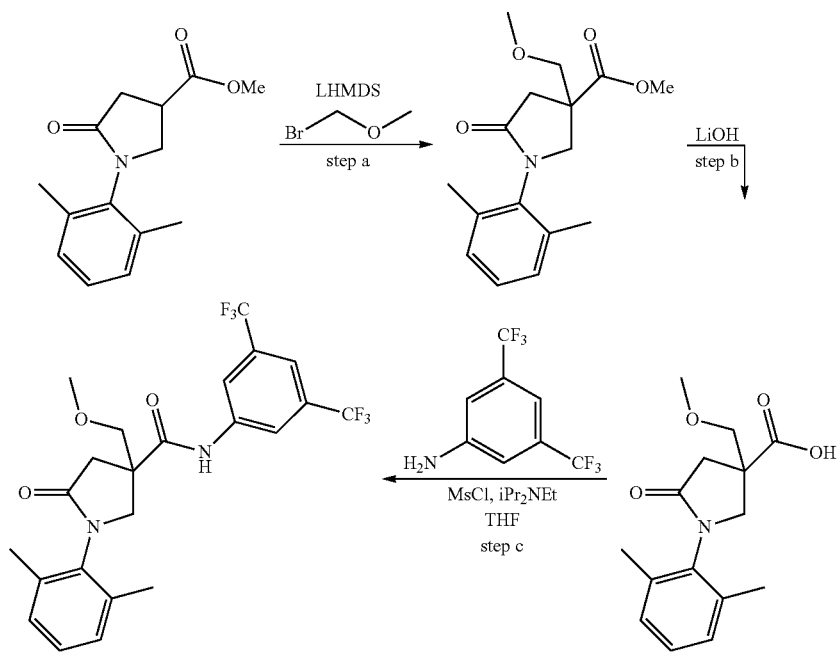

was concentrated under reduced pressure. Purification by flash chromatography (SiO$_2$, 0-75% hexanes/EtOAc) gave the desired product in 22% yield (0.035 g). $^1$H NMR (400 MHz, DMSO-d$_6$): δ 11.25 (s, 1H), 8.36 (s, 2H), 7.79 (s, 1H), 7.14-7.09 (m, 3H), 4.01 (d, J=10.0 Hz, 1H), 3.82 (s, 2H), 3.60 (d, J=10.4, 1H), 3.32 (s, 3H), 3.08 (d, J=17.2 Hz, 1H), 2.63 (d, J=16.8 Hz, 1H), 2.17 (s, 3H), 2.06 (s, 3H). LC-MS: R$_t$ (retention time): 2.34 min, MS: (ES) m/z 489.4 (M+H$^+$).

Example 12

Synthesis of 1-(2,6-dimethylphenyl)-3-isobutyl-5-oxo-pyrrolidine-3-carboxylic acid (3,5-bis-trifluoromethylphenyl)amide

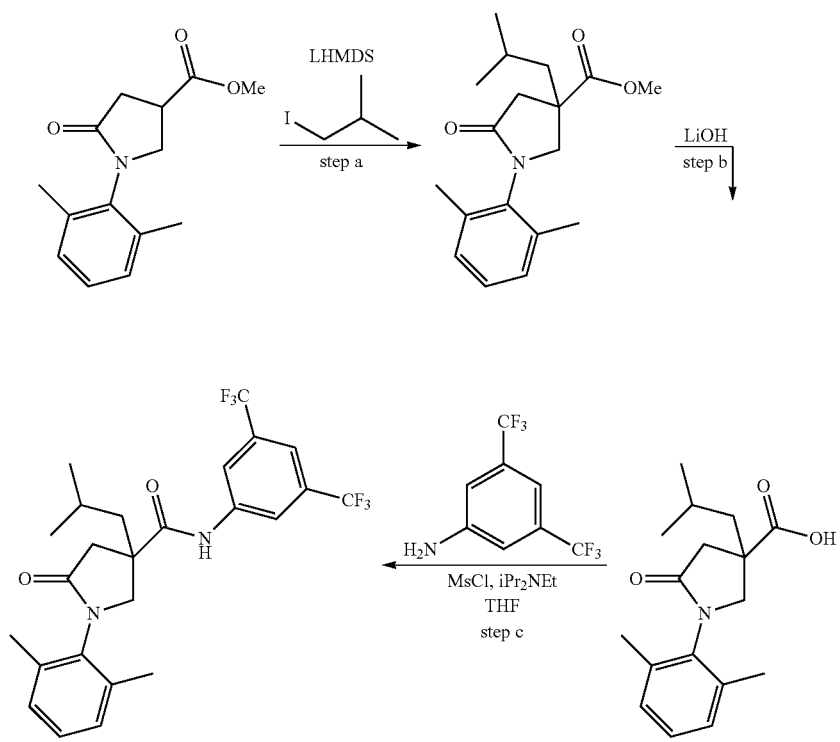

a) Lithium bis(trimethylsily)amide (1.0 M in THF, 1.9 mL, 1.9 mmol) was added to a solution of 1-(2,6-dimethylphenyl)-5-oxo-pyrrolidine-3-carboxylic acid methyl ester (0.4 g, 1.6 mmol) in THF (16 mL) in a reaction flask at −50° C. and stirred for 5 min. The reaction was then warmed to 0° C., followed by the addition of 1-iodo-2-methylpropane (0.73 g, 4.0 mmol). The reaction was warmed to room temperature and stirred for 1 h. The reaction was quenched saturated NH$_4$Cl. The layers were separated and the aqueous layer was extracted with EtOAc (3×). The combined organic layers were dried (MgSO$_4$) and concentrated under reduced pressure. The residue was purified by flash chromatography (SiO$_2$, 0-70% hexanes/EtOAc) to give the desired compound in 43% yield (0.18 g). LC-MS: R$_t$ (retention time): 2.56 min, MS: (ES) m/z 304.4 (M+H$^+$).

b) Lithium hydroxide (1.0 M in H$_2$O, 10 mL, 10 mmol) was added to a solution of the ester from step a (0.18 g, 0.59 mmol) in MeOH (5 ml). The resulting solution was heated at 75° C. for 2 h. The solution was concentrated under reduced pressure to give 1/4 of the original volume and 6 M aqueous HCl (~0.5 mL) was added dropwise to adjust the pH to about 4. The aqueous layer was extracted with EtOAc (3×). The combined organic layers were dried (MgSO$_4$) and concentrated under reduced pressure to give the crude product (0.13 g, 83%). LC-MS: R$_t$ (retention time): 2.00 min, MS: (ES) m/z 290.3 (M+H$^+$).

c) Methanesulfonic acid (0.065 g, 0.56 mmol) and iPr$_2$NEt (0.16 mL, 0.96 mmol) were added to a solution of the acid from step b (0.13 g, 0.47 mmol) in THF (4.7 ml) at room temperature. The resulting mixture was stirred at room temperature for 5 min, followed by the addition of 3,5-bis(trifluoromethyl)aniline (0.06 g, 0.27 mmol). The reaction was heated at 75° C. until the reaction was completed (3 h). The mixture was concentrated under reduced pressure. Purification by flash chromatography (SiO$_2$, 0-75% hexanes/EtOAc) gave the desired product in 22% yield (0.051 g). $^1$H NMR (400 MHz, DMSO-d$_6$): δ 10.38 (s, 1H), 8.34 (s, 2H), 7.79 (s, 1H), 7.12-7.05 (m, 3H), 3.99 (d, J=10.4 Hz, 1H), 3.61 (d, J=10.4, 1H), 3.13 (d, J=16.4 Hz, 1H), 2.60 (d, J=16.8 Hz, 1H), 2.15 (s, 3H), 2.05 (dd, J=6.0, 5.8 Hz, 1H), 1.97 (s, 3H), 1.96 (dd, J=6.0, 5.8 Hz, 1H), 1.23 (p, J=6.5 Hz, 1H), 0.87 (d, J=6.4 Hz, 3H), 0.85 (d, J=7.2 Hz, 3H). LC-MS: R$_t$ (retention time): 3.09 min, MS: (ES) m/z 501.5 (M+H$^+$).

Example 13

Synthesis of 3-(3,6-dihydro-2H-pyran-4-yl)-1-(2,6-dimethylphenyl)-5-oxo-pyrrolidine-3-carboxylic acid (3,5-bis-trifluoromethylphenyl)amide

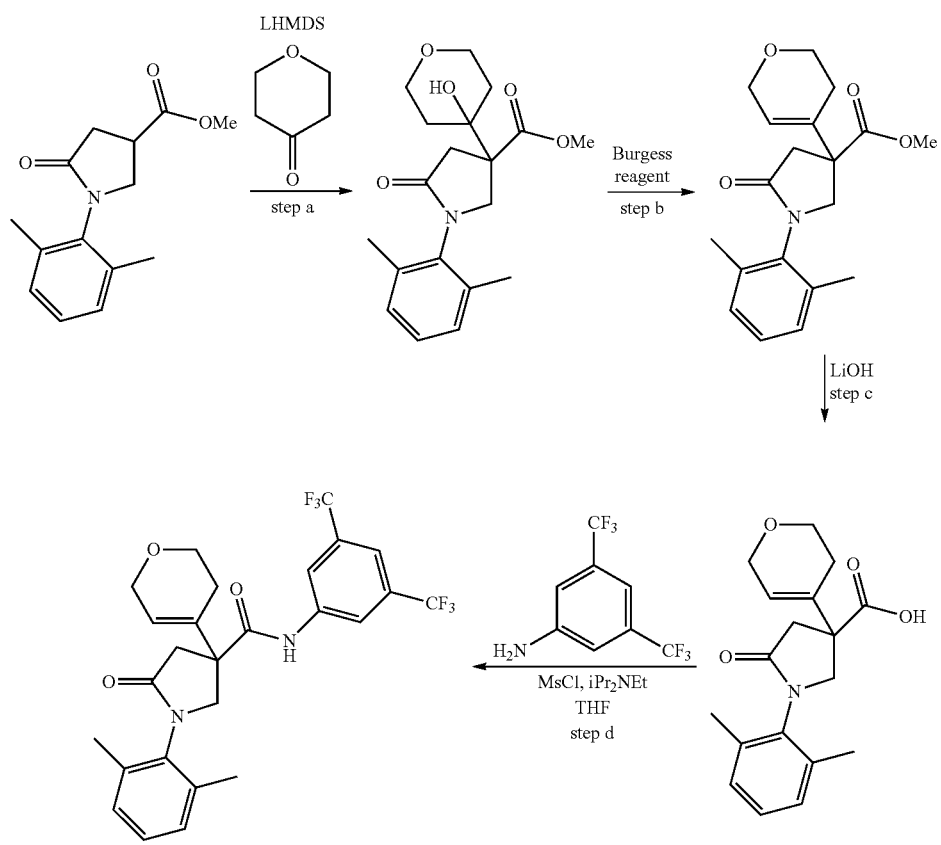

a) Lithium bis(trimethylsilyl)amide (1.0 M in THF, 1.9 mL, 1.9 mmol) was added to a solution of 1-(2,6-dimethylphenyl)-5-oxo-pyrrolidine-3-carboxylic acid methyl ester (0.4 g, 1.6 mmol) in THF (16 mL) in a reaction flask at −78° C. The reaction was stirred at −78° C. for 5 min, followed by addition of tetrahydro-4H-pyran-4-one (0.4 g, 4.0 mmol). The reaction was slowly warmed to room temperature over 1 h. The reaction was quenched with acetic acid (1 mL). The mixture was concentrated under reduced pressure. The residue was purified by flash chromatography (SiO$_2$, 0-100% hexanes/EtOAc) to give the desired compound in 32% yield (0.18 g). LC-MS: R$_t$ (retention time): 1.32 min, MS: (ES) m/z 348.4 (M+H$^+$).

b) Burgess reagent (0.12 g, 0.2 mmol) was added to a solution of the ester from step a (0.15 g, 0.43 mmol) in THF (4 ml). The resulting solution was heated at 75° C. for 1 h. The mixture was concentrated under reduced pressure. The residue was purified by flash chromatography (SiO$_2$, 0-100% hexanes/EtOAc) to give the desired compound in 76% yield (0.05 g). LC-MS: R$_t$ (retention time): 1.86 min, MS: (ES) m/z 330.3 (M+H$^+$).

c) Lithium hydroxide (1.0 M in H$_2$O, 1.5 mL, 1.5 mmol) was added to a solution of the ester from step b (0.05 g, 1.5 mmol) in MeOH (0.8 ml). The resulting solution was heated at 75° C. for 1 h. The solution was concentrated under reduced pressure to give 1/4 of the original volume and 6 M aqueous HCl (~0.5 mL) was added drop wise to adjust the pH to about 4. The aqueous layer was extracted with EtOAc (3×). The combined organic layers were dried (MgSO$_4$) and concentrated under reduced pressure to give the crude product (0.041 g, 87%). LC-MS: R$_t$ (retention time): 1.15 min, MS: (ES) m/z 316.3 (M+H$^+$).

d) Methanesulfonic acid (0.018 g, 0.15 mmol) and iPr$_2$NEt (0.042 mL, 0.28 mmol) were added to a solution of the acid from step c (0.041 g, 0.13 mmol) in THF (1.3 ml) at room temperature. The resulting mixture was stirred at room temperature for 5 min, followed by addition of 3,5-bis(trifluoromethyl)aniline (0.029, 0.13 mmol). The reaction was heated at 75° C. until the reaction was completed (18 h). The mixture was concentrated under reduced pressure. Purification by flash chromatography (SiO$_2$, 0-75% hexanes/EtOAc) gave the desired product 39% yield (0.027). $^1$H NMR (400 MHz, DMSO-d$_6$): δ 10.17 (s, 1H), 8.36 (s, 2H), 7.80 (s, 1H), 7.14-7.07 (m, 3H), 5.92 (s, 1H) 4.17-4.12 (m, 3H), 3.74-3.71 (m, 2H), 3.64-3.63 (m, 1H), 3.16 (d, J=16.4 Hz, 1H), 2.93 (d, J=16.4, 1H), 2.12-2.01 (m. 2H), 2.10 (s, 3H), 2.03 (s, 3H). LC-MS: R$_t$ (retention time): 2.77 min, MS: (ES) m/z 527.5 (M+H$^+$).

Example 14

Synthesis of 1-(2,6-dimethylphenyl)-5-oxo-3-(tetrahydro-pyran-4-yl)-pyrrolidine-3-carboxylic acid (3,5-bis-trifluoromethylphenyl)amide

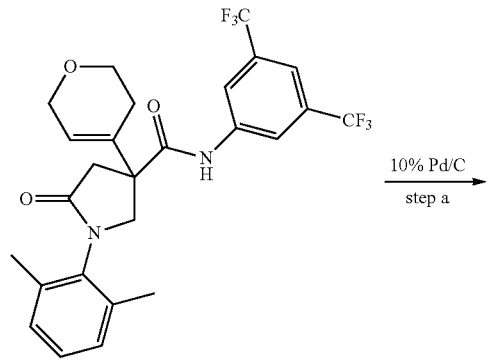

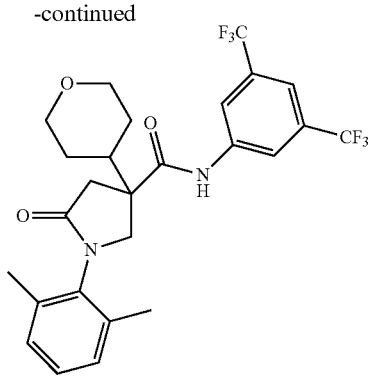

a) 10% Pd/C (0.002 g) was added to a solution of amide (0.01 g, 0.019 mmol) in MeOH (1.9 mL) in a reaction flask and stirred under H$_2$ at room temperature for 5 h. The reaction mixture was then filtered through Celite, washed with MeOH, and the filtrate was concentrated under reduced pressure. Purification by flash chromatography (SiO$_2$, 0-75% hexanes/EtOAc) gave the desired product in 100% yield (0.01 g). $^1$H NMR (400 MHz, DMSO-d$_6$): δ 10.38 (s, 1H), 8.36 (s, 2H), 7.79 (s, 1H), 7.12-7.06 (m, 3H), 4.04 (d, J=10.4 Hz, 1H), 3.92-3.88 (m, 2H), 3.75 (d, J=10.8, 1H), 3.28-3.23 (m, 2H), 3.09 (d, J=16.8 Hz, 1H), 2.72 (d, J=17.6 Hz, 1H), 2.39 (bs, 1H), 2.14 (s, 3H), 1.95 (s, 3H), 1.62-1.51 (m, 2H), 1.39-1.33 (m, 2H). LC-MS: R$_t$ (retention time): 2.72 min, MS: (ES) m/z 529.5 (M+H$^+$).

Example 15

Synthesis of 2-(2,6-dimethylphenyl)-1-oxo-hexahydro-pyrano[3,4-c]pyrrole-3a-carboxylic acid (3,5-bis-trifluoromethylphenyl)amide

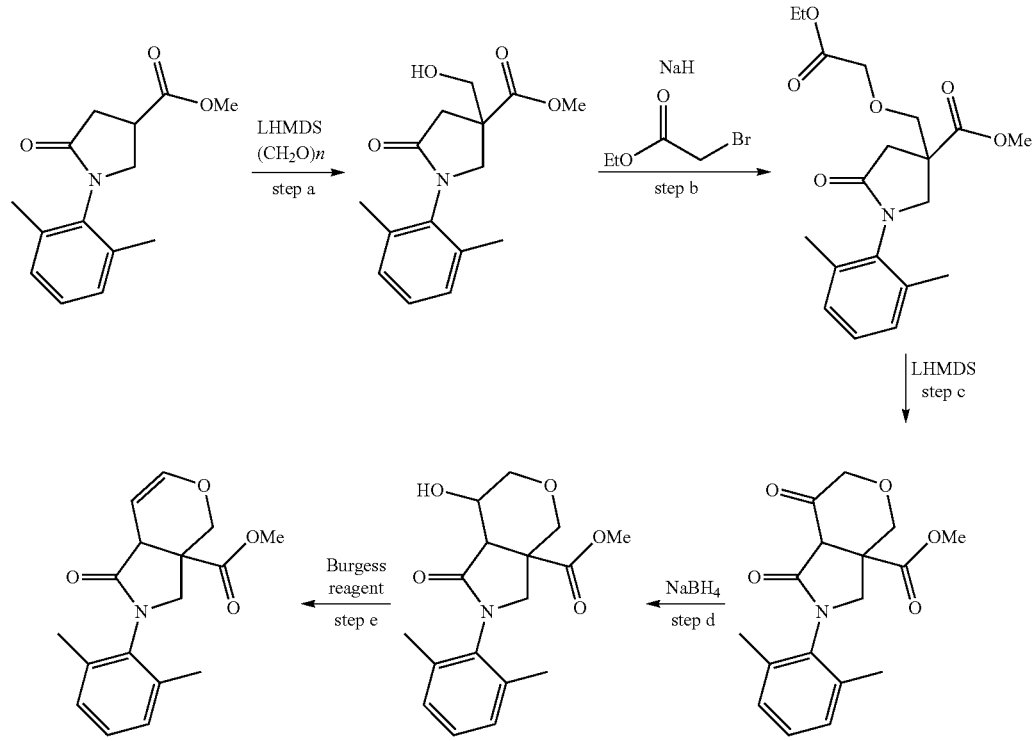

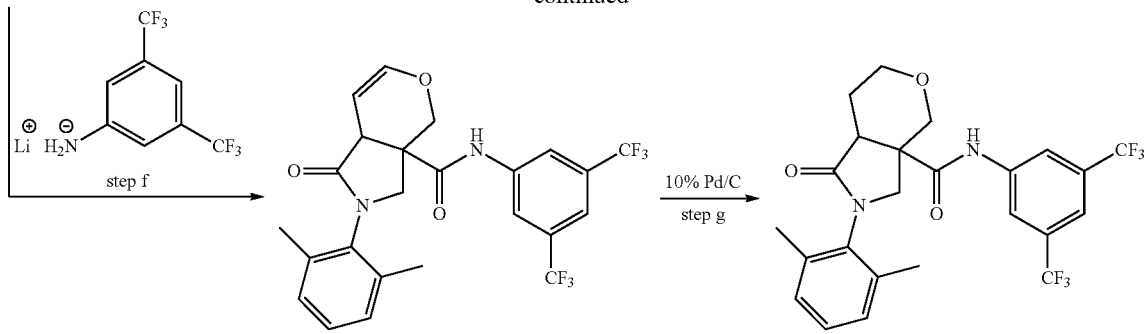

-continued a) Lithium bis(trimethylsily)amide (1.0 M in THF, 24 mL, 24 mmol) was added to a solution of 1-(2,6-dimethylphenyl)-5-oxo-pyrrolidine-3-carboxylic acid methyl ester (5 g, 20.2 mmol) in THF (40 mL) in a reaction flask at −50° C. The reaction was stirred at −50° C. for 10 min, followed by addition of paraformaldehyde (6 g, 200 mmol) in THF (10 mL). The reaction was then warmed to room temperature stirred for 1 h. The reaction was quenched with saturated $NH_4Cl$. The layers were separated and the aqueous layer was extracted with EtOAc (3×). The combined organic layers were dried ($MgSO_4$) and concentrated under reduced pressure. The residue was purified by flash chromatography ($SiO_2$, 0-60% hexanes/EtOAc) to give the desired compound in 47% yield (2.6 g). LC-MS: $R_t$ (retention time): 0.81 min, MS: (ES) m/z 278.0 (M+H$^+$).

b) NaH (60% dispersion in mineral oil, 0.7 g, 17.3 mmol) was added slowly to the solution of alcohol from step a (4.0 g, 14.4 mmol) and bromo ethyl acetate (4.8 g, 29 mmol) in THF (72 mL) in a reaction flask at 0° C. The reaction was stirred at room temperature for 18 h and quenched with saturated $NH_4Cl$. The layers were separated and the aqueous layer was extracted with EtOAc (3×). The combined organic layers were dried ($MgSO_4$) and concentrated under reduced pressure. The residue was purified by flash chromatography ($SiO_2$, 0-45% hexanes/EtOAc) to give the desired compound in 56% yield (2.9 g). LC-MS: $R_t$ (retention time): 2.05 min, MS: (ES) m/z 364.4 (M+H$^+$).

c) Lithium bis(trimethylsily)amide (1.0 M in THF, 20 mL, 20 mmol) was added to the solution of the ester from step b (2.9 g, 8.1 mmol) in THF (80 mL) in a reaction flask at −78° C. The reaction was stirred for 1 h at −78° C. min and quenched with saturated $NH_4Cl$. The layers were separated and the aqueous layer was extracted with EtOAc (3×). The combined organic layers were dried ($MgSO_4$) and concentrated under reduced pressure. The residue was purified by flash chromatography ($SiO_2$, 0-60% hexanes/EtOAc) to give the desired compound in 50% yield (1.3 g). LC-MS: $R_t$ (retention time): 1.74 min, MS: (ES) m/z 318.3 (M+H$^+$).

d) Sodium borohydride (0.053 g, 1.43 mmol) was added slowly to the solution of ketone from step c (0.35 g, 1.1 mmol) in THF (11 mL) in a reaction flask at 0° C. The reaction was stirred at room temperature for 1 h and quenched with $H_2O$ (5 mL). The layers were separated and the aqueous layer was extracted with EtOAc (3×). The combined organic layers were dried ($MgSO_4$) and concentrated under reduced pressure. The residue was purified by flash chromatography ($SiO_2$, 0-70% hexanes/EtOAc) to give the desired compound in 83% yield (0.29 g). LC-MS: $R_t$ (retention time): 1.27 min, MS: (ES) m/z 320.3 (M+H$^+$).

e) Burgess reagent (0.73 g, 2.6 mmol) was added to a solution of the alcohol from step d (0.55 g, 1.7 mmol) in THF (17 ml). The resulting solution was heated at 75° C. for 2 h. The mixture was concentrated under reduced pressure. The residue was purified by flash chromatography ($SiO_2$, 0-100% hexanes/EtOAc) to give the desired compound in 46% yield (0.25 g). LC-MS: $R_t$ (retention time): 1.54 min, MS: (ES) m/z 302.3 (M+H$^+$).

f) n-BuLi (2.5 M in hexanes, 0.91 mL, 2.3 mmol) was added to a solution of 3,5-bis(trifluoromethyl)aniline (0.56 g, 2.5 mmol) in THF (4 mL) at −78° C. The reaction was stirred at −78° C. for 30 min and was then warmed to room temperature. Addition of the ester from step e (0.25 g, 0.82 mmol) was followed and the resulting mixture heated at 75° C. for 2 h. The mixture was concentrated under reduced pressure. Purification by flash chromatography ($SiO_2$, 0-75% hexanes/EtOAc) gave the desired product in 7% yield (0.027 g). LC-MS: $R_t$ (retention time): 2.78 min, MS: (ES) m/z 499.4 (M+H$^+$).

g) 10% Pd/C (0.003 g) was added to the solution of amide (0.006 g, 0.012 mmol) in MeOH (1.2 mL) and EtOAc (1.2 mL) in a reaction flask and stirred under $H_2$ at room temperature for 24 h. The reaction mixture was then filtered through Celite, washed with MeOH, and the filtrate was concentrated under reduced pressure. Purification by flash chromatography ($SiO_2$, 0-100% hexanes/EtOAc) gave the desired product in 83% yield (0.005 g). $^1$H NMR (400 MHz, DMSO-d$_6$): δ 10.21 (s, 1H), 8.33 (s, 2H), 7.79 (s, 1H), 7.16-7.08 (m, 3H), 4.42 (d, J=12.4 Hz, 1H), 3.80 (d, J=9.2, 2H), 3.73 (d, J=12.4, 1H), 3.46 (d, J=10.4, 1H), 3.38-3.3 (m, 4H), 2.24 (s, 3H), 2.06 (s, 3H). LC-MS: $R_t$ (retention time): 2.79 min, MS: (ES) m/z 501.4 (M+H$^+$).

Example 16

Synthesis of 3-((1H-imidazol-2-yl)methyl)-N-(3,5-bis(trifluoromethyl)phenyl)-1-(2,6-dimethylphenyl)-5-oxopyrrolidine-3-carboxamide

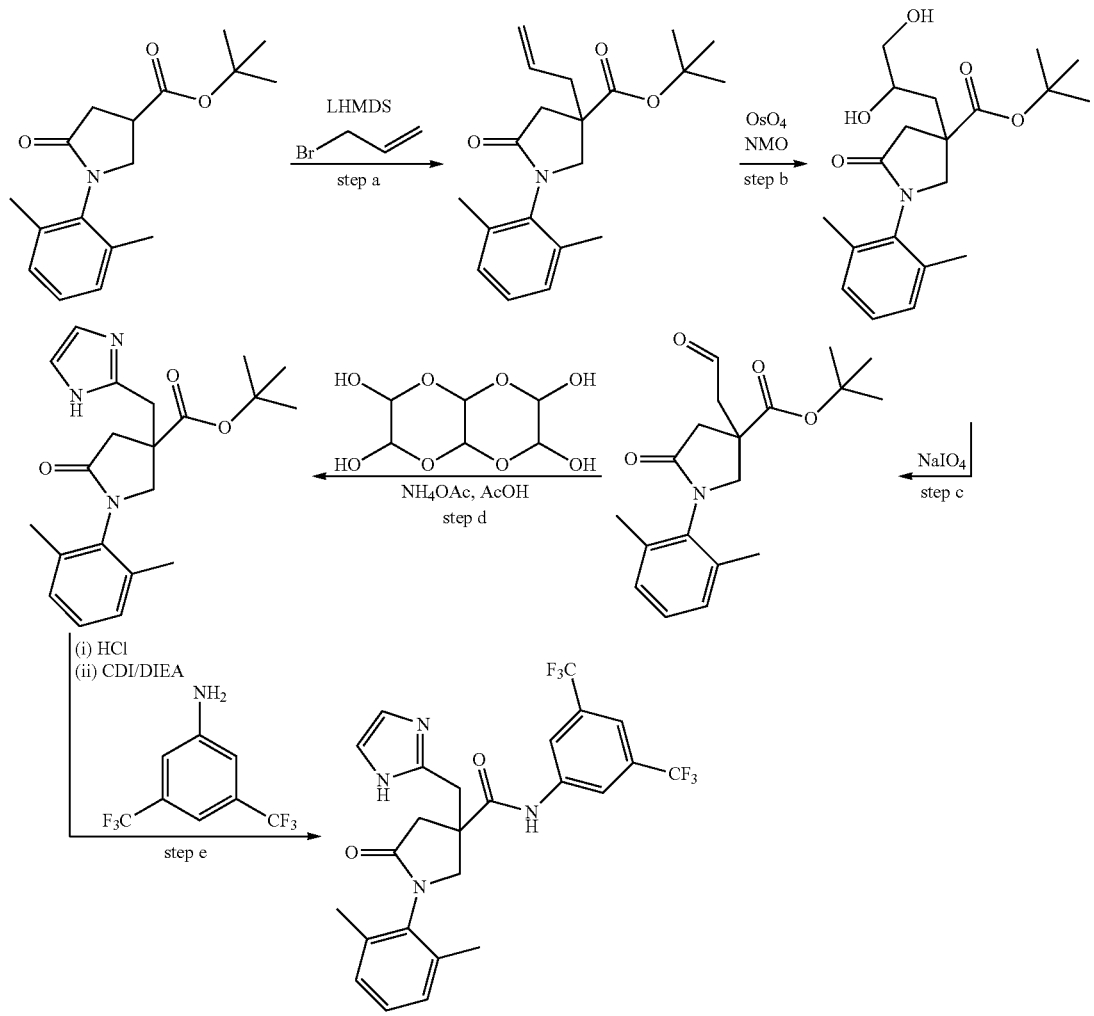

a) Lithium bis(trimethylsily)amide (1.0 M in THF, 27 mL, 27 mmol) was added to a solution of 1-(2,6-dimethylphenyl)-5-oxo-pyrrolidine-3-carboxylic acid tert-butyl ester (7 g, 24.2 mmol) in THF (48 mL) in a reaction flask at −50° C. and stirred for 5 min. The reaction was raised to 0° C., and allyl bromide (5.8 g, 48.4 mmol) was added. The reaction was then warmed to room temperature, stirred for 2 h, and quenched with saturated NH₄Cl. The layers were separated and the aqueous layer was extracted with EtOAc (3×). The combined organic layers were dried (MgSO₄) and concentrated under reduced pressure. The residue was purified by flash chromatography (SiO₂, 0-60% hexanes/EtOAc) to give the desired compound in 62% yield (5.0 g). LC-MS: $R_t$ (retention time): 2.68 min, MS: (ES) m/z 330.4 (M+H⁺).

b) OsO₄ (0.08 M in t-BuOH, 19 mL, 1.52 mmol) was added to a solution of the ester from step a (5.02 g, 15.2 mmol) and 4-methylmorpholine N-oxide (2.6 g, 23 mmol) in tBuOH (88 ml), THF (22 mL), and H₂O (11 mL). The resulting solution was stirred at room temperature for 18 h. The reaction was quenched with saturated Na₂S₂O₃ (40 mL). The layers were separated and the aqueous layer was extracted with EtOAc (3×). The combined organic layers were dried (MgSO₄) and concentrated under reduced pressure. The crude was used without further purifications (2.5 g, 45%). LC-MS: $R_t$ (retention time): 1.71, MS: (ES) m/z 364.4 (M+H⁺).

c) A solution of tert-butyl 3-(2,3-dihydroxypropyl)-1-(2,6-dimethylphenyl)-5-oxopyrrolidine-3-carboxylate (1.2 g, 3.3 mmol) dissolved in THF (8 mL) was treated with NaIO₄ (1.4 g, 6.6 mmol) and water (2 mL). After stirring overnight at room temperature, methanol (2 mL) was added and the mixture was diluted with ethyl acetate (15 mL) and washed with water. The aqueous phase was washed with ethyl acetate and the organic layers were combined, dried and the solvent evaporated. The residue was purified by flash chromatography (SiO₂, 10-100% EtOAc/hexanes) to yield tert-butyl 1-(2,6-dimethylphenyl)-5-oxo-3-(2-oxoethyl)pyrrolidine-3-carboxylate (980 mg, 88% yield). LC-MS $R_t$ (retention time): 2.28 min, MS: (ES) m/z 332 (M+H⁺).

d) A mixture of tert-butyl 1-(2,6-dimethylphenyl)-5-oxo-3-(2-oxoethyl)pyrrolidine-3-carboxylate (863 mg, 2.5 mmol), glyoxal trimer dihydrate (210 mg, 1.0 mmol), ammonium acetate (635 mg, 8 mmol), and acetic acid (180 mg, 3 mmol) in THF-MeOH mixture (1:1, 10 mL) was stirred at 40° C. overnight. After cooling to RT the reaction mixture was diluted with 25 mL ethyl acetate and washed with water (2×15 mL). The aqueous phase was back extracted with ethyl acetate (15 mL). The combined organic layer was dried and the solvent was evaporated. The residue was purified by flash chromatography (SiO$_2$, 10-100% EtOAc/hexanes) to yield 467 mg of tert-butyl 3-((1H-imidazol-2-yl)methyl)-1-(2,6-dimethylphenyl)-5-oxopyrrolidine-3-carboxylate (52% yield). LC-MS R$_t$ (retention time): 0.51 min MS: (ES) m/z 370 (M+H$^+$).

e) tert-Butyl 3-((1H-imidazol-2-yl)methyl)-1-(2,6-dimethylphenyl)-5-oxopyrrolidine-3-carboxylate prepared in Step b above (460 mg, 1.2 mmol) was dissolved in 4 mL of 4 M HCl in dioxane and heated at 60° C. for 2 h. The solvent was evaporated to dryness and the residue suspended in THF (5 mL) was treated with carbonyl diimidazole (201 mg, 1.2 mmol) and diisopropylethyl amine (626 µL, 3.6 mmol) and heated at 40° C. for 1 h. The warm reaction mixture was treated with 3,5-bis(trifluoromethyl)aniline (550 mg, 2.4 mmol) and heating was continued for another 2 h. After cooling to room temperature the reaction mixture was diluted with 25 mL ethyl acetate and washed with water. The organic phase was dried, solvent evaporated and the residue was purified by flash chromatography (SiO$_2$, 0-15% MeOH/DCM) to afford 260 mg of 3-((1H-imidazol-2-yl)methyl)-N-(3,5-bis(trifluoromethyl)phenyl)-1-(2,6-dimethylphenyl)-5-oxopyrrolidine-3-carboxamide (42% yield). $^1$H NMR (400 MHz, CDCl$_3$) δ 2.14 (s, 3H), 2.19 (s, 3H), 2.52 (d, 1H, J=17 Hz), 3.28 (d, 1H, J=17 Hz), 3.38-3.42 (m, 3H), 3.59 (d, 1H, J=10.6 Hz), 4.20 (d, 1H, J=10.6 Hz), 1.60 (bs, 2H), 7.00-7.20 (m, 3H), 7.57 (s, 1H), 8.18 (s, 2H). LC-MS: R$_t$ (retention time)=2.57 min, MS: (ES) m/z 525 (M+H$^+$).

Example 17

Synthesis of 3-benzyloxymethyl-1-(2,6-dimethylphenyl)-5-oxo-pyrrolidine-3-carboxylic acid (3,5-bis-trifluoromethylphenyl)amide

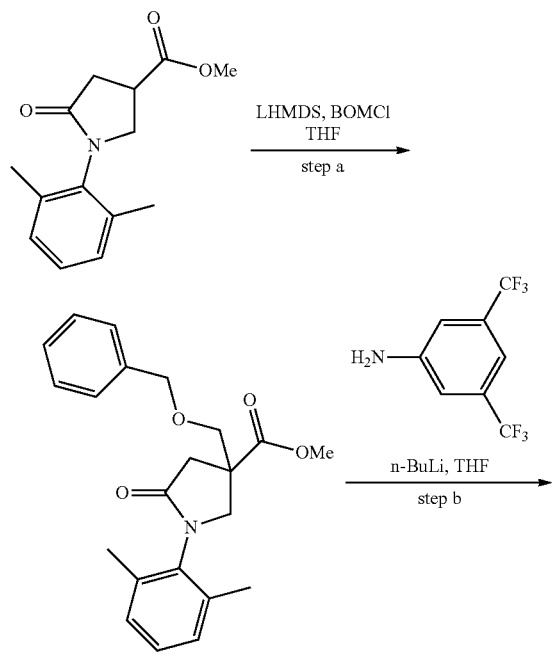

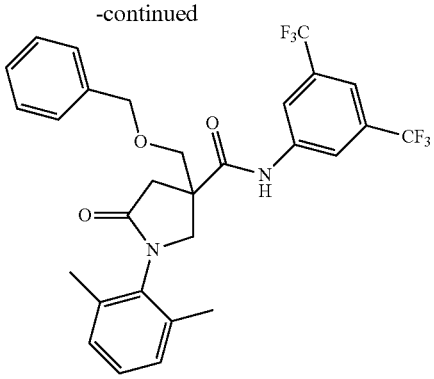

a) LHMDS (1 M solution in THF, 9.72 mL, 9.72 mmol) was added slowly to a cooled (−50° C.) solution of 1-(2,6-dimethylphenyl)-5-oxo-pyrrolidine-3-carboxylic acid methyl ester (2 g, 8.09 mmol) in THF (50 mL). The solution was stirred at −50° C. for 5 min then warmed to 0° C. and stirred for a further 5 min. After cooling back to −50° C., BOMCl (~90% pure, 2.46 mL, 17.8 mmol) was added and the resulting reaction mixture was warmed to room temperature and stirred for 2 h. Saturated aqueous NH$_4$Cl solution (25 mL) was added, and the aqueous solution was extracted with EtOAc (3×75 mL). The combined organic layer were washed with water (100 mL), brine (100 mL), dried (Na$_2$SO$_4$) and evaporated. The residue was purified by automated flash chromatography (SiO$_2$, 10→50% EtOAc/hexanes) to give 3-benzyloxymethyl-1-(2,6-dimethylphenyl)-5-oxo-pyrrolidine-3-carboxylic acid methyl ester (653 mg, 22% yield). LC-MS: R$_t$ (retention time): 2.72 min, MS: (ES) m/z 368.1 (M+H$^+$).

b) n-BuLi (2.8 M solution in hexanes, 183 µL, 0.513 mmol) was added to a cooled (−50° C.) solution of 3,5-bis-trifluoromethylaniline (84.5 µL, 0.545 mmol) in THF (3 mL). The resulting dark brown colored solution was slowly warmed to room temperature and stirred for an hour. A solution of 3-benzyloxymethyl-1-(2,6-dimethylphenyl)-5-oxo-pyrrolidine-3-carboxylic acid methyl ester (prepared from step a, 100 mg, 0.27 mmol) in THF (2 mL) was added and the solution was stirred for 2 h at 70° C. The reaction mixture was then cooled to room temperature, AcOH (100 µL) was added and the solution was purified by automated flash chromatography (SiO$_2$, 10→50% EtOAc/hexanes) followed by preparative HPLC (15→85% gradient of MeCN—H$_2$O with 0.1% TFA). The pure fractions were lyophilized to afford 3-benzyloxymethyl-1-(2,6-dimethylphenyl)-5-oxo-pyrrolidine-3-carboxylic acid (3,5-bis-trifluoromethylphenyl)-amide (15 mg, 10% yield). LC-MS: R$_t$ (retention time): 3.38 min, MS: (ES) m/z 565.2 (M+H$^+$). $^1$H NMR (400 MHz, DMSO-d$_6$) δ 10.2 (s, 1H), 8.28 (s, 2H), 7.8 (s, 1H), 7.2-7.28 (m, 5H), 7.05-7.15 (m, 3H), 4.5-4.58 (m, 2H), 4.03 (d, 1H, J=8 Hz), 3.86-3.92 (m, 2H), 3.6 (d, 1H, J=8 Hz), 3.08 (d, 1H, J=16 Hz), 2.64 (d, 1H, J=16 Hz), 2.05 (s, 3H), 2.06 (s, 3H).

Example 18

Synthesis of 3-cyclopentyl-1-(2,6-dimethylphenyl)-5-oxo-pyrrolidine-3-carboxylic acid (3,5-bis-trifluoromethylphenyl)amide

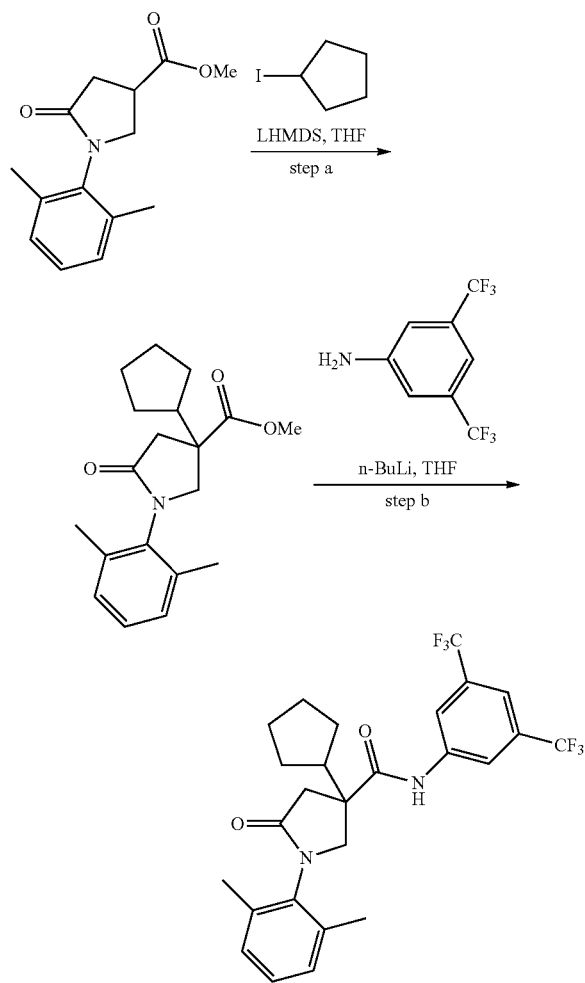

a) LHMDS (1 M solution in THF, 2.4 mL, 2.4 mmol) was added slowly to a cooled (−50° C.) solution of 1-(2,6-dimethylphenyl)-5-oxo-pyrrolidine-3-carboxylic acid methyl ester (494 mg, 2 mmol) in THF (5 mL). Stirred at −50° C. for 5 min then warmed to 0° C. and stirred further for 5 min. After cooling back to −50° C., iodocyclopentane (462.5 μL, 4 mmol) was added and the resulting reaction mixture was warmed to room temperature and stirred for 2 h. Saturated aqueous NH₄Cl solution (10 mL) was added, and the aqueous solution was extracted with EtOAc (3×25 mL). The combined organic layer was washed with water (50 mL), brine (50 mL), dried (Na₂SO₄) and evaporated. The residue was purified by flash chromatography (SiO₂, 20→50% EtOAc/hexanes) to give 3-cyclopentyl-1-(2,6-dimethylphenyl)-5-oxo-pyrrolidine-3-carboxylic acid methyl ester (120 mg, 19% yield). LC-MS: $R_t$ (retention time): 2.54 min, MS: (ES) m/z 316.4 (M+H⁺).

b) n-BuLi (2.5 M solution in hexanes, 456 μL, 1.14 mmol) was added to a solution of 3,5-bis-trifluoromethylaniline (177 μL, 0.1.14 mmol) in THF (3 mL) at room temperature. The resulting dark brown colored solution was stirred for 10 min at room temperature. A solution of 3-cyclopentyl-1-(2,6-dimethylphenyl)-5-oxo-pyrrolidine-3-carboxylic acid methyl ester (prepared from step a, 120 mg, 0.38 mmol) in THF (2 mL) was added and stirred for 2 h at 70° C. The reaction mixture was then purified by automated flash chromatography. Pure fractions were combined and concentrated under reduced pressure. The material was recrystallized from MeOH to obtain the desired product 3-cyclopentyl-1-(2,6-dimethylphenyl)-5-oxo-pyrrolidine-3-carboxylic acid (3,5-bis-trifluoromethyl-phenyl)-amide (60 mg, 31% yield) as white crystals. LC-MS: R, (retention time): 3.32 min, MS: (ES) m/z 513.2 (M+H⁺). ¹H NMR (400 MHz, CDCl₃) δ 8.4 (s, 1H), 8.05 (s, 2H), 7.6 (s, 1H), 7.08-7.13 (m, 2H), 7.02-7.06 (m, 2H), 4.14 (d, 1H, J=11.5 Hz), 3.56 (d, 1H, J=11.5 Hz) 3.17 (d, 1H, J=16.9 Hz), 2.74 (d, 1H, J=16.9 Hz), 2.42-2.52 (m, 1H), 2.2 (s, 3H), 2.14 (s, 3H), 1.75-1.88 (m, 2H), 1.6-1.68 (m, 4H), 1.25-1.48 (m, 2H).

Example 19

Synthesis of cis-1-(2,6-dimethylphenyl)-3-ethyl-4-methoxy-5-oxo-pyrrolidine-3-carboxylic acid (3,5-bis-trifluoromethylphenyl)-amide

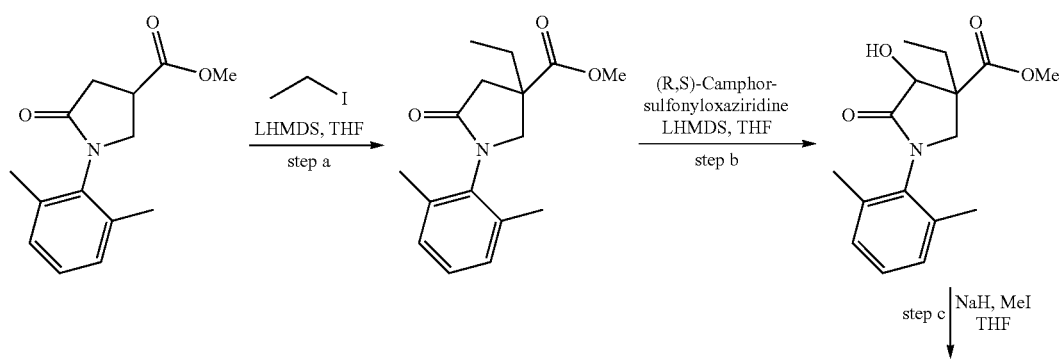

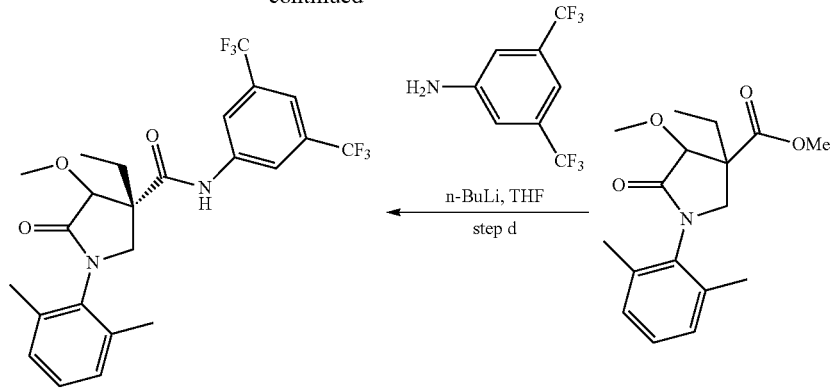

a) LHMDS (1 M solution in THF, 24.3 mL, 24.3 mmol) was added slowly to a cooled (−50° C.) solution of 1-(2,6-dimethylphenyl)-5-oxo-pyrrolidine-3-carboxylic acid methyl ester (5 g, 20.24 mmol) in THF (25 mL). The solution was stirred at −50° C. for 5 min then warmed to 0° C. and stirred further for 5 min. After cooling back to −50° C., iodoethane (3.27 mL, 40.48 mmol) was added and the resulting reaction mixture was warmed to room temperature and stirred for 2 h. Saturated aqueous NH$_4$Cl solution (50 mL) was added, and the solution was extracted with EtOAc (3×100 mL). The combined organic layer were washed with water (100 mL), brine (100 mL), dried (Na$_2$SO$_4$) and evaporated. The residue was purified by flash chromatography (SiO$_2$, 20→50% EtOAc/hexanes) to give 1-(2,6-dimethylphenyl)-3-ethyl-5-oxo-pyrrolidine-3-carboxylic acid methyl ester (3.3 g, 59% yield). LC-MS: R$_t$ (retention time): 2.21 min, MS: (ES) m/z 276.1 (M+H$^+$).

b) LHMDS (1 M solution in THF, 6 mL, 6 mmol) was added slowly to a cooled (−50° C.) solution of 1-(2,6-dimethylphenyl)-3-ethyl-5-oxo-pyrrolidine-3-carboxylic acid methyl ester (prepared from step a, 1.1 g, 4 mmol) in THF (15 mL). The solution was stirred at −50° C. for 5 min then warmed to 0° C. and stirred for an additional 5 min. After cooling back to −50° C., (R,S)-camphorsulfonyloxaziridine (1.1 g, 4.8 mmol) was added and the resulting reaction mixture was warmed to room temperature and stirred for 2 h. Saturated aqueous NH$_4$Cl solution (30 mL) was added, and the solution was extracted with EtOAc (3×75 mL). The combined organic layers were washed with water (50 mL), brine (50 mL), dried (Na$_2$SO$_4$) and concentrated under reduced pressure. The residue was purified by flash chromatography (SiO$_2$, 30→70% EtOAc/hexanes) to give 1-(2,6-dimethylphenyl)-3-ethyl-4-hydroxy-5-oxo-pyrrolidine-3-carboxylic acid methyl ester (1.1 g, quantitative yield). LC-MS: R$_t$ (retention time): 1.89 min, MS: (ES) m/z 292.1 (M+H$^+$).

c) NaH (60% dispersed in mineral oil, 50 mg, ~2.0 mmol) was added slowly to a cooled (0° C.) solution of 1-(2,6-dimethylphenyl)-3-ethyl-4-hydroxy-5-oxo-pyrrolidine-3-carboxylic acid methyl ester (prepared from step b, 146 mg, 0.5 mmol) in THF (5 mL). After stirring for 5 min, MeI (62.5 μL, 1 mmol) was added and the resulting reaction mixture was slowly warmed to room temperature and stirred further for 12 h. Saturated aqueous NH$_4$Cl solution (10 mL) was added, and the solution was extracted with EtOAc (3×25 mL). The combined organic layer were washed with water (50 mL), brine (50 mL), dried (Na$_2$SO$_4$) and evaporated. The residue was purified by flash chromatography (SiO$_2$, 10→50% EtOAc/hexanes) to give 1-(2,6-dimethylphenyl)-3-ethyl-4-methoxy-5-oxo-pyrrolidine-3-carboxylic acid methyl ester (70 mg, 46% yield). LC-MS: R$_t$ (retention time): 2.31, 2.44 min (two diastereomers), MS: (ES) m/z 306.2 (M+H$^+$).

d) n-BuLi (2.5 M solution in hexanes, 300 μL, 0.688 mmol) was added to a solution of 3,5-bis-trifluoromethylaniline (107 μL, 0.688 mmol) in THF (3 mL) at room temperature. The resulting dark brown colored solution was stirred for 10 min at room temperature. A solution of 1-(2,6-dimethylphenyl)-3-ethyl-4-methoxy-5-oxo-pyrrolidine-3-carboxylic acid methyl ester (prepared from step c, 70 mg, 0.229 mmol) in THF (2 mL) was added and stirred for 2 h at 70° C. Saturated aqueous NH$_4$Cl solution (5 mL) was added, and the solution was extracted with EtOAc (3×25 mL). The combined organic layers were washed with water (25 mL), brine (25 mL), dried (Na$_2$SO$_4$) and evaporated. The residue was then purified by automated flash chromatography (SiO$_2$, 10→50% EtOAc/hexanes). Pure fractions were combined and concentrated under reduced pressure. The obtained product was further purified by preparative HPLC (30→85% gradient of MeCN—H$_2$O with 0.1% TFA). The pure fractions were lyophilized to afford cis-1-(2,6-dimethyl-phenyl)-3-ethyl-4-methoxy-5-oxo-pyrrolidine-3-carboxylic acid (3,5-bis-trifluoromethyl-phenyl)-amide (10 mg, 9% yield). LC-MS: R$_t$ (retention time): 3.24 min, MS: (ES) m/z 503.1 (M+H$^+$). $^1$H NMR (400 MHz, CDCl$_3$) δ 8.25 (s, 1H), 8.0 (s, 2H), 7.62 (s, 1H), 7.05-7.18 (m, 3H), 4.27 (s, 1H), 3.95-4.02 (m, 4H), 3.45 (d, 1H, J=11.85 Hz), 2.26 (s, 3H), 2.18 (s, 3H), 1.92-2.02 (m, 2H), 1.02 (t, 3H, J=6.5 Hz).

Example 20

Synthesis of 3-cyclobutyl-1-(2,6-dimethylphenyl)-5-oxo-pyrrolidine-3-carboxylic acid (3,5-bis-trifluoromethylphenyl)-amide

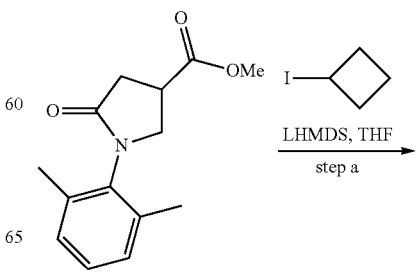

-continued

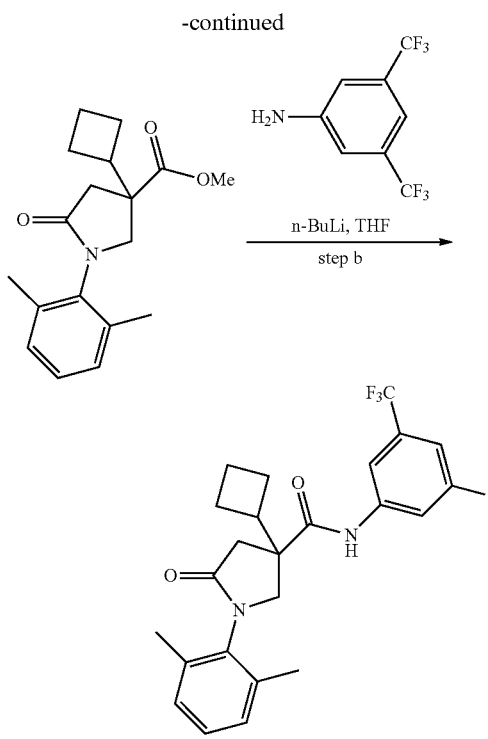

a) LHMDS (1 M solution in THF, 2.4 mL, 2.4 mmol) was added slowly to a cooled (−50° C.) solution of 1-(2,6-dimethylphenyl)-5-oxo-pyrrolidine-3-carboxylic acid methyl ester (494 mg, 2 mmol) in THF (5 mL). Stirred at −50° C. for 5 min then warmed to 0° C. and stirred for 5 min. After cooling back to −50° C., iodocyclobutane (736 mg, 4 mmol) was added and the resulting reaction mixture was warmed to room temperature and stirred for 2 h. Saturated aqueous NH$_4$Cl solution (10 mL) was added, extracted with EtOAc (3×25 mL). The combined organic layer was washed with water (50 mL), brine (50 mL), dried (Na$_2$SO$_4$) and evaporated to give crude product 3-cyclobutyl-1-(2,6-dimethyl-phenyl)-5-oxo-pyrrolidine-3-carboxylic acid methyl ester which was taken on directly to the next step. MS: (ES) m/z 302.3 (M+H$^+$).

b) n-BuLi (2.5 M solution in hexanes, 1.13 mL, 2.82 mmol) was added to a solution of 3,5-bis-trifluoromethylaniline (437 μL, 2.82 mmol) in THF (0.5 mL) at room temperature. The resulting dark brown colored solution was stirred for 10 min at room temperature. A solution of 3-cyclobutyl-1-(2,6-dimethylphenyl)-5-oxo-pyrrolidine-3-carboxylic acid methyl ester (prepared from step a, 283 mg, 0.94 mmol) in THF (3 mL) was added and stirred for 30 min at 100° C. in a sealed vial. Saturated aqueous NH$_4$Cl solution (10 mL) was added, extracted with EtOAc (3×25 mL). The combined organic layer was washed with water (40 mL), brine (40 mL), dried (Na$_2$SO$_4$) and evaporated. The reaction mixture was then purified by automated flash chromatography (SiO$_2$, 20→70% EtOAc/hexanes). Selected fractions were combined and concentrated under reduced pressure. The obtained product was further purified twice by preparative HPLC (5→90% gradient of MeCN—H$_2$O with 0.1% TFA) to obtain the desired product 3-cyclobutyl-1-(2,6-dimethylphenyl)-5-oxo-pyrrolidine-3-carboxylic acid (3,5-bis-trifluoromethylphenyl)-amide (7 mg, 1.5% yield). LC-MS: R$_t$ (retention time): 3.17 min, MS: (ES) m/z 499.1 (M+H$^+$). $^1$H NMR (400 MHz, CDCl$_3$) δ 8.08 (s, 3H), 7.63 (s, 1H), 7.12-7.16 (m, 1H), 7.04-7.09 (m, 2H), 4.18 (d, 1H, J=8.5 Hz), 3.58 (d, 1H, J=8.5 Hz), 3.18 (d, 1H, J=17 Hz), 2.8 (d, 1H, J=17 Hz), 2.2 (s, 3H), 2.17 (s, 3H), 1.85-2.0 (m, 2H), 0.68-0.8 (m, 1H), 0.5-0.62 (m, 2H), 0.15-0.2 (m, 2H).

Example 21

Synthesis of cis-1-(2,6-dimethylphenyl)-3-isobutyl-4-methyl-5-oxo-pyrrolidine-3-carboxylic acid (3,5-bis-trifluoromethylphenyl)-amide

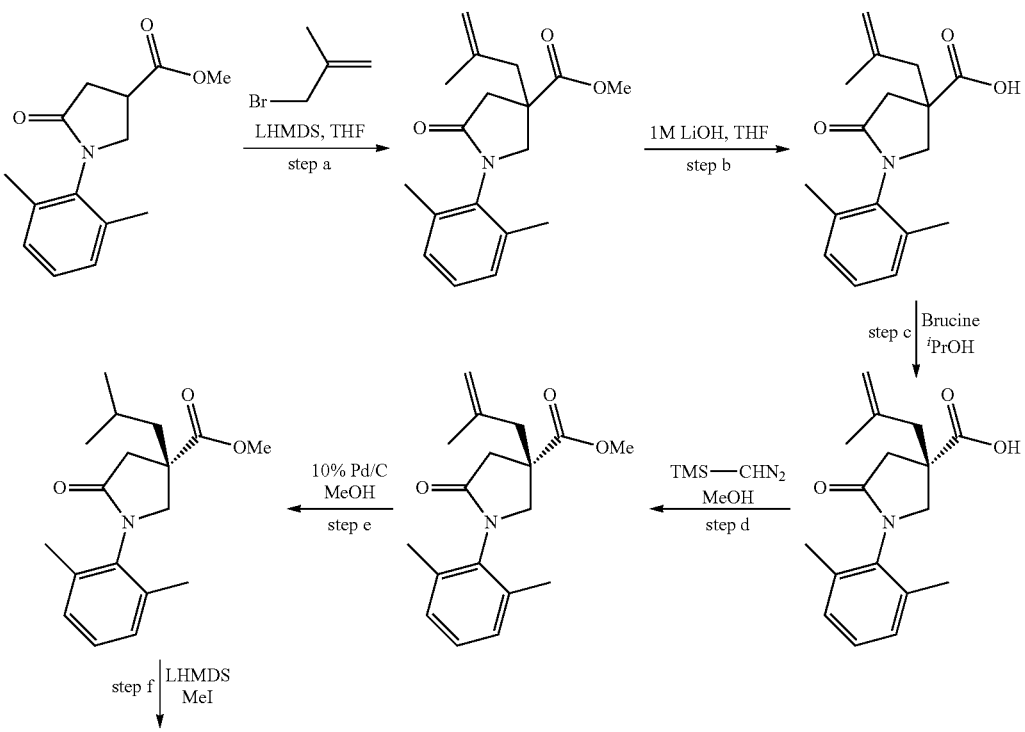

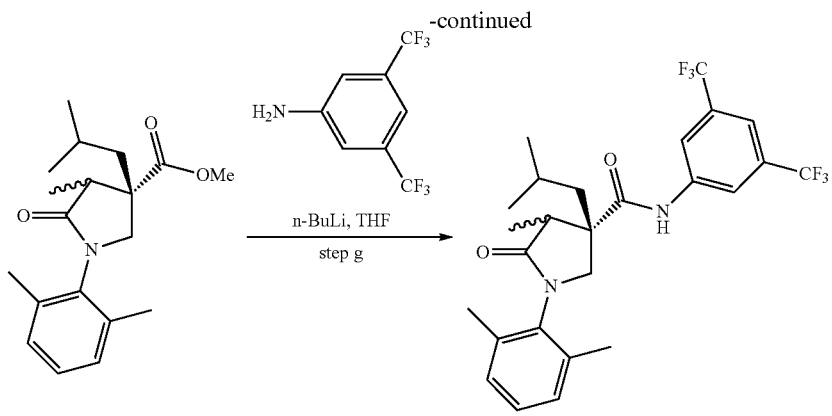

a) LHMDS (1 M solution in THF, 83 mL, 83 mmol) was added slowly to a cooled (−50° C.) solution of 1-(2,6-dimethylphenyl)-5-oxo-pyrrolidine-3-carboxylic acid methyl ester (17 g, 68.83 mmol) in THF (170 mL). After 5 min, 3-bromo-2-methylpropene (13.8 mL, 136.8 mmol) was added slowly at −50° C. and the resulting reaction mixture was warmed to room temperature and stirred for 2 h. Saturated aqueous NH$_4$Cl solution (50 mL) was added, and the aqueous was extracted with EtOAc (3×100 mL). The combined organic layers were washed with water (100 mL), brine (100 mL), dried (Na$_2$SO$_4$) and evaporated. The residue was purified by automated flash chromatography (SiO$_2$, 20→60% MTBE/hexanes) to give 1-(2,6-dimethylphenyl)-3-(2-methylallyl)-5-oxo-pyrrolidine-3-carboxylic acid methyl ester (10.9 g, 53% yield). LC-MS: R$_t$ (retention time): 2.44 min, MS: (ES) m/z 302.1 (M+H$^+$).

b) To a solution of 1-(2,6-dimethylphenyl)-3-(2-methylallyl)-5-oxo-pyrrolidine-3-carboxylic acid methyl ester (prepared from step a, 10.9 g, 36.21 mmol) in MeOH (100 mL) was added 1M LiOH (100 mL, 100 mmol) and the resulting clear solution was refluxed (70° C.) for an hour. The reaction mixture was then cooled to room temperature, MeOH was removed under reduced pressure and the obtained basic aqueous solution was added to a cooled (0° C.) 2N HCl (200 mL) with vigorous stirring. The resulting white solid was filtered, washed with water (3×300 mL), heptane (200 mL) and dried under high vacuum to obtain 1-(2,6-dimethylphenyl)-3-(2-methylallyl)-5-oxo-pyrrolidine-3-carboxylic acid (10 g, quantitative yield). LC-MS: R$_t$ (retention time): 1.98 min, MS: (ES) m/z 288.1 (M+H$^+$).

c) To a mixture of 1-(2,6-dimethylallyl)-5-oxo-pyrrolidine-3-carboxylic acid (prepared from step b, 9 g, 31.36 mmol) and brucine (12.37 g, 31.35 mmol) was added $^i$PrOH (75 mL) and heated with stirring at 75° C. until it became a clear solution, which was then allowed to cool to room temperature slowly. The resulting white solid was filtered and discarded. The filtrate was then diluted with Et$_2$O (100 mL) and washed with 2 N HCl (2×100 mL), dried (Na$_2$SO$_4$) and concentrated under reduced pressure to obtain (S)-1-(2,6-dimethyl-phenyl)-3-(2-methyl-allyl)-5-oxo-pyrrolidine-3-carboxylic acid (550 mg, enantiomeric ratio: 9:1, with the enantiomeric ratio determined using a RegisWhelk® chiral analytical column and 10% EtOH in hexanes isocratic solvent system, flow rate: 1 mL/min, 30 min run). Further recrystallization of the above carboxylic acid derivative from hot toluene/dioxane (9:1, 14 mL) enriched the enantiomeric ratio to 99.2:0.8 and afforded 430 mg of (S)-1-(2,6-dimethylphenyl)-3-(2-methylallyl)-5-oxo-pyrrolidine-3-carboxylic acid.

d) To a solution of (S)-1-(2,6-dimethylphenyl)-3-(2-methylallyl)-5-oxo-pyrrolidine-3-carboxylic acid (prepared from c, 430 mg, 1.49 mmol) in MeOH (5 mL) was added TMS-CHN$_2$ (2.24 mL, 4.49 mmol, 2 M solution in hexanes) dropwise. After stirring the yellow colored clear solution at room temperature for 10 min, MeOH was removed under reduced pressure, and the solution was diluted with EtOAc (50 mL) and washed with saturated NaHCO$_3$ solution (25 mL), water (25 mL), brine (25 mL), dried (Na$_2$SO$_4$) and evaporated to obtain (S)-1-(2,6-dimethyl-phenyl)-3-(2-methyl-allyl)-5-oxo-pyrrolidine-3-carboxylic acid methyl ester (474 mg) which was used as such in next step without any further purification. LC-MS: R$_t$ (retention time): 2.14 min, MS: (ES) m/z 302.3 (M+H$^+$).

e) 10% Pd/C (120 mg) was added to a solution of (S)-1-(2,6-dimethyl-phenyl)-3-(2-methyl-allyl)-5-oxo-pyrrolidine-3-carboxylic acid methyl ester (prepared from step d, 474 mg, 1.57 mmol) in MeOH (5 mL) and resulting black suspension was stirred at room temperature overnight under H$_2$ gas using a balloon. The reaction mixture was then diluted with EtOAc (25 mL) and filtered through celite, washed with MeOH (25 mL) and volatiles from filtrate were evaporated to obtain crude product which was purified by flash chromatography (SiO$_2$, 20→60% EtOAc/hexanes) to obtain (S)-1-(2,6-dimethyl-phenyl)-3-isobutyl-5-oxo-pyrrolidine-3-carboxylic acid methyl ester (450 mg, 94% yield). LC-MS: R$_t$ (retention time): 2.55 min, MS: (ES) m/z 304.1 (M+H$^+$).

f) LHMDS (1 M solution in THF, 1.78 mL, 1.78 mmol) was added slowly to a cooled (−50° C.) solution of (S)-1-(2,6-dimethylphenyl)-3-isobutyl-5-oxo-pyrrolidine-3-carboxylic acid methyl ester (prepared from step e, 450 mg, 1.48 mmol) in THF (10 mL). After 5 min, iodomethane (185 µL, 2.97 mmol) was added at −50° C. and the resulting reaction mixture was immediately warmed to room temperature and stirred further for 2 h. Saturated aqueous NH$_4$Cl solution (25 mL) was added, and the solution was extracted with EtOAc (3×50 mL). The combined organic layers were washed with water (50 mL), brine (50 mL), dried (Na$_2$SO$_4$) and evaporated. The residue was purified by flash chromatography (SiO$_2$, 20→60% MTBE/hexanes) to give (S)-1-(2,6-dimethylphenyl)-3-isobutyl-4-methyl-5-oxo-pyrrolidine-3-carboxylic acid methyl ester (130 mg, 28% yield). LC-MS: R, (retention time): 2.68 min, MS: (ES) m/z 318.2 (M+H$^+$).

g) n-BuLi (2.5 M solution in hexanes, 0.492 mL, 1.23 mmol) was added to a solution of 3,5-bis-trifluoromethylaniline (492 µL, 1.23 mmol) in THF (3 mL) at room temperature. The resulting dark brown colored solution was stirred for 10 min at room temperature. A solution of (S)-1-(2,6-dimethylphenyl)-3-isobutyl-4-methyl-5-oxo-pyrrolidine-3-carboxylic acid methyl ester (prepared from step f, 130 mg, 0.41 mmol) in THF (3 mL) was added and stirred overnight at 75° C. in a sealed vial. Saturated aqueous NH₄Cl solution (10 mL) was added, and the solution was extracted with EtOAc (3×25 mL). The combined organic layers were washed with water (30 mL), brine (30 mL), dried (Na₂SO₄) and evaporated. The reaction mixture was then purified by flash chromatography (SiO₂, 20→70% EtOAc/hexanes). Selected fractions were combined and concentrated under reduced pressure. The obtained product was further purified by preparative HPLC (50→90% gradient of MeCN—H₂O with 0.1% TFA) and pure fractions were lyophilized to obtain desired product cis-1-(2,6-dimethyl-phenyl)-3-isobutyl-4-methyl-5-oxo-pyrrolidine-3-carboxylic acid (3,5-bis-trifluoromethyl-phenyl)-amide (45 mg, 21% yield). LC-MS: $R_t$ (retention time): 3.26 min, MS: (ES) m/z 515.2 (M+H⁺). ¹H NMR (400 MHz, DMSO-d₆) δ 10.38 (s, 1H), 8.35 (s, 2H), 7.8 (s, 1H), 7.02-7.14 (m, 3H), 4.04 (d, 1H, J=9.9 Hz), 3.68 (d, 1H, J=9.9 Hz), 3.05-3.13 (m, 1H), 2.12 (s, 3H), 1.98 (s, 3H), 1.78-1.95 (m, 2H), 1.53-1.65 (m, 1H), 1.3 (d, 3H, J=7.4 Hz), 0.82-0.88 (m, 6H).

Example 22

Synthesis of cis-1-(2,6-dimethylphenyl)-3-[(ethylmethylamino)-ethyl]-4-methyl-5-oxo-pyrrolidine-3-carboxylic acid (3,5-bis-trifluoromethylphenyl)-amide

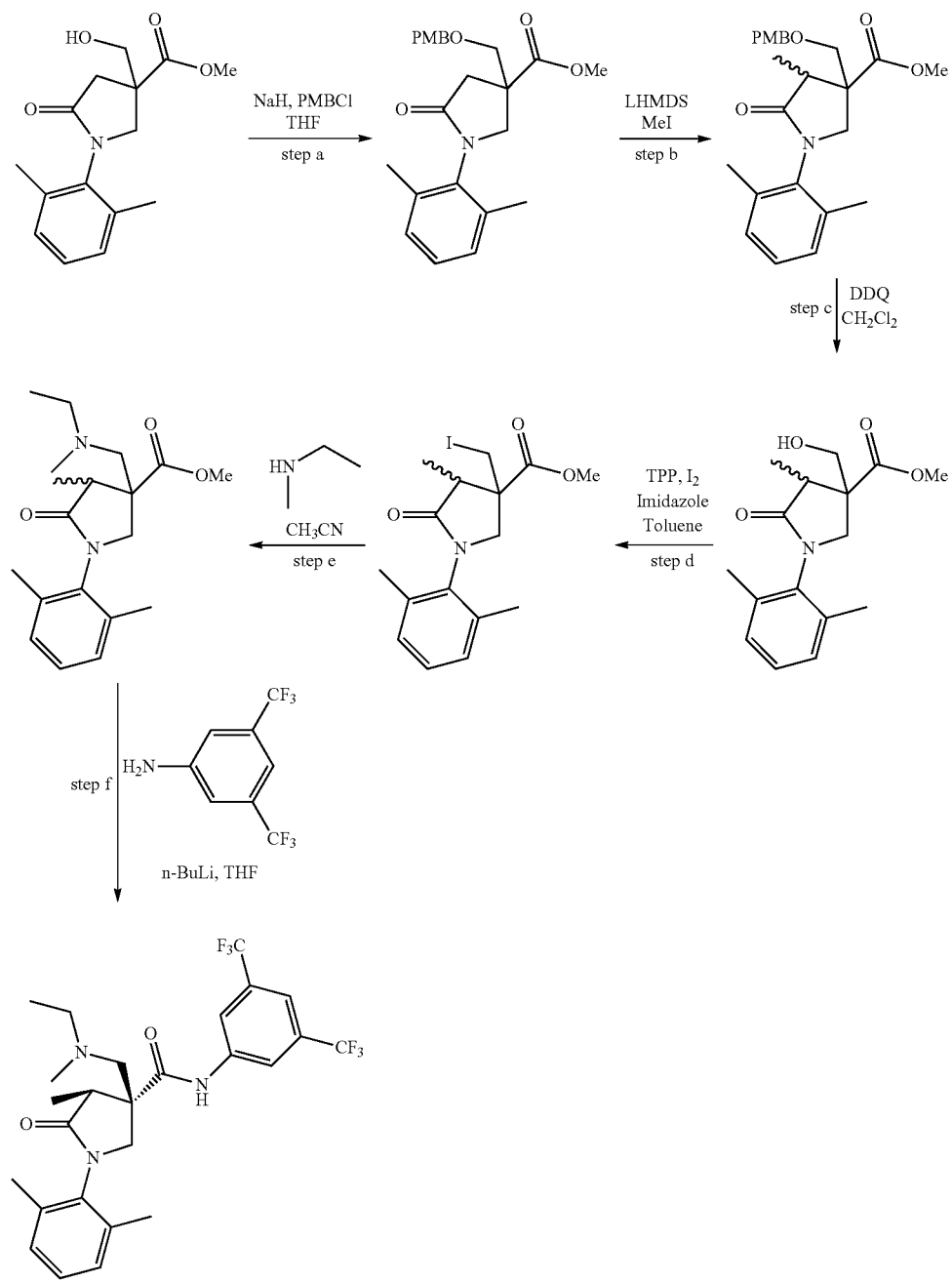

a) NaH (60% dispersed in mineral oil, 260 mg, 5.41 mmol) was added slowly to a cooled (0° C.) solution of 1-(2,6-dimethylphenyl)-3-hydroxymethyl-5-oxo-pyrrolidine-3-carboxylic acid methyl ester (prepared in the above examples, 1 g, 3.61 mmol) in THF (10 mL). After stirring for 5 min, PMBCl (737 µL, 5.41 mmol) was added and the resulting reaction mixture was slowly warmed to room temperature and stirred further for 2 h. Saturated aqueous NH$_4$Cl solution (10 mL) was added, and the solution was extracted with EtOAc (3×25 mL). The combined organic layers were washed with water (30 mL), brine (30 mL), dried (Na$_2$SO$_4$) and evaporated. The residue was purified by flash chromatography (SiO$_2$, 10→60% EtOAc/hexanes) to give 1-(2,6-dimethyl-phenyl)-3-(4-methoxy-benzyloxymethyl)-5-oxo-pyrrolidine-3-carboxylic acid methyl ester (767 mg, 54% yield). LC-MS: R$_t$ (retention time): 2.37 min, MS: (ES) m/z 398.3 (M+H$^+$).

b) LHMDS (1 M solution in THF, 2.32 mL, 2.32 mmol) was added slowly to a cooled (−50° C.) solution of 1-(2,6-dimethylphenyl)-3-(4-methoxybenzyloxymethyl)-5-oxo-pyrrolidine-3-carboxylic acid methyl ester (prepared from step a, 767 mg, 1.93 mmol) in THF (7 mL). After 5 min, iodomethane (602 µL, 9.65 mmol) was added at −50° C. and the resulting reaction mixture was warmed to room temperature and stirred further for 2 h. Saturated aqueous NH$_4$Cl solution (25 mL) was added, and the solution was extracted with EtOAc (3×50 mL). The combined organic layers were washed with water (75 mL), brine (75 mL), dried (Na$_2$SO$_4$) and evaporated. The residue was purified by flash chromatography (SiO$_2$, 20→70% EtOAc/hexanes) to give 1-(2,6-dimethylphenyl)-3-(4-methoxybenzyloxymethyl)-4-methyl-5-oxo-pyrrolidine-3-carboxylic acid methyl ester (736 mg, 93% yield). LC-MS: R$_t$ (retention time): 2.39 min, MS: (ES) m/z 412.4 (M+H$^+$).

c) To a vigorously stirring mixture of 1-(2,6-dimethylphenyl)-3-(4-methoxy-benzyloxymethyl)-4-methyl-5-oxo-pyrrolidine-3-carboxylic acid methyl ester (prepared from step b, 736 mg, 1.79 mmol) in 5:1 CH$_2$Cl$_2$/H$_2$O (12 mL) was added 2,3-dichloro-5,6-dicyanobenzoquinone (609.5 mg, 2.68 mmol) at room temperature and stirred for 2 h at the same temperature. The reaction mixture was diluted with CH$_2$Cl$_2$ (25 mL) and filtered through celite, washed with CH$_2$Cl$_2$ (3×25 mL). The filtrate was then washed with saturated NaHCO$_3$ solution (3×30 mL), water (30 mL), brine (30 mL), dried and evaporated. The obtained residue was purified by flash chromatography (SiO$_2$, 20→70% EtOAc/hexanes) to give 1-(2,6-dimethylphenyl)-3-hydroxymethyl-4-methyl-5-oxo-pyrrolidine-3-carboxylic acid methyl ester (373 mg, 72% yield). LC-MS: R, (retention time): 1.2 min, MS: (ES) m/z 292.2 (M+H$^+$).

d) Imidazole (261.5 mg, 3.84 mmol), triphenylphosphine (670.7 mg, 2.56 mmol) and I$_2$ (487.3 mg, 1.92 mmol) were added sequentially to a solution of 1-(2,6-dimethylphenyl)-3-hydroxymethyl-4-methyl-5-oxo-pyrrolidine-3-carboxylic acid methyl ester (prepared from step c, 373 mg, 1.28 mmol) in toluene (15 mL) and resulting reaction mixture was heated at 100° C. with stirring for an hour. The reaction mixture was then cooled to room temperature and diluted with EtOAc (50 mL), washed with water (30 mL), saturated NH$_4$Cl (30 mL), dried (Na$_2$SO$_4$) and evaporated. The residue was then purified by flash chromatography (SiO$_2$, 20→70% EtOAc/hexanes) to obtain 1-(2,6-dimethylphenyl)-3-iodomethyl-4-methyl-5-oxo-pyrrolidine-3-carboxylic acid methyl ester (427 mg, 83% yield). LC-MS: R$_t$ (retention time): 2.32 min, MS: (ES) m/z 402.2 (M+H$^+$).

e) To a solution of 1-(2,6-dimethylphenyl)-3-iodomethyl-4-methyl-5-oxo-pyrrolidine-3-carboxylic acid methyl ester (prepared from step d, 100 mg, 0.25 mmol) in CH$_3$CN (3 mL) was added N-ethylmethylamine (215 µL, 2.5 mmol) and stirred at 80° C. for overnight. Volatiles were evaporated under reduced pressure and purified by automated flash chromatography (SiO$_2$, 20→70% EtOAc/hexanes) to obtain 1-(2,6-dimethyl-phenyl)-3-[(ethylmethylamino)-methyl]-4-methyl-5-oxo-pyrrolidine-3-carboxylic acid methyl ester (10 mg, 12% yield). LC-MS: R$_t$ (retention time): 0.61 min, MS: (ES) m/z 333.3 (M+H$^+$).

f) n-BuLi (2.5 M solution in hexanes, 50 µL, 0.09 mmol) was added to a solution of 3,5-bis-trifluoromethylaniline (20 µL, 0.09 mmol) in THF (2 mL) at room temperature. The resulting dark brown colored solution was stirred for 10 min at room temperature. A solution of 1-(2,6-dimethylphenyl)-3-[(ethylmethylamino)methyl]-4-methyl-5-oxo-pyrrolidine-3-carboxylic acid methyl ester (prepared from step e, 10 mg, 0.03 mmol) in THF (2 mL) was added and stirred for 2 h at 70° C. in a sealed vial. Saturated aqueous NH$_4$Cl solution (10 mL) was added, and the solution was extracted with EtOAc (3×25 mL). The combined organic layers were washed with water (20 mL), brine (20 mL), dried (Na$_2$SO$_4$) and evaporated. The residue was purified by preparative HPLC (50→90% gradient of MeCN—H$_2$O with 0.1% TFA) and pure fractions were lyophilized to obtain desired product cis-1-(2,6-dimethylphenyl)-3-[(ethylmethylamino)methyl]-4-methyl-5-oxo-pyrrolidine-3-carboxylic acid (3,5-bis-trifluoromethylphenyl)-amide (5 mg, 25% yield). LC-MS: R$_t$ (retention time): 2.9 min, MS: (ES) m/z 530.5 (M+H$^+$). $^1$H NMR (400 MHz, CDCl$_3$) δ 10.75 (s, 1H), 8.26 (s, 2H), 7.65 (s, 1H), 7.16-7.2 (m, 1H), 7.05-7.1 (m, 2H), 4.26 (d, 1H, J=10.7 Hz), 4.0 (d, 1H, J=10.7 Hz), 3.55-3.62 (m, 1H), 3.34-3.44 (m, 2H), 3.15-3.28 (m, 2H), 2.85 (s, 3H), 2.24 (s, 3H), 2.13 (s, 3H), 1.54 (d, 3H, J=7.14 Hz), 1.39 (t, 3H, J=6.5 Hz).

Example 23

(3R,4S)-3-((4,4-difluoropiperidin-1-yl)methyl)-1-(2,6-dimethylphenyl)-N-(3-isopropoxy-5-(trifluoromethyl)phenyl)-4-methyl-5-oxopyrrolidine-3-carboxamide

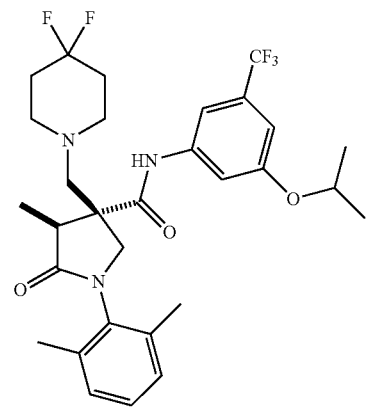

(3R,4S)-3-((4,4-difluoropiperidin-1-yl)methyl)-1-(2,6-dimethylphenyl)-N-(3-isopropoxy-5-(trifluoromethyl)phenyl)-4-methyl-5-oxopyrrolidine-3-carboxamide was prepared in a similar fashion as Example 22. $^1$H NMR (400 MHZ, DMSO): δ 9.93 (s, 1H), 7.55 (d, J=11.7 Hz, 2H), 7.07-7.14 (m, 3H), 6.91 (s, 1H), 4.65 (septet, J=5.9 Hz, 1H), 4.07 (d, J=10.3 Hz, 1H), 3.79 (d, J=10.3 Hz, 1H), 3.04-3.13 (m, 2H), 2.90 (d, J=13.9 Hz, 1H), 2.50-2.59 (m, 4H), 2.17 (s, 3H), 2.06 (s, 3H), 1.74-1.94 (m, 4H), 1.26-1.32 (m, 9H). LC-MS R$_t$ (retention time): 2.96 min; MS: (ES) m/z 583 (M+H$^+$).

Example 24

(3R,4S)—N-(3,5-bis(trifluoromethyl)phenyl)-3-((cyclobutyl(methyl)amino)methyl)-1-(2,6-dimethylphenyl)-4-methyl-5-oxopyrrolidine-3-carboxamide

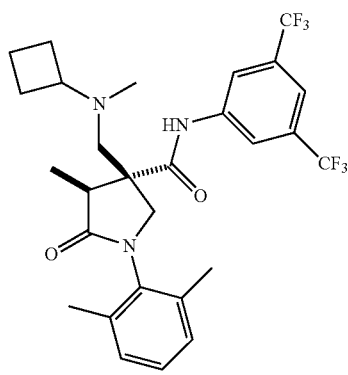

(3R,4S)—N-(3,5-bis(trifluoromethyl)phenyl)-3-((cyclobutyl(methyl)amino)methyl)-1-(2,6-dimethylphenyl)-4-methyl-5-oxopyrrolidine-3-carboxamide was prepared in a similar fashion as Example 22. $^1$H NMR (400 MHZ, DMSO): δ 10.6 (s, 1H), 8.30 (s, 2H), 7.81 (s, 1H), 7.05-7.15 (m, 3H), 4.13 (d, J=10.3 Hz, 1H), 3.79 (d, J=9.9 Hz, 1H), 3.11 (q, J=7.3 Hz, 1H), 2.97 (d, J=13.6 Hz, 1H), 2.86 (p, J=7.7 Hz, 1H), 2.64 (d, J=13.6 Hz, 1H), 2.16 (s, 3H), 2.04 (s, 3H), 2.01 (s, 3H), 1.88-1.97 (m, 2H), 1.66 (p, J=8.9 Hz, 2H), 1.42-1.52 (m, 2H), 1.32 (d, J=7.3 Hz, 3H). LC-MS R$_t$ (retention time): 2.33 min; MS: (ES) m/z 556 (M+H$^+$).

Example 25

Synthesis of N-(3,5-bis(trifluoromethyl)phenyl)-3-(1-hydroxyethyl)-1-(2,6-dimethylphenyl)-5-oxopyrrolidine-3-carboxamide

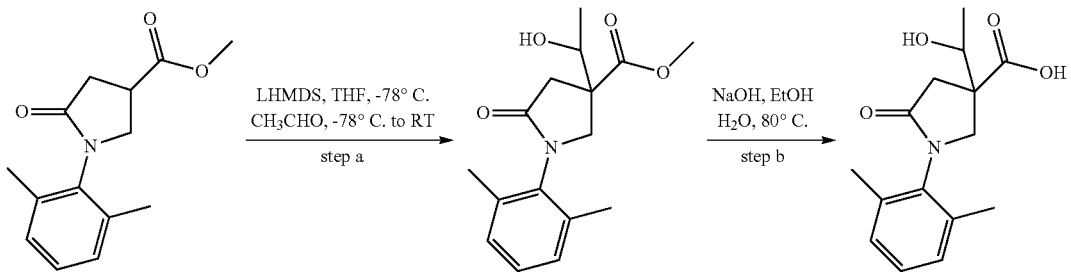

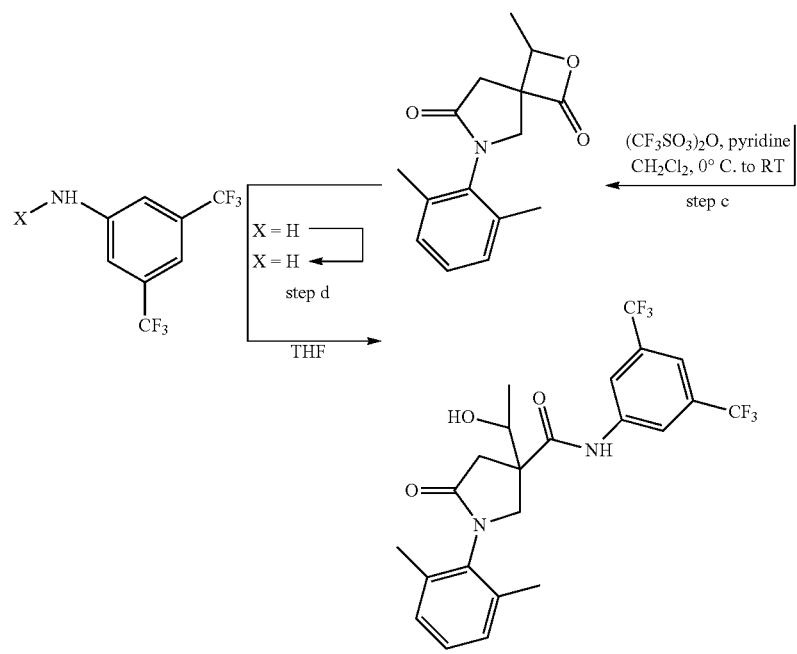

a) A solution of methyl 1-(2,6-dimethylphenyl)-5-oxopyrrolidine-3-carboxylate (8.1 g, 33 mmol) in 80 mL THF was cooled to −78° C. A solution of LHMDS (1.0 M in THF, 36 mL, 36 mmol) was added and the temperature was maintained at −78° C. for 80 min. Acetaldehyde (5.0 mL, 89 mmol) was then added and the reaction mixture was allowed to warm to room temperature. After 16 h, the reaction mixture was quenched with saturated aqueous NH$_4$Cl. The resulting aqueous layer was extracted with ethyl acetate, and the combined organic layers were dried (Na$_2$SO$_4$), filter65ed, and concentrated under reduced pressure. The resulting residue was purified by flash chromatography (SiO$_2$, 40-100% EtOAc/hexanes) to obtain the desired product in 24% yield (2.33 g). LC-MS R$_t$ (retention time): 1.27 min, MS: (ES) m/z 292 (M+H$^+$).

b) To a solution of the alcohol from step a (2.0 g, 6.9 mmol) in ethanol (25 mL) was added 1 M aqueous NaOH (50 mL). The mixture was stirred at 80° C. for 2 h. After ethanol was removed in vacuo, the solution was acidified with 6 M HCl, extracted with EtOAc, dried over MgSO$_4$, filtered and concentrated under reduced pressure to afford a friable foam (1.46 g, 76%). LC-MS R$_t$ (retention time): 0.62 min, MS: (ES) m/z 278 (M+H$^+$).

c) Trifluoromethanesulfonic anhydride (1.0 mL, 5.9 mmol) was added to a solution of the acid from step b (1.41 g, 5.1 mmol) in CH$_2$Cl$_2$ (20 mL) at 0° C. in the presence of pyridine (2 mL, 25 mmol). The reaction mixture was allowed to warm to room temperature and stirred for 16 h. The reaction mixture was washed with 1 M aqueous NaHSO$_4$ followed by saturated aqueous NaHCO$_3$. The organic layer was separated, dried over anhydrous MgSO$_4$, and concentrated under reduced pressure. Purification by flash chromatography (SiO$_2$, 60% EtOAc/hexanes) gave 600 mg (41% yield) of the product as a white solid. LC-MS R$_t$ (retention time): 1.71 min, MS: (ES) m/z 260 (M+H$^+$).

d) A solution of 3,5-bis(trifluoromethyl)aniline (1.2 g, 5.3 mmol) dissolved in THF (5 mL) was cooled to −78° C.; to this was added a solution of n-butyllithium (2.5 M in hexanes, 2.1 mL, 5.3 mmol). After 5 minutes, this solution was added to a solution of the lactone from step c in THF (5 mL). The reaction mixture was allowed to warm to room temperature and stirred for 14 h. The reaction mixture was quenched with saturated aqueous NH$_4$Cl and water was added. The organic layer was separated and the aqueous layer was extracted with EtOAc. The combined organic layers were dried (MgSO$_4$) and concentrated under reduced pressure. The residue was purified by flash chromatography (SiO$_2$, 70% EtOAc/hexanes) to give 664 mg of the desired compound (64% yield, a mixture of diastereoisomers). $^1$H NMR (400 MHz, CD$_3$OD): δ 8.26 (s, 0.7H), 8.24 (s, 1.3H), 7.66 (s, 1H), 7.11 (m, 3H), 4.23 (m, 1H), 4.14 (d, 0.4H, J=11 Hz), 4.10 (d, 0.6H, J=11 Hz), 4.04 (d, 0.6H, J=11 Hz), 3.79 (d, 0.4H, J=11 Hz), 3.19 (d, 0.6H, J=18 Hz), 3.16 (d, 0.4H, J=18 Hz), 3.03 (d, 0.4H, J=18 Hz), 2.71 (d, 0.6H, J=18 Hz), 2.23 (s, 3H), 2.16 (s, 1.2H), 2.11 (s, 1.8H), 1.22 (d, 3H, J=6 Hz). LC-MS R$_t$ (retention time): 2.68 min, MS: (ES) m/z 489 (M+H$^+$).

Example 26

Synthesis of N-(3-chloro-5-(trifluoromethyl)phenyl)-3-ethyl-1-(2,6-dimethylphenyl)-5-oxopyrrolidine-3-carboxamide

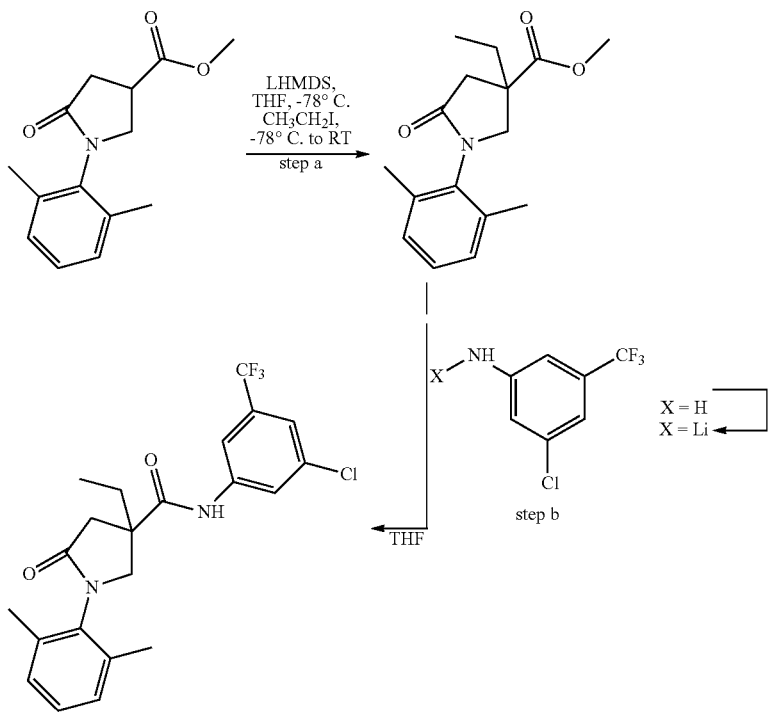

a) A solution of LHMDS (1 M in THF, 39 mL, 39 mmol) was added to a solution of methyl 1-(2,6-dimethylphenyl)-5-oxopyrrolidine-3-carboxylate (9.2 g, 37 mmol) in THF (150 mL) at −78° C. After stirring at the same temperature for 45 min, iodoethane (200 mL, 63 mmol) was added all at once. The cooling bath was removed and the reaction mixture was allowed to warm to room temperature. After 4 h, the reaction mixture was quenched with saturated aqueous NH$_4$Cl. The aqueous layer was extracted with ethyl acetate, and the combined organic layers were dried (Na$_2$SO$_4$), filtered, and concentrated under reduced pressure. The resulting residue was purified by flash chromatography (SiO$_2$, 30-50% EtOAc/hexanes) to obtain the desired product in 59% yield (5.99 g). LC-MS R$_t$ (retention time): 2.23 min, MS: (ES) m/z 276 (M+H$^+$).

b) To a solution of 3-chloro-5-trifluoromethylaniline (94 mg, 0.48 mmol) dissolved in THF (1 mL) was added a solution of n-butyllithium (2.5 M in hexanes, 0.20 mL, 0.50 mmol). After 5 minutes, this solution was added to a solution of the ester prepared in step a (60 mg, 0.22 mmol) in THF (1 mL). The reaction mixture was stirred for 10 h, after which time it was quenched with saturated aqueous NH$_4$Cl, diluted with ethyl acetate, washed with saturated aqueous NaCl, dried over MgSO$_4$, filtered, and concentrated under reduced pressure. The resulting residue was purified by flash chromatography (SiO$_2$, 10-80% EtOAc/hexanes) to obtain the desired product in 59% yield (124 mg). $^1$H NMR (400 MHz, CD$_3$OD): δ 8.01 (s, 1H), 7.91 (s, 1H), 7.41 (s, 1H), 7.1 (m, 3H), 4.13 (d, 1H, J=12 Hz) 3.67 (d, 1H, J=12 Hz) 3.25 (d, 1H, J=18 Hz), 2.23 (s, 3H), 2.12 (s, 3H), 2.10 (m, 2H), 0.98 (t, 3H, J=18 Hz). LC-MS R$_t$ (retention time): 3.03 min, MS: (ES) m/z 439 (M+H$^+$).

Example 27

Synthesis of cis-N-(3-chloro-5-(trifluoromethyl)phenyl)-3-ethyl-4-methyl-1-(2,6-dimethylphenyl)-5-oxopyrrolidine-3-carboxamide a) A solution of LHMDS (1 M in THF, 12 mL, 12 mmol) was added to a solution of methyl 3-ethyl-1-(2,6-dimethylphenyl)-5-oxopyrrolidine-3-carboxylate (3.0 g, 11 mmol) in THF (30 mL) at −78° C. After stirring at the same temperature for 20 min, iodomethane (2.5 mL, 40 mmol) was added. The cooling bath was removed and the reaction mixture was allowed to warm to room temperature. After 1 h, the reaction mixture was quenched with saturated aqueous NH$_4$Cl. The aqueous layer was extracted with ethyl acetate, and the combined organic layers were dried (Na$_2$SO$_4$), filtered, and concentrated under reduced pressure. The resulting residue was purified by flash chromatography (SiO$_2$, 30% EtOAc/hexanes) to obtain the desired product in 76% yield (2.38 g). LC-MS R$_t$ (retention time): 2.37 min, MS: (ES) m/z 230 (M+H$^+$).

b) To a solution of 3-chloro-5-trifluoromethylaniline (94 mg, 0.48 mmol) dissolved in THF (1 mL) was added a solution of n-butyllithium (2.5 M in hexanes, 0.20 mL, 0.50 mmol). After 5 minutes, this solution was added to a solution of the ester prepared in step a (64 mg, 0.22 mmol) in THF (1 mL). The reaction mixture was heated at 60° C. for 2 h, after which time it was quenched with saturated aqueous NH$_4$Cl, diluted with ethyl acetate, washed with saturated aqueous NaCl, dried over MgSO$_4$, filtered, and concentrated under reduced pressure. The residue was purified by reverse phase preparative HPLC (15-95% gradient of CH$_3$CN/H$_2$O with 0.1% TFA modifier) and dried (lyophilizer) to give the major diastereoisomer indicated in 33% yield (60 mg). $^1$H NMR (400 MHz, CD$_3$OD): δ 8.01 (Hs, 1H), 7.91 (s, 1H), 7.41 (s, 1H), 7.1 (m, 3H), 4.13 (d, 1H, J=11 Hz), 3.70 (d, 1H, J=11 Hz), 3.21 (q, J=8 Hz), 2.20 (s, 3H), 2.11 (s, 3H), 2.05 (m, 2H), 1.49 (d, 3H, J=8 Hz), 0.94 (t, 3H, J=7 Hz). LC-MS R$_t$ (retention time): 3.11 min, MS: (ES) m/z 453 (M+H)$^+$.

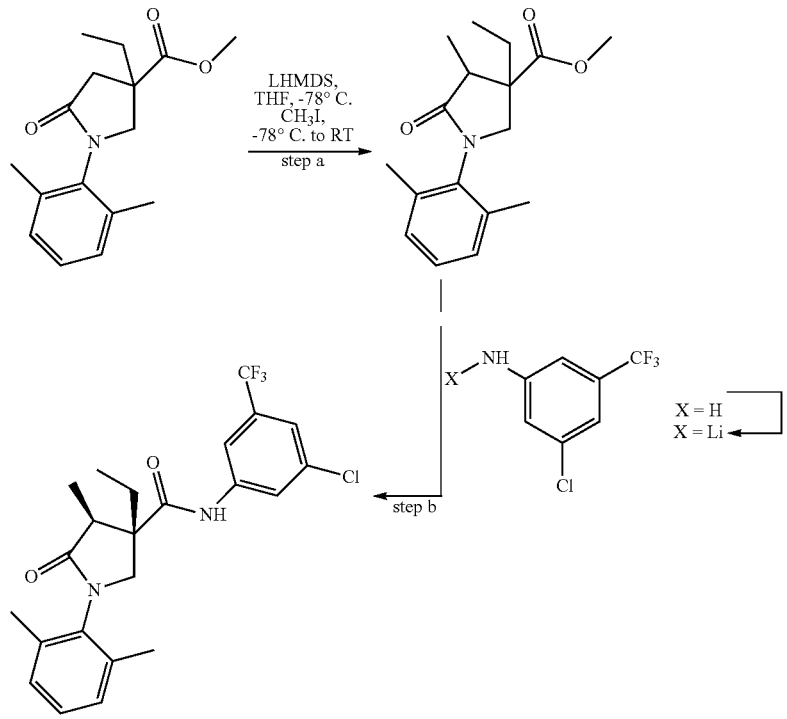

Example 28

Synthesis of cis-3-ethyl-N-(3-(trifluoromethyl)-5-isopropoxyphenyl)-4-methyl-1-(2,6-dimethylphenyl)-5-oxopyrrolidine-3-carboxamide

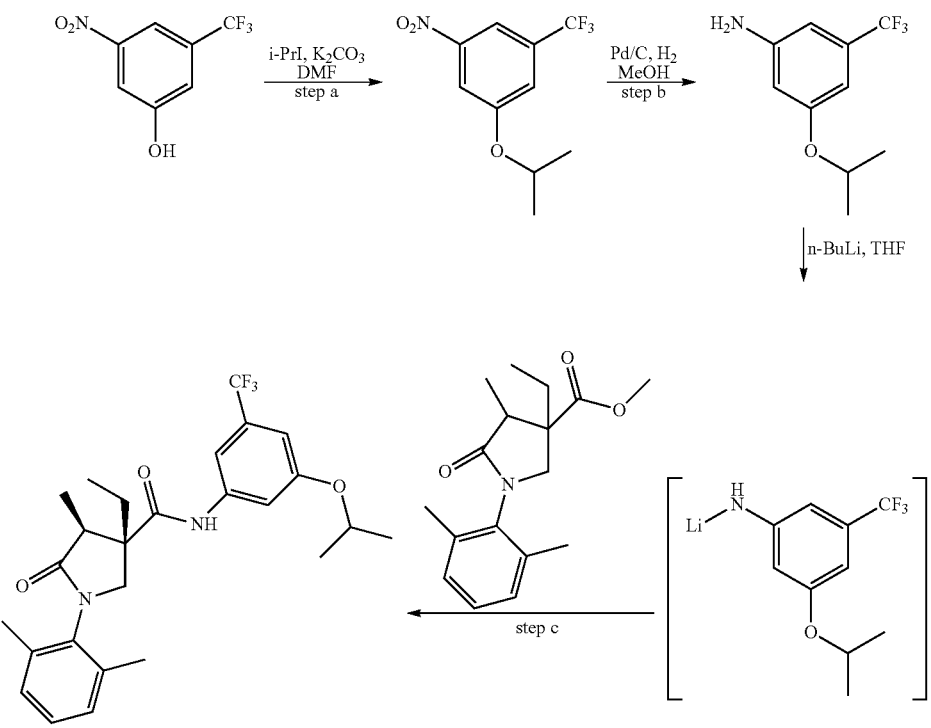

a) To a solution of 3-nitro-5-trifluoromethylphenol (250 mg, 1.2 mmol) dissolved in DMF (3 mL) was added 2-iodopropane (0.50 mL, 5.0 mmol), followed by $K_2CO_3$ (640 mg, 4.6 mmol). The mixture was stirred for 24 hours, after which time the TLC was checked, showing complete consumption of starting material and formation of a single new product. DMF was removed in vacuo, and the reaction mixture was taken up in ether, filtered through Celite and concentrated to obtain a solid residue, which was used in the following step without further purification. TLC $R_f$ (retention factor)=0.67 (20% EtOAc/hexanes).

b) To a solution of 3-(2'-propyloxy)-5-nitrobenzotrifluoride (0.80 g, 3.2 mmol) in methanol (100 mL) was added palladium on carbon (10 wt. %, wet, Degussa type E101 NE/W, 100 mg) and the solution was hydrogenated under a hydrogen balloon (1 atm) for 24 h. The reaction mixture was filtered through Celite, and the cake was rinsed with methanol. The filtrate was concentrated, and the residue was purified by flash chromatography ($SiO_2$, 20% EtOAc/hexanes) to give the pure compound in 88% yield (620 mg). LC-MS $R_t$ (retention time): 2.48 min; MS: (ES) m/z 220 (M+H$^+$).

c) To a solution of 3-(2'-propyloxy)-5-aminobenzotrifluoride (105 mg, 0.48 mmol) dissolved in THF (1 mL) was added a solution of n-butyllithium (2.5 M in hexanes, 0.20 mL, 0.50 mmol). After 5 minutes, this solution was added to a solution of methyl 3-ethyl-4-methyl-1-(2,6-dimethylphenyl)-5-oxopyrrolidine-3-carboxylate (preparation previously described) (56 mg, 0.19 mmol) in THF (1 mL). The reaction mixture was heated at 60° C. for 2 h, after which time it was quenched with saturated aqueous $NH_4Cl$, diluted with ethyl acetate, washed with saturated aqueous NaCl, dried over $MgSO_4$, filtered, and concentrated under reduced pressure. The residue was purified by flash chromatography ($SiO_2$, 0-20% EtOAc/hexanes), followed by recrystallization (EtOAc/toluene/hexanes) to get the desired compound in 50% yield (45 mg). $^1$H NMR (400 MHz, $CD_3OD$): δ 7.51 (□s, 1H), 7.47 (s, 1H), 7.41 (m, 3H), 6.88 (s, 1H), 4.63 (m, 1H), 4.12 (d, 1H, J=10 Hz), 3.71 (d, 1H, J=10 Hz), 3.24 (m, 1H), 2.23 (s, 3H), 2.12 (s, 3H), 2.02 (m, 2H), 1.40 (d, 3H, J=9 Hz), 1.35 (d, 6H, J=6 Hz), 0.95 (t, 3H, J=8 Hz). LC-MS $R_t$ (retention time): 2.91 min, MS: (ES) m/z 477 (M+H)$^+$.

Example 29

Synthesis of cis-3-ethyl-N-(3-(trifluoromethyl)-5-(pyrrolidin-1-yl)phenyl)-4-methyl-1-(2,6-dimethylphenyl)-5-oxopyrrolidine-3-carboxamide

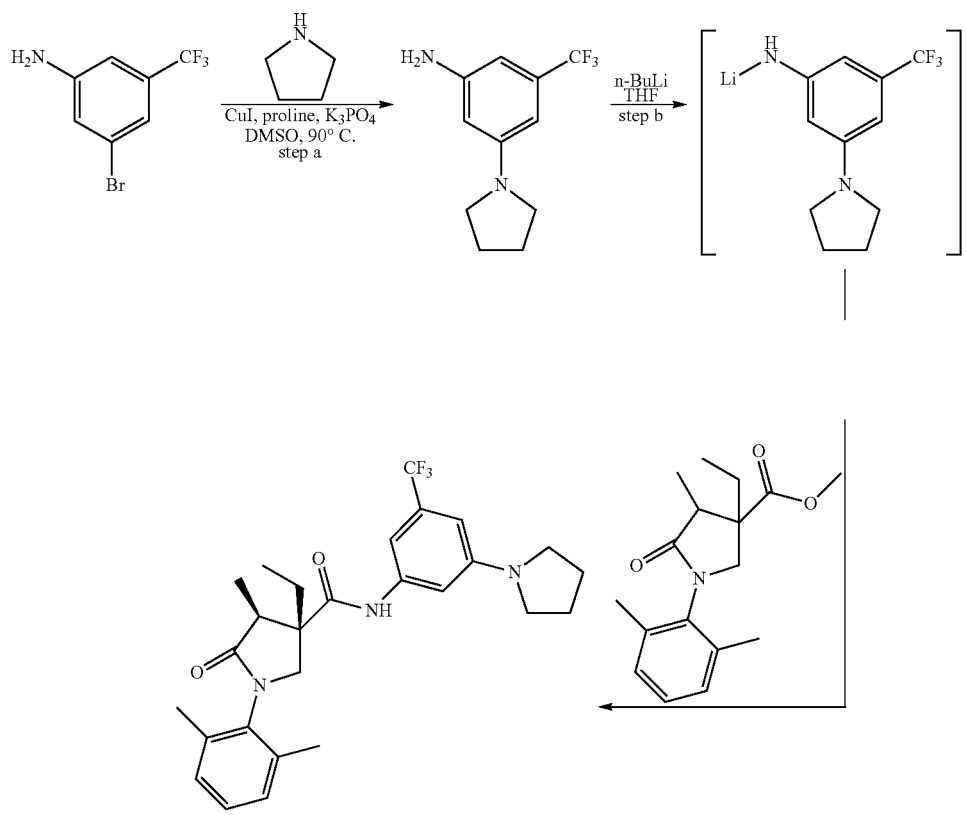

a) 3-Amino-5-bromobenzotrifluoride (1.0 g, 4.2 mmol) was dissolved in DMSO (2 mL). Pyrrolidine (1.0 mL, 13 mmol) was added at room temperature, followed by $K_3PO_4$ (1.9 g, 8.4 mmol), CuI (80 mg, 0.42 mmol), and proline (97 mg, 0.84 mmol). After stirring 16 h at 90° C., LC-MS and TLC indicated the completion of the reaction. The reaction mixture was diluted with EtOAc (50 mL) and washed with aqueous $NH_4OH$ (30%, 60 mL) and brine (20 mL) and the resulting solution was concentrated under reduced pressure. The residue was purified by flash chromatography ($SiO_2$, 10-35% EtOAc/hexanes) to give 800 mg of tan powder (83% yield). LC-MS $R_t$ (retention time): 2.44 min, MS: (ES) m/z 231 (M+H$^+$).

b) To a solution of 3-(pyrrolidin-1-yl)-5-aminobenzotrifluoride (94 mg, 0.41 mmol) dissolved in THF (1 mL) was added a solution of n-butyllithium (2.5 M in hexanes, 0.16 mL, 0.41 mmol). After 5 minutes, this solution was added to a solution of methyl 3-ethyl-4-methyl-1-(2,6-dimethylphenyl)-5-oxopyrrolidine-3-carboxylate (preparation previously described) (53 mg, 0.18 mmol) in THF (1 mL). The reaction mixture was heated at 60° C. for 2 h, after which time it was quenched with saturated aqueous $NH_4Cl$, diluted with ethyl acetate, washed with saturated aqueous NaCl, dried over $MgSO_4$, filtered, and concentrated under reduced pressure. The residue was initially purified by flash chromatography ($SiO_2$, 40% EtOAc/hexanes), followed by reverse phase preparative HPLC (15-95% gradient of $CH_3CN/H_2O$ with 0.1% TFA modifier) and dried (lyophilizer) to give the major diastereoisomer indicated in 50% yield (44 mg). $^1$H NMR (400 MHz, $CD_3OD$): δ 7.10 (m, 5H), 6.52 (s, 1H), 4.10 (d, 1H, J=10 Hz), 3.71 (d, 1H), J=10 Hz), 3.25 (q, 1H, J=8 Hz), 2.20 (s, 3H), 2.13 (s, 3H), 2.00 (m, 2H), 1.38 (d, 3H, J=8 Hz), 0.96 (t, 3H, J=7 Hz). LC-MS $R_t$ (retention time): 3.19 min, MS: (ES) m/z 488 (M+H$^+$).

Example 30

Synthesis of cis-N-(3-cyclopropyl-5-(trifluoromethyl)phenyl)-3-ethyl-4-methyl-1-(2,6-dimethylphenyl)-5-oxopyrrolidine-3-carboxamide

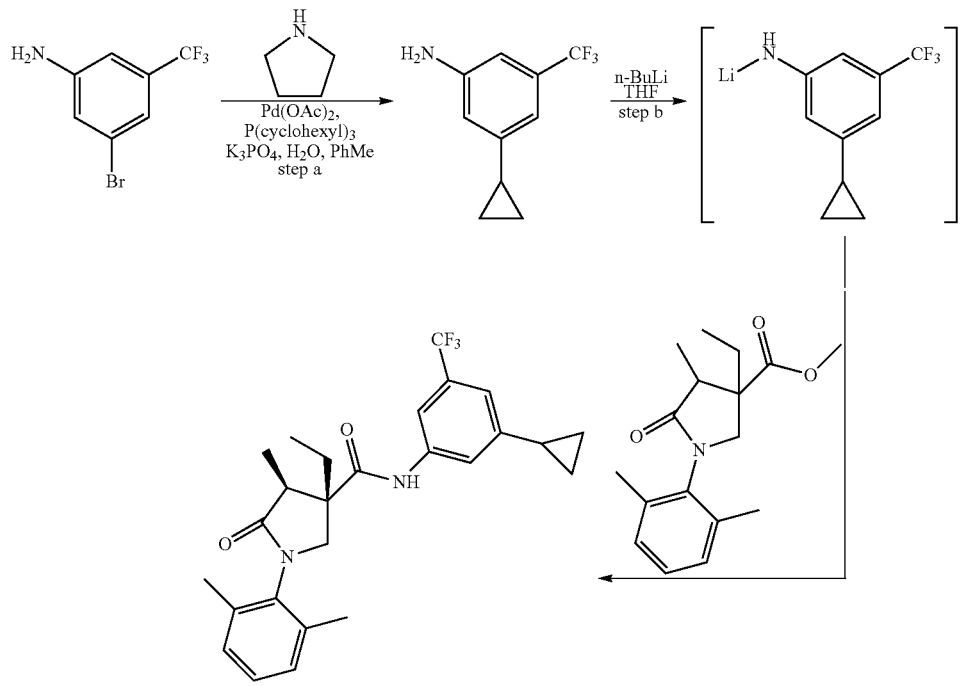

a) A 40 mL vial was charged with 3-amino-5-bromobenzotrifluoride (275 mg, 1.15 mmol), cyclopropylboronic acid (128 mg, 1.5 mmol), Pd(OAc)$_2$ (13 mg, 0.06 mmol), triclyclohexylphosphine (38 mg, 0.13 mmol), and K$_3$PO$_4$ (488 mg, 2.3 mmol). The vial was subsequently sealed with a septum-lined screw cap and purged with nitrogen, followed by the addition of degassed toluene (4 mL) and degassed water (1 mL). After stirring the reaction mixture for 2 h at 100° C., the mixture was diluted in ethyl acetate (50 mL) and the organics were washed with brine, dried (MgSO$_4$), and concentrated in vacuo. The residue was purified by flash chromatography (SiO$_2$, 10-40% EtOAc/hexanes) to give the desired product in 55% yield (126 mg). LC-MS R$_t$ (retention time): 2.46 min, MS: (ES) m/z 202 (M+H$^+$).

b) To a solution of 3-(cyclopropyl)-5-aminobenzotrifluoride (126 mg, 0.626 mmol) in THF (1 mL) was added a solution of n-butyllithium (2.5 M in hexanes, 0.25 mL, 0.63 mmol). After 5 minutes, this solution was added to a solution of methyl 3-ethyl-4-methyl-1-(2,6-dimethylphenyl)-5-oxopyrrolidine-3-carboxylate (preparation previously described) (74 mg, 0.27 mmol) in THF (1 mL). The reaction mixture was heated at 60° C. for 1 h, after which time it was quenched with saturated aqueous NH$_4$Cl, diluted with ethyl acetate, washed with saturated aqueous NaCl, dried over MgSO$_4$, filtered, and concentrated under reduced pressure. The residue was initially purified by flash chromatography (SiO$_2$, 40% EtOAc/hexanes), followed by reverse phase preparative HPLC (15-95% gradient of CH$_3$CN/H$_2$O with 0.1% TFA modifier) and dried (lyophilizer) to give the major diastereoisomer indicated in 20% yield (25 mg). $^1$H NMR (400 MHz, CD$_3$OD): δ 7.74 (s, 1H), 7.51 (s, 1H), 7.10 (m, 4H), 4.10 (d, 1H, J=10 Hz), 3.70 (d, 1H, J=10 Hz), 3.23 (q, 1H, J=8 Hz), 2.20 (s, 3H), 2.11 (s, 3H), 2.03 (m, 2H), 1.39 (d, 3H, J=8 Hz), 1.05 (m, 2H), 0.93 (t, 3H, J=7 Hz), 0.74 (m, 2H). LC-MS R$_t$ (retention time): 3.02 min, MS: (ES) m/z 459 (M+H$^+$).

Example 31

Synthesis of tert-butyl 1-(2,6-dimethylphenyl)-5-oxopyrrolidine-3-carboxylate

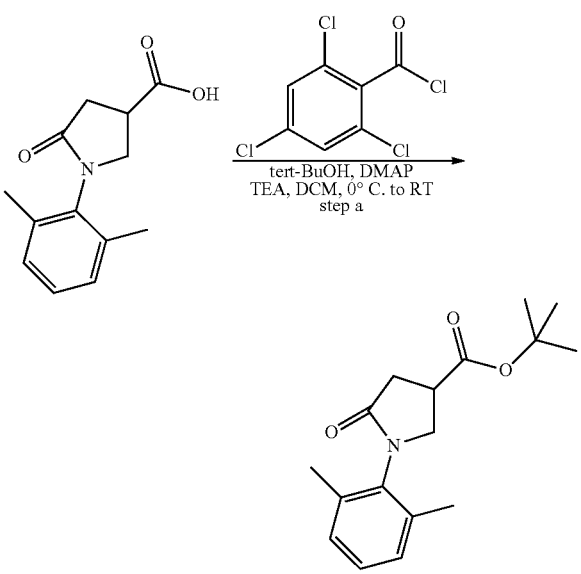

a) To a 2 L, 3-neck flask was added 1-(2,6-dimethylphenyl)-5-oxopyrrolidine-3-carboxylic acid (93 g, 0.40 mol), anhydrous tert-butanol (60 mL, 0.63 mol), TEA (110 mL, 0.79 mol), DMAP (5.0 g, 41 mmol), and CH$_2$Cl$_2$ (800 mL). After the mixture was cooled in an ice bath under nitrogen atmosphere with mechanical stirring, 2,4,6-trichlorobenzoyl chloride (108 g, 0.443 mol) was added in portions over the course of 15 minutes such that the temperature did not exceed 10° C. After the addition was complete, the ice bath was removed, the mixture was allowed to warm to room temperature and stirred for an additional 14 h. TLC and LCMS indicated complete consumption of starting material and formation of desired product. The mixture was filtered and the filter cake was washed with EtOAc (100 mL) and ether (150 mL). The filtrate was washed with two 200 mL portions of 1 M NaHSO$_4$, four 200 mL portions of saturated aqueous NaHCO$_3$, and brine (100 mL). After drying over MgSO$_4$, the organic phase was treated with 24 g of silica gel, and filtered. The filtrate was concentrated to 250 mL and diluted with hexane. A crystalline precipitate began to form, and an initial crop of 66 g was recovered. The filtrate was recovered and recrystallized (ether/hexanes) to afford a second crop (27 g); overall yield, 93 g (81%). LC-MS R$_t$ (retention time): 2.28 min, MS: (ES) m/z 290 (M+H$^+$).

Example 32

Synthesis of (S)—N-(3,5-bis(trifluoromethyl)phenyl)-1-(2,6-dimethylphenyl)-3-ethyl-5-oxopyrrolidine-3-carboxamide

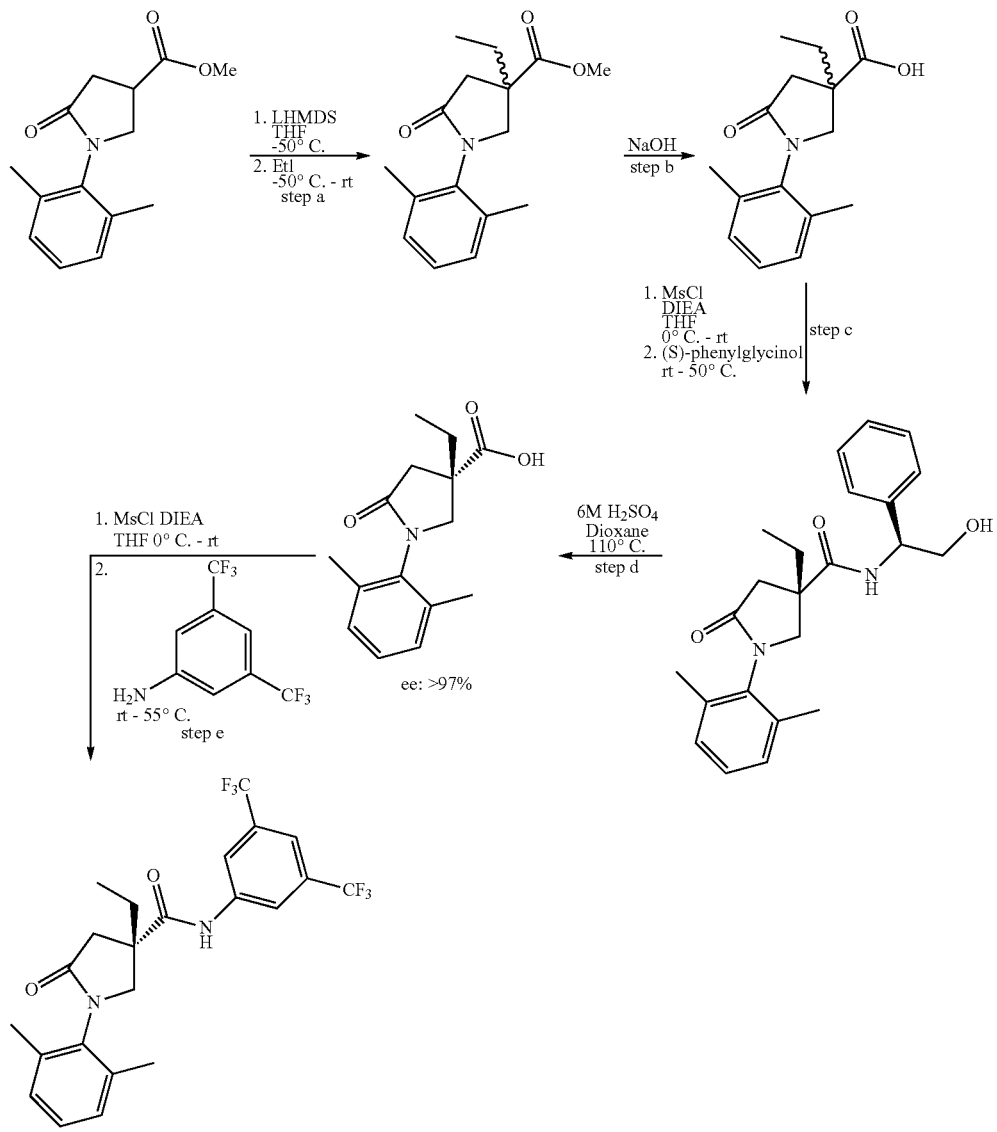

a) To a solution of methyl 1-(2,6-dimethylphenyl)-5-oxopyrrolidine-3-carboxylate (21.8 g, 88.2 mmol) in 250 mL anhydrous THF at −50° C. was added LHMDS (91 mL, 1.0 M) dropwise via addition funnel. The homogeneous solution was stirred 30 min, followed by the addition of ethyl iodide (10 mL, 125 mmol). The cold bath was subsequently removed and the reaction was stirred at ambient temperature for 2.5 h. The resultant solution was quenched with 100 mL saturated ammonium chloride, partitioned with ethyl acetate, and extracted with EtOAc. The combined organics were subsequently washed with saturated NaHSO$_3$, washed with brine, and dried with sodium sulfate. The crude product was purified via silica gel chromatography (MTBE/hexanes) to afford the alkylated product (14.5 g) in 60% yield. LC-MS $R_t$ (retention time): 2.17 min; MS: (ES) m/z 276 (M+H$^+$).

b) A 500 mL flask was charged with the ester from step a (1.4 g, 4.9 mmol), NaOH (40 mL, 1.0 M), and EtOH (20 mL). The resultant mixture was stirred 105 min and then 6 M HCl was added slowly to precipitate the desired acid. The precipitate was washed thoroughly with 10% HCl and dried at reduced pressure to generate the desired acid in quantitative yield (1.3 g). LC-MS $R_t$ (retention time): 1.42 min; MS: (ES) m/z 262 (M+H$^+$).

c) To a solution of 1-(2,6-dimethylphenyl)-3-ethyl-5-oxopyrrolidine-3-carboxylic acid (500 mg, 1.91 mmol), methanesulfonyl chloride (0.233 mL, 2.86 mmol), and THF (4 mL) at 0° C. was added diisopropylethylamine (1.0 mL, 5.73 mmol). The solution was stirred 15 min at 0° C., warmed to ambient temperature, and then stirred an additional 20 min. (S)-phenylglycinol (523 mg, 3.82 mmol) was subsequently added and the solution was heated at 55° C. overnight. The following day, the reaction mixture was quenched with 10% HCl and the aqueous layer was extracted three times with EtOAc. The combined organics were washed with sodium bicarbonate, dried with sodium sulfate, concentrated in vacuo, and purified via preparative HPLC to afford the two diastereomeric amides (faster eluting diastereomer: 128 mg, 18% yield; slower eluting diastereomer: 132 mg, 18% yield), the former of which was the desired diastereomer. 1$^{st}$ diastereomer: LC-MS $R_t$ (retention time): 1.81 min; MS: (ES) m/z 381 (M+H$^+$). 2$^{nd}$ diastereomer: LC-MS $R_t$ (retention time): 1.94 min; MS: (ES) m/z 381 (M+H$^+$).

d) A 25 mL scintillation vial was charged with the amide from step c (140 mg, 0.367 mmol), concentrated sulfuric acid (1.4 mL), and dioxane (1.4 mL). The solution was sealed and heated at 110° C. overnight. The next day, the reaction was partitioned with diethyl ether and brine, the aqueous layer was extracted three times with diethyl ether, and the combined organics were dried over sodium sulfate to provide the desired acid (83 mg) in 86% yield. The enantiopurity was determined to be >97% via chiral HPLC (Regis Whelk, 88% hexanes: 12% EtOH with 0.1% AcOH, 1 mL/min flow rate, $R_t$ (retention time): 19.8 min). LC-MS $R_t$ (retention time): 1.39 min; MS: (ES) m/z 262 (M+H$^+$).

e) To a solution of crude acid from step d (10 mg, 0.038 mmol) and methanesulfonyl chloride (6 µL, 0.076 mmol) in THF (0.38 mL) at 0° C. was added diisopropylethylamine (0.027 mL, 0.15 mmol). The solution was stirred 15 min at 0° C., warmed to ambient temperature, and 3,5-bis(trifluoromethyl)benzenamine (0.018 mL, 0.12 mmol) was subsequently added and the solution was heated at 55° C. overnight. The following day, the reaction mixture was purified via preparative HPLC to afford the desired amide as a white solid. $^1$H NMR (400 MHZ, CDCl): δ 8.06 (s, 2H), 7.67 (s, 1H), 7.64 (s, 1H), 7.04-7.17 (m, 3H), 4.16 (d, J=10.4 Hz, 1H), 3.50 (d, J=10.4 Hz, 1H), 3.14 (d, J=16.8 Hz, 1H), 2.67 (d, J=16.8 Hz, 1H), 2.24 (s, 3H), 2.17 (s, 3H), 1.95-2.14 (m, 2H), 1.06 (t, J=7.2 Hz, 3H). LC-MS $R_t$ (retention time): 3.00 min; MS: (ES) m/z 473 (M+H$^+$).

Example 33

Synthesis of (3S,4S)—N-(3,5-bis(trifluoromethyl)phenyl)-1-(2,6-dimethylphenyl)-3-ethyl-4-methyl-5-oxopyrrolidine-3-carboxamide

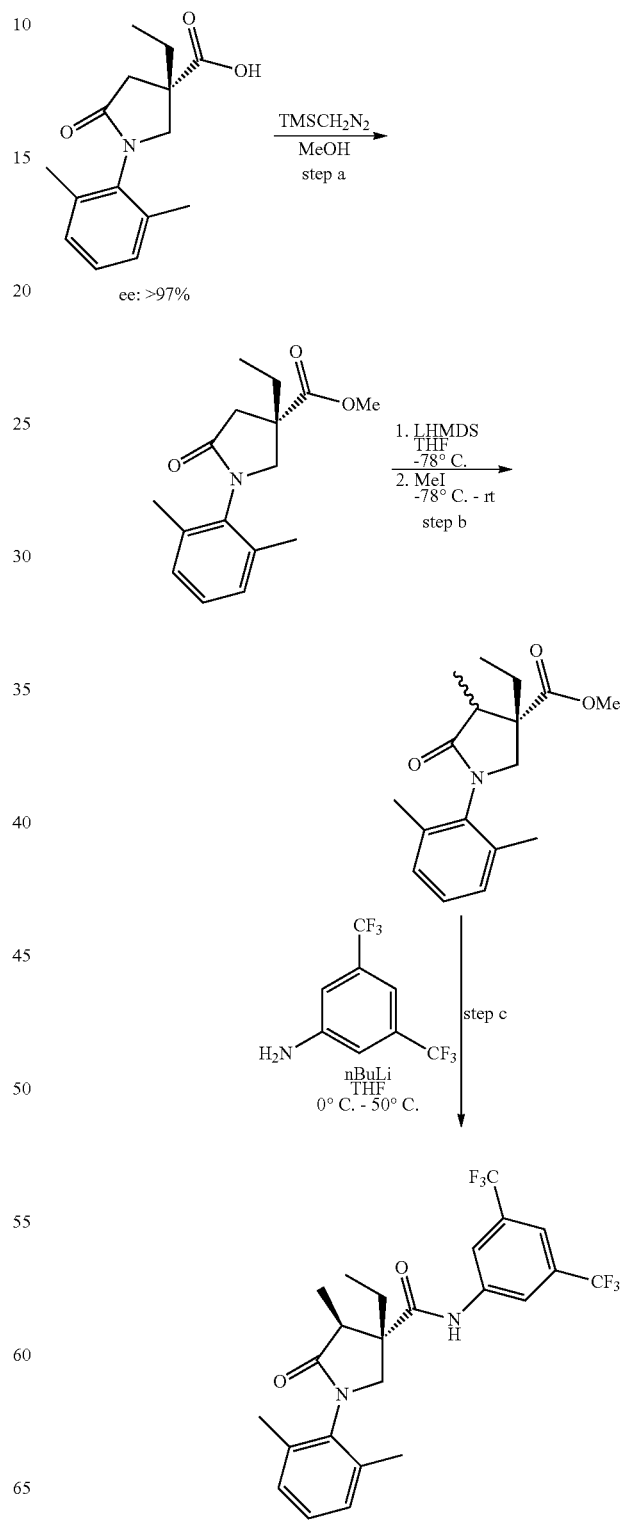

a) To a solution of (S)-1-(2,6-dimethylphenyl)-3-ethyl-5-oxopyrrolidine-3-carboxylic acid (79 mg, 0.30 mmol) in MeOH (4.0 mL) was added trimethylsilyldiazomethane (2.0 M) until the yellow color of the reagent persisted. The homogeneous solution was stirred an additional 30 min, followed by the addition of acetic acid to quench the excess reagent. The crude mixture was subsequently partitioned with EtOAc/saturated sodium bicarbonate and the aqueous layer was extracted two times with EtOAc. The combined organics were dried over sodium sulfate and concentrated in vacuo to afford the desired methyl ester (82 mg, quantitative yield) which was utilized directly in the next step. LC-MS $R_t$ (retention time): 2.15 min; MS: (ES) m/z 276 (M+H$^+$).

b) To a solution of crude (S)-methyl 1-(2,6-dimethylphenyl)-3-ethyl-5-oxopyrrolidine-3-carboxylate (82 mg, 0.30 mmol) in 3 mL anhydrous THF at −78° C. was added LHMDS (0.31 mL, 1.0 M). The homogeneous solution was stirred 30 min, followed by the addition of methyl iodide (0.037 mL, 0.59 mmol). The reaction was allowed to slowly warm to room temperature (as the acetone/dry ice warmed) and stirred overnight. The following day, the solution was quenched with 10% HCl, partitioned with ethyl acetate, and the organic layer was separated. The organics were subsequently washed with 10% HCl, washed with brine, dried with sodium sulfate, and concentrated in vacuo to generate 83 mg (quantitative yield) of the methylated pyrrolidinone as a mixture of diastereomers which were utilized directly in the next step. LC-MS $R_t$ (retention time): 2.33 min; MS: (ES) m/z 290 (M+H$^+$).

c) To a solution of 3,5-bis(trifluoromethyl)benzenamine (500 mg, 2.18 mmol) in THF (3.6 mL) at 0° C. was added nBuLi (0.83 mL, 2.5 M). The solution was stirred 20 min to enable anion formation. In a separate flask, the crude ester from step b (83 mg, 0.30 mmol) was dissolved in THF (0.8 mL) and the solution was cooled to 0° C. The lithium anion of 3,5-bis(trifluoromethyl)benzenamine (1.62 mL, 0.46 M) was subsequently added to the crude ester and the flask was warmed to ambient temperature and stirred overnight. The following day, the crude reaction was purified by preparative HPLC, which failed to provide the desired product in sufficient purity. The purest fractions were subsequently purified via silica gel chromatography (EtOAc/hexanes) to afford the desired product as a white solid. $^1$H NMR (400 MHZ, CDCl): δ 8.04 (s, 2H), 7.64 (s, 1H), 7.56 (s, 1H), 7.04-7.16 (m, 3H), 4.20 (d, J=10.3 Hz, 1H), 3.46 (d, J=10.3 Hz, 1H), 3.06 (q, J=7.0 Hz, 1H), 2.22 (s, 3H), 2.17 (s, 3H), 1.94 (q, J=7.2 Hz, 2H), 1.46 (d, J=7.2 Hz, 3H), 1.05 (t, J=7.2 Hz, 3H). LC-MS $R_t$ (retention time): 3.01 min; MS: (ES) m/z 487 (M+H$^+$).

Example 34

Synthesis of (R)—N-(3-cyclopropyl-5-(trifluoromethyl)phenyl)-1-(2,6-dimethylphenyl)-3-isopropyl-5-oxopyrrolidine-3-carboxamide

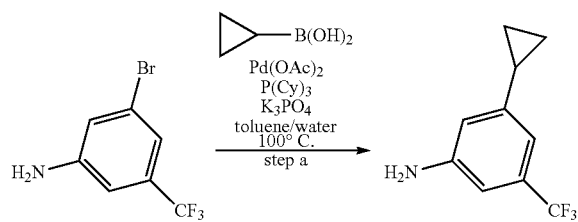

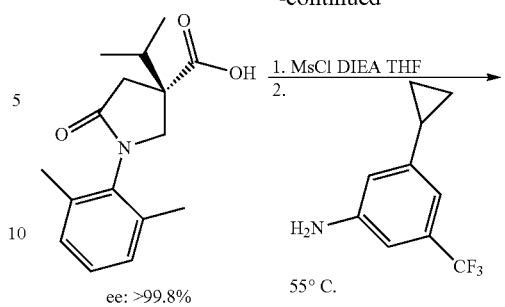

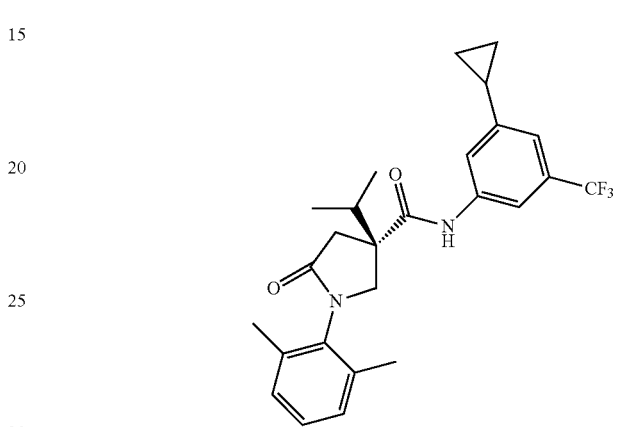

a) A 40 mL vial was charged with 3-amino-5-bromobenzotrifluoride (275 mg, 1.15 mmol), cyclopropylboronic acid (128 mg, 1.5 mmol), Pd(OAc)$_2$ (13 mg, 0.06 mmol), tricyclohexylphosphine (38 mg, 0.13 mmol), and K$_3$PO$_4$ (488 mg, 2.3 mmol). The vial was subsequently sealed with a septum-lined screw cap and purged with nitrogen, followed by the addition of degassed toluene (4 mL) and degassed water (1 mL). After stirring the reaction mixture for 2 h at 100° C., the mixture was diluted in ethyl acetate (50 mL) and the organics were washed with brine, dried (MgSO$_4$), and concentrated in vacuo. The residue was purified via flash chromatography (SiO$_2$, 10-40% EtOAc/hexanes) to give the desired product in 55% yield (126 mg). LC-MS $R_t$ (retention time): 2.46 min, MS: (ES) m/z 202 (M+H$^+$).

b) To a solution of (R)-1-(2,6-dimethylphenyl)-3-isopropyl-5-oxopyrrolidine-3-carboxylic acid (32 mg, 0.12 mmol) and methanesulfonyl chloride (12 μL, 0.15 mmol) in THF (0.6 mL) at 0° C. was added diisopropylethylamine (0.060 mL, 0.35 mmol). The solution was stirred 15 min at 0° C., warmed to ambient temperature, and 3-cyclopropyl-5-(trifluoromethyl)benzenamine (47 mg, 0.23 mmol) was subsequently added and the solution was heated at 55° C. overnight. The following day, the reaction mixture was purified via preparative HPLC to afford the desired amide as a white solid. $^1$H NMR (400 MHZ, CDCl): δ 9.89 (s, 1H), 7.86 (s, 1H), 7.56 (s, 1H), 7.05-7.17 (m, 4H), 3.97 (d, J=10.4 Hz, 1H), 3.67 (d, J=10.4 Hz, 1H), 3.04 (d, J=17.2 Hz, 1H), 2.65 (d, J=17.2 Hz, 1H), 2.36 (septet, J=6.8 Hz, 1H), 2.16 (s, 3H), 1.99-2.08 (m, 1H), 1.99 (s, 3H), 1.00-1.06 (m, 2H), 0.96 (t, J=6.8 Hz, 6H), 0.70-0.75 (m, 2H). LC-MS $R_t$ (retention time): 3.02 min; MS: (ES) m/z 459 (M+H$^+$).

Example 35

Synthesis of (R)—N-(3-cyano-5-(trifluoromethyl)phenyl)-1-(2,6-dimethylphenyl)-3-isopropyl-5-oxopyrrolidine-3-carboxamide

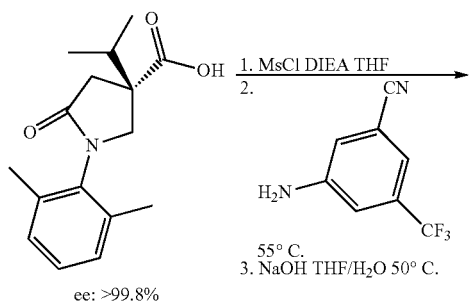

To a solution of (R)-1-(2,6-dimethylphenyl)-3-isopropyl-5-oxopyrrolidine-3-carboxylic acid (25 mg, 0.091 mmol) and methanesulfonyl chloride (9 μL, 0.12 mmol) in THF (0.9 mL) at 0° C. was added diisopropylethylamine (0.047 mL, 0.27 mmol). The solution was stirred 15 min at 0° C., warmed to ambient temperature, and 3-amino-5-(trifluoromethyl)benzonitrile (34 mg, 0.18 mmol) was subsequently added and the solution was heated at 55° C. overnight. The following day, the reaction mixture was purified via preparative HPLC, which failed to provide the desired product in sufficient purity. To a solution of the crude mixture (14 mg) in 2 mL THF was added aqueous NaOH (3 mL, 1.0 M) and the solution was stirred at 50° C. overnight. The following day, the solution was quenched with 10% HCl, partitioned with ethyl acetate, and the organic layer was separated. The organics were subsequently dried with sodium sulfate, concentrated in vacuo, and purified via preparative HPLC to afford the desired amide as a white solid. $^1$H NMR (400 MHZ, CDCl): δ 10.28 (s, 1H), 8.39 (s, 1H), 8.30 (s, 1H), 8.05 (s, 1H), 7.04-7.17 (m, 3H), 3.99 (d, J=11.2 Hz, 1H), 3.67 (d, J=10.8 Hz, 1H), 3.05 (d, J=17.2 Hz, 1H), 2.70 (d, J=17.2 Hz, 1H), 2.38 (septet, J=6.8 Hz, 1H), 2.17 (s, 3H), 2.00 (s, 3H), 0.98 (t, J=6.8 Hz, 6H). LC-MS $R_t$ (retention time): 2.81 min; MS: (ES) m/z 444 (M+H$^+$).

Example 36

Synthesis of (R)-1-(2,6-dimethylphenyl)-N-(3-isopropoxy-5-(trifluoromethyl)phenyl)-3-isopropyl-5-oxopyrrolidine-3-carboxamide

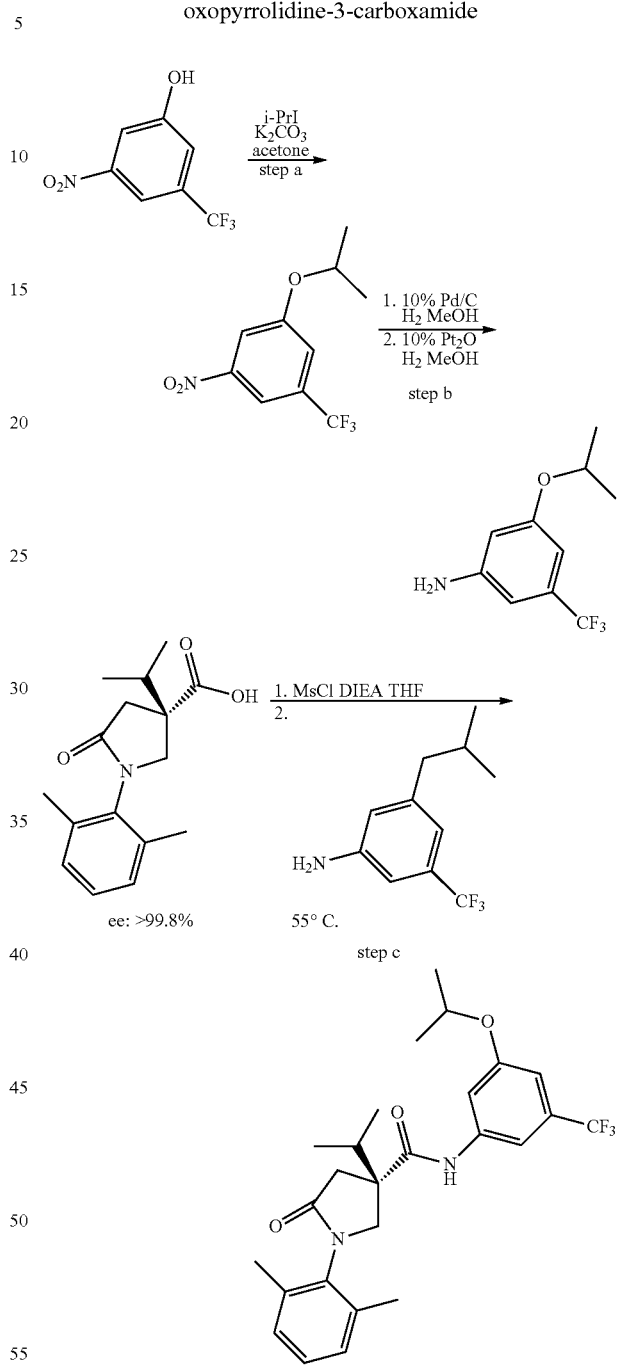

a) To a solution of 3-nitro-5-(trifluoromethyl)phenol (6.0 g, 29.0 mmol) in acetone (60 mL) was added potassium carbonate (12.0 g, 87.0 mmol) and isopropyl iodide (4.35 mL, 43.5 mmol). The heterogeneous mixture was then stirred overnight at ambient temperature. The following day, the reaction mixture was partitioned with diethyl ether/water and the aqueous layer was extracted two times with diethyl ether. The combined organics were dried with sodium sulfate, concentrated in vacuo, and the crude product was purified by flash chromatography (SiO$_2$, 25% EtOAc/hexanes) to afford the desired ether as a yellow oil. LC-MS $R_t$ (retention time): 2.98 min.

b) A Parr-shaker flask was charged with the ether from step a (~29.0 mmol), 10% Pd/C (1.0 g, 0.94 mmol), and MeOH (50 mL). The heterogeneous solution was hydrogenated using a Parr shaker at 40 psi overnight. The reaction mixture was filtered through Celite, and the cake was rinsed with MeOH. The filtrate was concentrated and the residue was purified by flash chromatography (SiO$_2$, 25% EtOAc/hexanes) to afford a mixture of the desired aniline and partially reduced nitroso compound. To a solution of the nitroso intermediate (~6 g) in methanol (15 mL) was added 10% platinum oxide (1.0 g, 0.44 mmol) and the solution was hydrogenated using a Parr shaker at 40 psi overnight. The reaction mixture was filtered through Celite, and the cake was rinsed with methanol. The filtrate was concentrated and the residue was purified by flash chromatography (SiO$_2$, 25% EtOAc/hexanes) to afford the desired aniline (4.5 g, 71% two-step yield). LC-MS R$_t$ (retention time): 2.47 min; MS: (ES) m/z 220 (M+H$^+$).

c) To a solution of (R)-1-(2,6-dimethylphenyl)-3-isopropyl-5-oxopyrrolidine-3-carboxylic acid (25 mg, 0.091 mmol) and methanesulfonyl chloride (9 μL, 0.12 mmol) in THF (0.9 mL) at 0° C. was added diisopropylethylamine (0.047 mL, 0.27 mmol). The solution was stirred 15 min at 0° C., warmed to ambient temperature, and 3-isopropoxy-5-(trifluoromethyl)benzenamine (39 mg, 0.18 mmol) was subsequently added and the solution was heated at 55° C. overnight. The following day, the reaction mixture was purified via preparative HPLC to afford the desired amide as a white solid. $^1$H NMR (400 MHZ, CDCl): δ 9.91 (s, 1H), 7.59 (s, 1H), 7.56 (s, 1H), 7.04-7.16 (m, 3H), 6.90-6.94 (m, 1H), 4.65 (septet, J=6.0 Hz, 1H), 3.97 (d, J=10.4 Hz, 1H), 3.66 (d, J=10.8 Hz, 1H), 3.04 (d, J=17.2 Hz, 1H), 2.66 (d, J=17.2 Hz, 1H), 2.36 (septet, J=6.8 Hz, 1H), 2.16 (s, 3H), 2.00 (s, 3H), 1.29 (d, J=6.0 Hz, 6H), 0.96 (t, J=6.4 Hz, 6H). LC-MS R$_t$ (retention time): 3.08 min; MS: (ES) m/z 477 (M+H$^+$).

Example 37

Synthesis of (1S*,5S*)-3-(2,6-dimethylphenyl)-4-oxo-3-azabicyclo[3.2.0]heptane-1-carboxylic acid [3,5-bis(trifluoromethyl)phenyl]amide

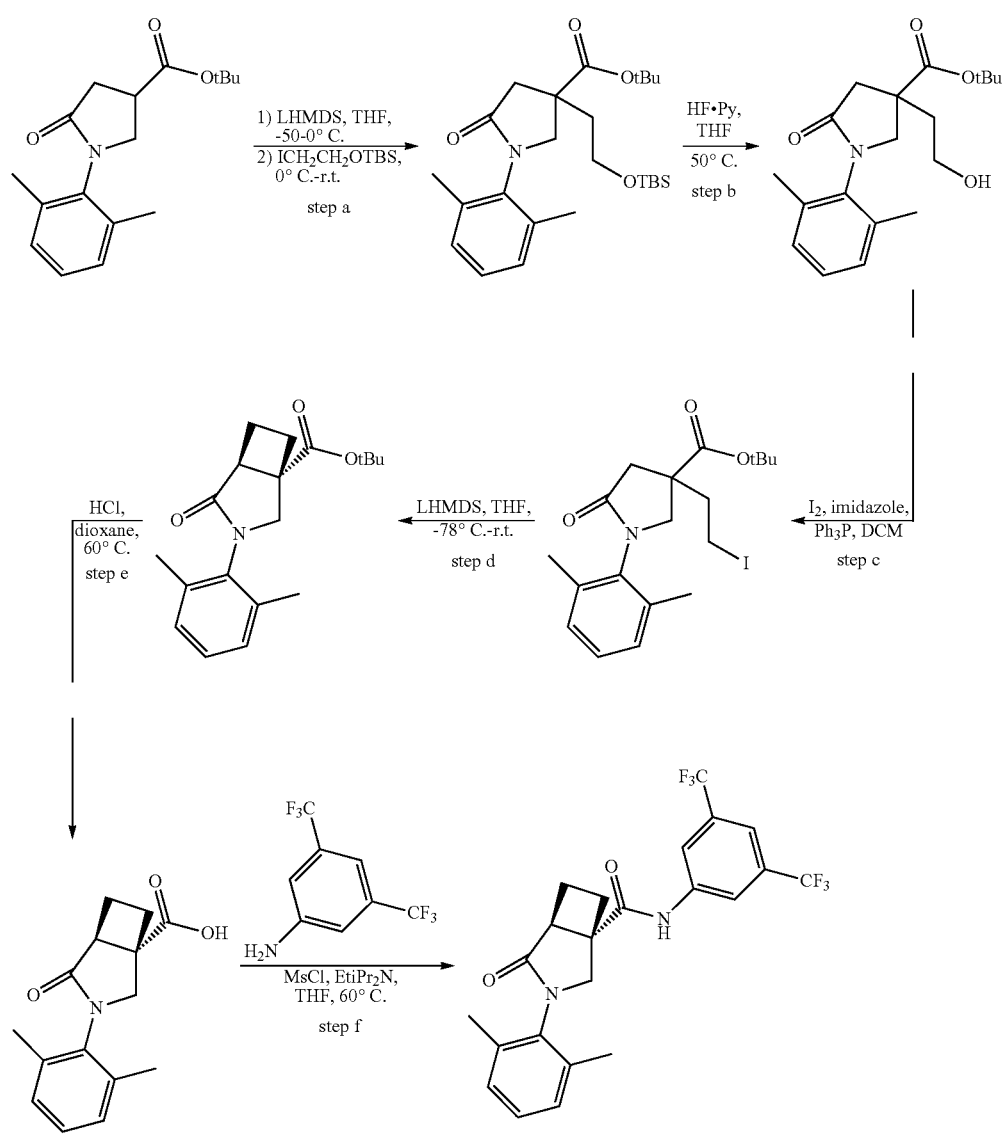

a) LHMDS (1.0 M in THF, 13.4 mL, 13.4 mmol) was added to the solution of 1-(2,6-dimethylphenyl)-5-oxo-pyrrolidine-3-carboxylic acid tert-butyl ester (3.53 g, 12.2 mmol) in THF (6 mL) in a reaction flask cooled to −50° C. under nitrogen atmosphere. The reaction mixture was allowed to warm up to 0° C. (precipitate forms), whereupon tert-butyl-(2-iodoethoxy)-dimethylsilane (3.84 g, 13.4 mmol) was added and the mixture was thoroughly shaken. The reaction mixture was allowed to warm up to room temperature and was kept stirring for 1 h. 20 mL of half-saturated aqueous ammonium chloride solution was added, followed by 100 mL of DCM. The organic layer was concentrated in vacuo on silica gel and purified by flash chromatography ($SiO_2$, 5-35% EtOAc/hexanes) to give 3.28 g of the desired compound (60% yield). LC-MS $R_t$ (retention time): 3.41 min, MS: (ES) m/z 448 (M+H$^+$).

b) Hydrogen fluoride-pyridine complex (70 wt % HF, 118 µL, 4.83 mmol) was added to a solution of the silyl ether from step a (298 mg, 0.67 mmol) in THF (3 mL) at room temperature. The mixture was heated in a polypropylene vial to 50° C. for 1 h. The solution was concentrated in vacuo on silica gel and purified by flash chromatography ($SiO_2$, 20-100% EtOAc/hexanes) to give 200 mg of the desired compound (90% yield) as a white solid. LC-MS: $R_t$ (retention time): 1.94 min, MS: (ES) m/z 334 (M+H$^+$).

c) Iodine (230 mg, 0.905 mmol) was added portionwise to a solution of imidazole (62 mg, 0.905 mmol) and triphenylphosphine (237 mg, 0.905 mmol) in DCM (1 mL). Upon the dissolution of iodine, the alcohol (prepared in step b, 200 mg, 0.601 mmol) was added. The reaction mixture was aged for 16 h at room temperature, concentrated in vacuo on silica gel and purified by flash chromatography ($SiO_2$, 0-50% EtOAc/hexanes) to give 223 mg of the desired compound (84% yield). LC-MS $R_t$ (retention time): 2.80 min, MS: (ES) m/z 444 (M+H$^+$).

d) LHMDS (1.0 M in THF, 0.55 mL, 0.55 mmol) was added to the solution of the iodide prepared in step c (223 mg, 0.50 mmol) in THF (6 mL) in a reaction flask cooled to −78° C. under nitrogen atmosphere. The reaction mixture was allowed to warm up to room temperature and was kept stirring for 30 min. 20 mL of half-saturated aqueous ammonium chloride solution was added, followed by 100 mL of DCM. The organic layer was concentrated in vacuo on silica gel and purified by flash chromatography ($SiO_2$, 20-60% EtOAc/hexanes) to give 156 mg of the desired compound (98% yield). LC-MS $R_t$ (retention time): 2.48 min, MS: (ES) m/z 316 (M+H$^+$).

e) The bicyclic compound prepared in step d (156 mg, 0.49 mmol) was dissolved in a 4 N solution of hydrogen chloride in dioxane (2 mL). The resulting solution was heated to 60° C. for 1 h in a sealed vessel, followed by concentration in vacuo to give 146 mg of the carboxylic acid. LC-MS $R_t$ (retention time): 0.90 min, MS: (ES) m/z 260 (M+H$^+$).

f) Methanesulfonyl chloride (67 mg, 0.580 mmol) was added dropwise to a solution of the carboxylic acid prepared in step e above (75 mg, 0.290 mmol) and N,N-diisopropylethylamine (224 mg, 1.74 mmol) in THF (0.5 mL). The solution was aged at room temperature for 5 minutes, whereupon 3,5-bis(trifluoromethyl)aniline (133 mg, 0.58 mmol) was added. Stirring at 60° C. for 30 min, followed by the addition of another 33 mg of methanesulfonyl chloride, allowed the reaction to reach completion. 3 mL of water and 10 mL of DCM were added and the mixture was stirred vigorously for 5 min. The separated organic phase was concentrated in vacuo on silica gel and purified by flash chromatography ($SiO_2$, 30-80% EtOAc/hexanes) to give an off-white residue, which was recrystallized from a mixture of hot ethyl acetate and hexanes to give 57 mg of the desired compound (42% yield) as colorless crystals. $^1$H NMR (400 MHz, DMSO-$d_6$) δ 2.03-2.14 (m, 1H), 2.13 (s, 3H), 2.28 (s, 3H), 2.47-2.59 (m, 2H), 2.75-2.86 (m, 1H), 3.43-3.51 (m, 1H), 3.72 (d, J=10.4, 1H), 3.88 (d, J=10.4, 1H), 7.08-7.19 (m, 3H), 7.79 (s, 1H), 8.36 (s, 2H), 10.33 (s, 1H). LC-MS: $R_t$ (retention time)=2.74 min, MS: (ES) m/z 471 (M+H$^+$).

Example 38

Synthesis of 2-(2,6-Dimethyl-phenyl)-1-oxo-octahydro-isoindole-3a-carboxylic acid (3,5-bis-trifluoromethyl-phenyl)-amide

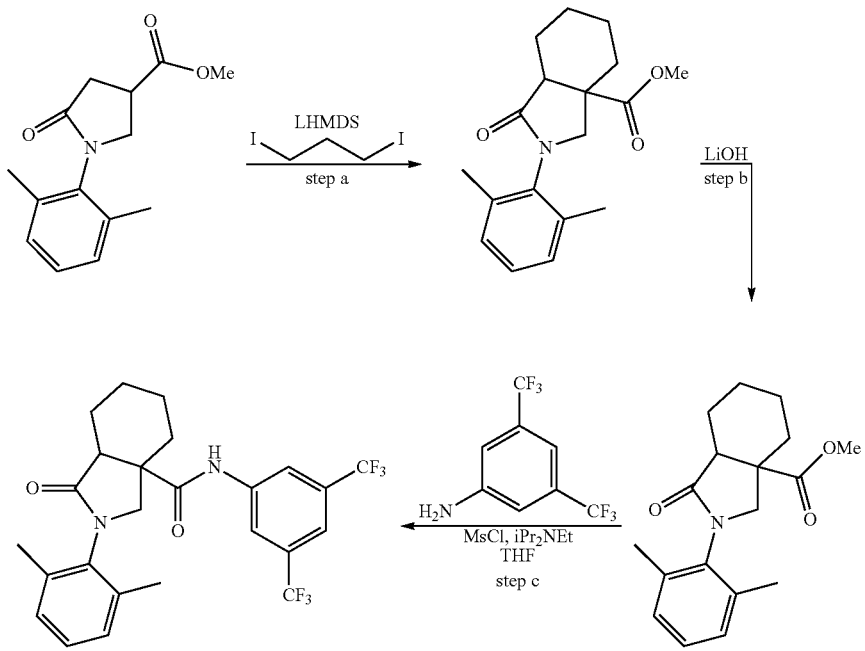

a) Lithium bis(trimethylsilyl)amide (1.0 M in THF, 3.8 mL, 2.4 mmol) was added to a solution of 1-(2,6-dimethyl-phenyl)-5-oxo-pyrrolidine-3-carboxylic acid methyl ester (0.4 g, 1.6 mmol) in THF (16 mL) in a reaction flask at −50° C. and stirred for 5 min. The reaction was then warmed to 0° C., and addition of 1,4-diiodobutane (0.79 g, 2.6 mmol) was followed. The reaction was warmed to room temperature and stirred for 1 h. The reaction quenched saturated $NH_4Cl$. The layers were separated and the aqueous layer was extracted with EtOAc (3×). The combined organic layers were dried ($MgSO_4$) and concentrated under reduced pressure. The residue was purified by flash chromatography ($SiO_2$, 0-50% hexanes/EtOAc) to give the desired compound in 63% yield (0.3 g).

b) Lithium hydroxide (1.0 M in $H_2O$, 10 mL, 10 mmol) was added to a solution of the ester from step a (0.3 g, 1.0 mmol) in MeOH (5 ml). The resulting solution was heated at 75° C. for 2 h. The solution was concentrated under reduced pressure to give 1/4 of the original volume and 6 M aqueous HCl (~0.5 mL) was added drop wise to adjust the pH to about 4. The aqueous layer was extracted with EtOAc (3×). The combined organic layers were dried ($MgSO_4$) and concentrated under reduced pressure to give the crude product (0.28 g, 100%). LC-MS: $R_t$ (retention time): 1.76 min, MS: (ES) m/z 288.3 (M+H$^+$).

c) Methanesulfonic acid (0.14 g, 1.2 mmol) and $iPr_2NEt$ (0.28 mL, 2.2 mmol) were added to a solution of the acid from step b (0.28 g, 1.0 mmol) in THF (4.7 ml) at room temperature. The resulting mixture was stirred at room temperature for 5 min, followed by addition of 3,5-bis(trifluoromethyl)aniline (0.06 g, 0.27 mmol). The reaction was heated at 75° C. until the reaction was completed (18 h). The mixture was concentrated under reduced pressure. Purification by flash chromatography ($SiO_2$, 0-75% hexanes/EtOAc) to give the desired product 75% yield (0.37 g). $^1$H NMR (400 MHz, DMSO-d$_6$): δ 10.12 (s, 1H), 8.35 (s, 2H), 7.78 (s, 1H), 7.14-7.07 (m, 3H), 3.74 (d, J=9.6 Hz, 1H), 3.55 (d, J=9.6, 1H), 3.09 (s, 1H), 2.32 (bd, J=13.6 Hz, 1H), 2.25 (s, 3H), 2.04 (s, 3H), 1.98-1.80 (m, 3H), 1.60-1.5 (m, 2H), 1.26-1.18 (m, 2H). LC-MS: $R_t$ (retention time): 2.94 min, MS: (ES) m/z 499.4 (M+H$^+$).

Example 39

Synthesis of 3-(2,6-dimethyl-phenyl)-4-oxo-3-azabicyclo[3.1.0]hexane-1-carboxylic acid (3,5-bis-trifluoromethyl-phenyl)-amide

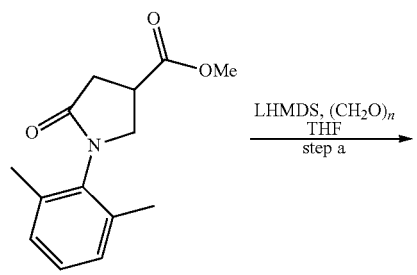

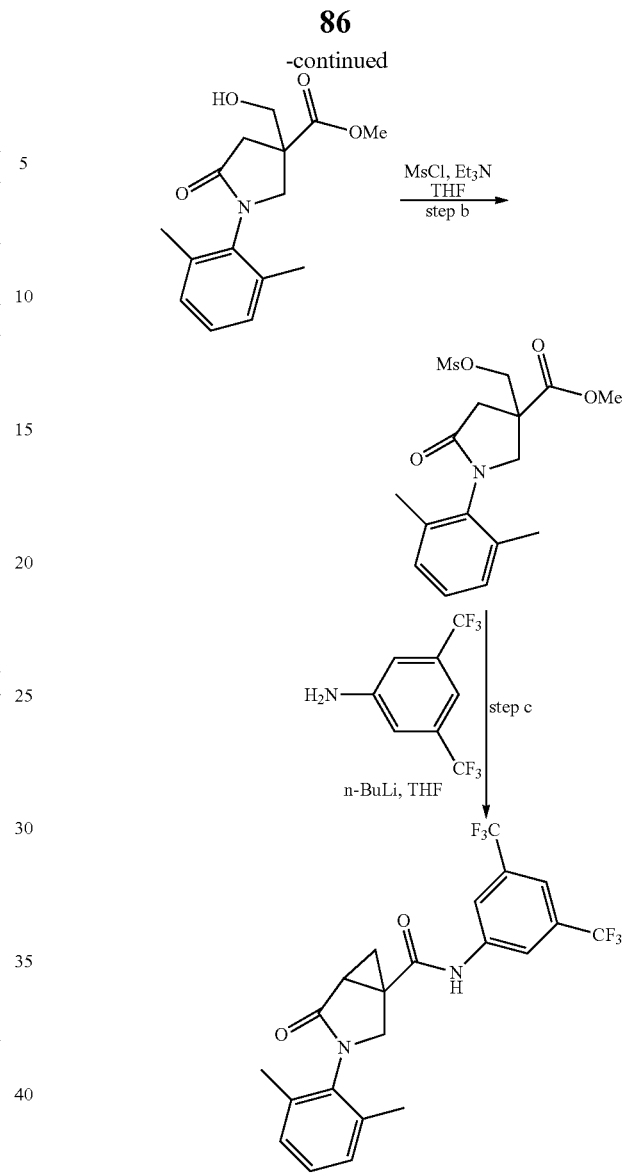

a) LHMDS (1 M solution in THF, 9.72 mL, 9.72 mmol) was added slowly to a cooled (−50° C.) solution of 1-(2,6-dimethyl-phenyl)-5-oxo-pyrrolidine-3-carboxylic acid methyl ester (2 g, 8.1 mmol) in THF (50 mL). Stirred at −50° C. for 5 min then warmed to 0° C. and stirred further for 5 min. After cooling back to −50° C., $(CH_2O)_n$ (1.2 g, 40.5 mmol) was added and the resulting reaction mixture was warmed to room temperature and stirred for 2 h. Saturated aqueous $NH_4Cl$ solution (25 mL) was added, extracted with EtOAc (3×75 mL). The combined organic layer was washed with water (100 mL), brine (100 mL), dried ($Na_2SO_4$) and evaporated. The residue was purified by automated flash chromatography ($SiO_2$, 20→50% EtOAc/hexanes) to give 1-(2,6-dimethyl-phenyl)-3-hydroxymethyl-5-oxo-pyrrolidine-3-carboxylic acid methyl ester (762 mg, 34% yield). LC-MS: $R_t$ (retention time): 0.9 min, MS: (ES) m/z 278.1 (M+H$^+$).

b) MsCl (105 μL, 1.35 mmol) was added to a cooled (0° C.) solution of 1-(2,6-dimethyl-phenyl)-3-hydroxymethyl-5-oxo-pyrrolidine-3-carboxylic acid methyl ester (prepared from step a, 250 mg, 0.9 mmol) and Et$_3$N (375 μL, 2.7 mmol)

in THF (5 mL). The resulting reaction mixture was stirred overnight at room temperature. Water (10 mL) was added and extracted with EtOAc (3×25 mL). The combined organic layer was washed with water (50 mL), brine (50 mL), dried (Na$_2$SO$_4$) and evaporated. The obtained crude product 1-(2,6-dimethyl-phenyl)-3-methanesulfonyloxymethyl-5-oxo-pyrrolidine-3-carboxylic acid methyl ester was used as such for the next step. LC-MS: R$_t$ (retention time): 1.73 min, MS: (ES) m/z 356.3 (M+H$^+$).

c) n-BuLi (2.5 M solution in hexanes, 560 µL, 1.39 mmol) was added to a solution of 3,5-bis-trifluoromethylaniline (216.5 µL, 0.545 mmol) in THF (3 mL) at room temperature. The resulting dark brown colored solution was stirred for 10 min at room temperature. A solution of 1-(2,6-dimethyl-phenyl)-3-methanesulfonyloxymethyl-5-oxo-pyrrolidine-3-carboxylic acid methyl ester (prepared from step b, 165 mg, 0.465 mmol) in THF (2 mL) was added and stirred for 2 h at 75° C. The reaction mixture was then purified by preparative HPLC (15→85% gradient of MeCN—H$_2$O with 0.1% TFA). The pure fractions were lyophilized to afford 3-(2,6-dimethyl-phenyl)-4-oxo-3-aza-bicyclo[3.1.0]hexane-1-carboxylic acid (3,5-bis-trifluoromethyl-phenyl)-amide (22 mg, 10% yield). LC-MS: R, (retention time): 2.98 min, MS: (ES) m/z 457.2 (M+H$^+$). $^1$H NMR (400 MHz, DMSO-d$_6$) δ 9.88 (s, 1H), 8.32 (s, 2H), 7.78 (s, 1H), 7.02-7.18 (m, 3H), 4.18 (d, 1H, J=9.7 Hz), 3.68 (d, 1H, J=9.7 Hz), 2.68-2.75 (m, 1H), 2.18 (s, 3H), 2.08-2.12 (m, 1H), 2.05 (s, 3H), 1.45 (t, 1H, J=3.9 Hz).

Example 40

Synthesis of N-(3,5-bis(trifluoromethyl)phenyl)-2-(2,6-dimethylphenyl)-1-oxooctahydrocyclopenta[c]pyrrole-3a-carboxamide a) To methyl 1-(2,6-dimethylphenyl)-5-oxopyrrolidine-3-carboxylate (1.5 g, 6.1 mmol) dissolved in 5 mL anhydrous THF and cooled to −40° C., lithium bis(trimethylsily)amide (1.0 M in THF, 6.1 mL, 6.1 mmol) was added with a syringe. After stirring for 10 min, the bath was replaced with a 0° C. bath and stirring continued for another 10 min. The reaction mixture was then cooled to −40° C. and another 6.1 mL of lithium bis(trimethylsily)amide solution (6.1 mmol) was added. After stirring for 10 min at −40° C., the reaction mixture was allowed to gradually warm to room temperature, quenched with saturated ammonium chloride solution (15 ml) and the crude product was extracted with ether. The combined organic layer was dried over anhydrous Na$_2$SO$_4$, the solvent was evaporated and the residue purified by flash chromatography (SiO$_2$, 10-100% EtOAc/hexanes) to yield 920 mg of methyl 2-(2,6-dimethylphenyl)-1-oxooctahydro-cyclopenta[c]pyrrole-3a-carboxylate (32% yield). LC-MS R$_t$ (retention time): 2.12 min, MS: (ES) m/z 288 (M+H$^+$).

b) Methyl 2-(2,6-dimethylphenyl)-1-oxooctahydrocyclopenta[c]pyrrole-3a-carboxylate (400 mg, 1.4 mmol) suspended in 5 mL of 1 M LiOH in 90% methanol was heated at 70° C. After cooling to room temperature, the reaction mixture was diluted with water, the pH adjusted to ~1 with concentrated HCl and the product was extracted twice with ethyl acetate (15 mL). The combined organic layer was dried over anhydrous Na$_2$SO$_4$ and the solvent was evaporated to yield 2-(2,6-dimethylphenyl)-1-oxooctahydrocyclopenta[c]pyrrole-3a-carboxylic acid (315 mg, 82% yield). LC-MS R$_t$ (retention time): 1.44 min, MS: (ES) m/z 274 (M+H$^+$).

c) To a solution of 2-(2,6-dimethylphenyl)-1-oxooctahydrocyclopenta[c]pyrrole-3a-carboxylic acid (86 mg, 0.3 mmol) and diisopropylethyl amine (104 µL, 0.6 mmol) in THF, methanesulfonyl chloride (32 µL, 0.4 mmol) was added. The mixture was treated with 3,5-bis(trifluoromethyl)aniline (137 mg, 0.6 mmol) and heated at 75° C. for 3 h. After evaporating the solvent, the crude product was applied on C$_{18}$ preparative HPLC column and eluted with acetonitrile/water solvent system (5-80% acetonitrile gradient with 0.1% TFA). After neutralization and solvent evaporation of the combined product containing fractions, 80 mg of N-(3,5-bis(trifluorom-

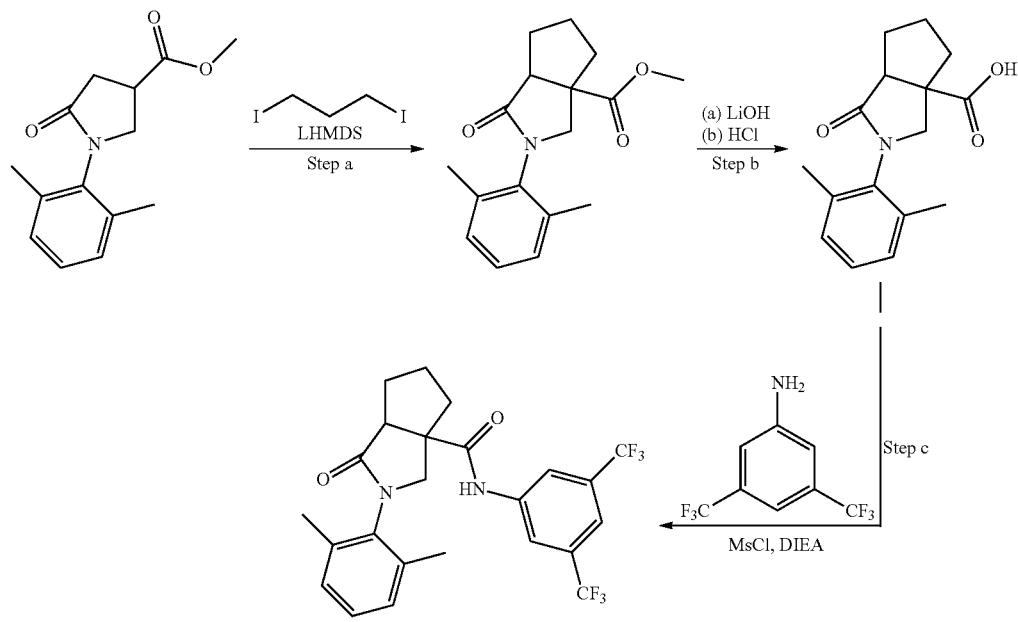

ethyl)phenyl)-2-(2,6-dimethylphenyl)-1-oxooctahydrocyclopenta[c]pyrrole-3a-carboxamide was obtained (53% yield). ¹H NMR (400 MHz, CDCl₃) δ 1.72-1.84 (m, 1H), 1.94-2.04 (m, 1H), 2.09 (s, 3H), 2.18 (s, 3H), 2.24-2.40 (m, 4H), 3.43 (d, 1H, J=11 Hz), 3.52-3.58 (m, 1H, 4.06 (d, 1H, J=11 Hz), 7.00-7.17 (m, 3H), 7.61 (s, 1H) 8.13 (s, 2H), 8.61 (s, 1H). LC-MS: R$_t$ (retention time)=2.99 min, MS: (ES) m/z 485 (M+H⁺).

Biological Example 1

To demonstrate that the compounds described above are useful modulators for chemokine binding to ChemR23, the compounds were screened in vitro to determine their ability to displace chemerin from the ChemR23 receptor at multiple concentrations. The compounds were combined with cells expressing the ChemR23 receptor (e.g., primary human dendritic cells or cells transfected to express ChemR23) in the presence of the ¹²⁵I-labeled chemerin as detailed in *Determination of IC$_{50}$ values, Reagents and Cells* (see below). The ability of the compounds to displace the labeled chemerin from the ChemR23 receptor sites at multiple concentrations was then determined with the screening process.

Compounds that were deemed effective modulators were able to displace at least 50% of the chemerin from the ChemR23 receptor at concentrations at or below 6 micromolar (μM) but >300 nM (+); and more preferably at concentrations from >30 nM to ≤300 nM (++). At present, especially preferred compounds can displace at least 50% of the chemerin from the ChemR23 receptor at concentrations at or below 30 nM (+++). Exemplary compounds that met these criteria are reproduced in FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W, 1X, 1Y, 1Z, 1AA, 1BB, 1CC, 1DD, 1EE and 1FF. All compounds were prepared as described in the Examples above, or by related methods substituting readily available starting materials.

1. Determination of IC$_{50}$ Values.
Reagents and Cells.

¹²⁵I-labeled chemerin was custom produced by PerkinElmer Life Sciences, Inc. (Boston, Mass.). The BaF3 (murine pro-B cell) cell line was obtained from the American Type Culture Collection (ATCC, Manassas, Va.) and was cultured in DMEM (Mediatech, Herndon, Va.) supplemented with 10% fetal bovine serum (FBS) (HyClone Logan, Utah) at 37° C. in a humidified incubator at a 5% CO₂/air mixture. ChemR23 transfected BaF3 cells were produced as described below. The complete coding sequence of the gene encoding ChemR23 (a.k.a. CMKLR1, DEZ), was isolated from primary macrophages using μMACs mRNA isolation kit (Miltenyi Biotec, Auburn, Calif.). DNA contamination was removed by DNase digestion via RNeasy columns (Qiagen, Inc., Valencia, Calif.) and cDNA was generated using GeneAmp RNA PCR Core Kit (Applied Biosystems, Foster City, Calif.). PCR of cDNA samples was performed using Taq PCR Master Mix kit (Qiagen, Inc.). The open reading frame was cloned into pcDNA3.1 (Invitrogen, CA (using standard techniques (Molecular Cloning: A Laboratory Manual, Sambrook and Maniatis) and transfected into BaF3 cells. Transfected cells were selected for using G418 at 800 ug/ml and optimal clones isolated by fluorescence activated sorting of antibody (R&D Systems) labeled cells.

Binding Analysis.

Target compounds were tested to determine their ability to bind with ChemR23 sites on BaF3 ChemR23 transfected cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines*, J. Biol. Chem. 1999 Jul. 30; 274(31): 21569-74 and Gosling J, et al., *Cutting edge: identification of a novel chemokine receptor that binds dendritic cell-and T cell-active chemokines including ELC, SLC, and TECK.*, J. Immunol. 2000 Mar. 15; 164(6):2851-6 was used.

In these assays, BaF3 ChemR23 transfected cells were interrogated with the target compounds and the ability of these compounds to displace ¹²⁵I radiolabeled chemerin was assessed using the protocol described in Dairaghi and Gosling. The target compounds were added to the plate to the indicated concentration and were then incubated with cells followed by the addition of radiolabeled ligand (¹²⁵I chemerin) for 3 hr at 4° C. in the following binding medium (25 mM HEPES, 140 mM NaCl, 1 mM CaCl₂, 5 mM MgCl₂ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM CaCl₂, 5 mM MgCl₂, adjusted to pH 7.1). Scintillant (MicroScint 10, Packard) was added to the wells, and the filters were counted in a Packard Topcount scintillation counter. Data were analyzed and plotted using GraphPad Prism (GraphPad Software).

Transendothelial Migration Assay:

The compounds of the invention were further assessed for their ability to inhibit migration of cells in a transendothelial migration assay. In this assay, the ability of a cell to migrate through a layer of endothelial cells towards a chemokine source is analyzed. In one example of this assay 100,000 human umbillic vein endothelial cells (HUVECs, available from Lonza) were plated into the upper chamber of a transwell culture dish with a 5 uM filter pore size (Corning Costar). Medium was added and plates placed in an incubator overnight with 5% CO₂ at 37° C. After HUVECs adhered to the filter overnight forming a monolayer, medium containing chemokine (eg chemerin, final concentration 10 nM) was added to the lower chamber. Then 500,000 primary human plasmacytoid dendritic cells (pDC) isolated from whole blood or primary monocyte derived dendritic cells (differentiatied from primary human PBMC) were added to the upper chamber in the presence or absence of the test compound, and plates were returned to the incubator for 3 hours to overnight. Various concentrations of compound were added to different wells to create a dose response. At the end of this incubation the upper chamber was removed and the cells in the lower chamber were quantified. The cells were quantified by labeling with the fluorescent dye Cyquant® (Invitrogen, CA) and fluorescence quantified on an appropriate plate reader. Data was analyzed and plotted using GraphPad Prism (GraphPad Software). The efficacy of the compound is measured as its ability to inhibit the migration of these cells to the lower chamber.

Migration to Monocyte Derived Supernatants:

Selected compounds of the invention were further assessed for their ability to inhibit migration of cells to supernatants containing active chemerin, derived from mature human adipocytes. In this assay human pre-adipocytes (Zenbio, N.C.) were cultured in adipocyte differentiation medium (Zenbio, catalog #DM-2) and incubated for 7 days at 37° C. and 5% CO₂. After 7 days, differentiation medium was replaced with fresh Adipocyte Medium (Zenbio, catalog #AM-1). After two weeks of differentiation, mature adipocytes were stimulated with 10 ng/ml TNFa for 72 hours. Supernatant was then collected and added to the bottom chamber of 96 well migration plates (Neuroprobe, MD), and 100,000 BAF3-ChemR23 transfectant cells added to the upper chamber. Plates were incubated for 2 hours at 37° C. Various concentrations of compound were added to different wells to create a dose response. At the end of this incubation the upper chamber was removed and the cells in the lower chamber were quantified. The cells were quantified by labeling with the fluorescent dye Cyquant® (Invitrogen, CA) and fluorescence quantified on an appropriate plate reader. Data was analyzed and plotted using GraphPad Prism (GraphPad Software). The efficacy of the compound is measured as its ability to inhibit the migration of these cells to the lower chamber.

In Vivo Efficacy a) Rodent Model of Experimental Autoimmune Encephalomyelitis

An experimental autoimmune encephalomyelitis (EAE) study can be conducted to evaluate the effects of a compound of interest on EAE induced paralysis. Rodent EAE is an experimental model of multiple sclerosis (MS) that has been widely used for preclinical testing of numerous agents for the treatment of relapsing remitting and progressive MS. The hallmarks of this model are reliable onset and progression of robust, easily measurable paralysis of tail and limbs, neuronal inflammation, marked demyelination in response to neural antigens.

Female rodents are anesthetized with isoflurane and injected with Freund's Incomplete Adjuvant containing 1 mg/mL neuronal antigen (e.g. myelin basic protein, myelin oligodendrocyte glycoprotein, proteolipid protein) and 4 mg/mL *mycobacterium tuberculosis* at two sites on the back on day 0 of this study. A compound of interest is dosed daily in a sub-cutaneous, intra-peritoneally, or oral manner from day 0 till end of study at an efficacious dose. Daily observations of degree of paralysis are taken as measures of efficacy.

(b) Evaluation of a Compound of Interest in a Mouse Model of Diet Induced Obese Insulin Resistance.

In the insulin resistance studies, C57 B1/6 derived male mice (24±2 g) are used. Mice are placed on a high fat diet (60% kcal form fat) or control diet (10% kcal from fat) for a period of 12-24 weeks. After 12-24 weeks on diet fasting blood glucose levels are measured to determine degree of insulin resistance. Animals are then randomized into treatment groups. A test compound or vehicle is administered daily via sub-cutaneous, intra-peritoneally, or oral route at an efficacious dose until the end of study. Measurements taken include fasting blood glucose, fasting insulin, free fatty acids, total cholesterol, response to systemic glucose challenge, response to systemic insulin challenge. Unpaired Student's t test may be applied for comparison between the treated and vehicle groups at each measurement time point. Differences are considered of statistical significance at P<0.05 level.

(c) Evaluation of a Compound of Interest in an Animal Model of Dermal Inflammation.

In the dermal inflammation studies several species may be used such as but not limited to non-human primate, mouse, rat, rabbit, etc. Dermal irritants are injected into the skin or applied topically. Wheal and flare reactions are measured as well as punch biopsies taken from affected areas. Immunohistochemistry and immunoflourescence are used to define degrees of inflammation. A test compound or vehicle is administered daily via sub-cutaneous, intra-peritoneally, or oral route at an efficacious dose until the end of study Unpaired Student's t test may be applied for comparison between the treated and vehicle groups at each measurement time point. Differences are considered of statistical significance at P<0.05 level.

(d) Results of Animal Dermal Inflammation Evaluation.

Compounds of the invention were assessed in the murine imiquimod model of dermal inflammation. Briefly, 8-10 week old female BALB/c mice were treated topically daily from day 0 with 5% imiquimod cream applied to the shaved backs and ears. Also from day 0 mice were treated orally daily with 3 mg/kg compound or the corn oil:Solutol (70:30) vehicle. From days three through ten skin thickness and ear thickness were assessed using caliper measurements. Animals treated with compound had significantly reduced ear swelling and skin thickness compared to the vehicle treated controls, indicating a compound mediated decrease in imiquimod induced inflammation.

What is claimed is:

1. A compound having the formula:

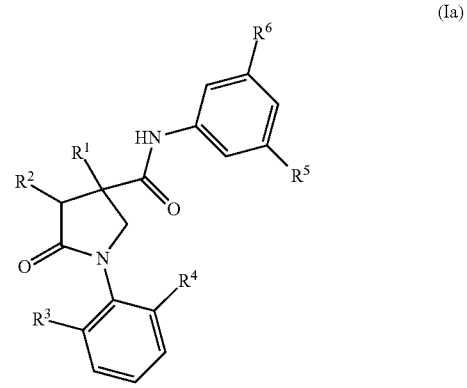

(Ia)

or a pharmaceutically acceptable salt, stereoisomer, rotamer or isotopically enriched variants thereof, wherein $R^1$ is a member selected from the group consisting of hydroxyl, $C_{1-8}$ alkyl, $C_{2-8}$ alkenyl, $C_{1-8}$ alkoxy, $C_{1-8}$ alkoxy-$C_{1-8}$ alkyl, $C_{1-8}$ haloalkyl, $C_{1-8}$ hydroxyalkyl, $C_{3-8}$ cycloalkyl, $C_{3-8}$ cycloheteroalkyl, $C_{3-8}$ cycloalkyl-$C_{1-3}$ alkyl, $C_{3-8}$ cycloheteroalkyl-$C_{1-3}$ alkyl, heteroaryl, heteroaryl-$C_{1-4}$ alkyl, aryloxy$C_{1-4}$ alkyl, aryl-$C_{1-2}$ alkoxy-$C_{1-4}$ alkyl, —NR$^a$R$^b$, and R$^a$R$^b$N—$C_{1-4}$ alkyl wherein R$^a$ and R$^b$ are each independently selected from the group consisting of H, $C_{1-8}$ alkyl, $C_{3-8}$ cycloalkyl, $C_{1-8}$ haloalkyl, $C_{3-8}$ cycloheteroalkyl, $C_{1-8}$ alkoxy-$C_{1-8}$ alkyl, mono- or di-($C_{1-4}$ alkyl)amino-$C_{1-4}$ alkyl, and $C_{1-8}$ hydroxyalkyl, or R$^a$ and R$^b$ are combined with the nitrogen to which each is attached to form a 4- to 7-membered ring optionally having an additional O or N as a ring member and optionally substituted with from 1 to 4 substitutents selected from the group consisting of hydroxy, halogen, $C_{1-4}$ alkyl and $C_{1-4}$ haloalkyl;

$R^2$ is a member selected from the group consisting of H, $C_{1-8}$ alkyl, and $C_{2-8}$ alkenyl;

or optionally, $R^1$ and $R^2$ are combined to form a four- to six-membered ring fused to the pyrrolidinone ring and having at least one ring vertex heteroatom selected from the group consisting of O, S and N;

$R^3$ is a member selected from the group consisting of H, halogen, $C_{1-4}$ alkyl, $C_{2-6}$ alkenyl, $C_{3-6}$ cycloalkyl, $C_{3-8}$ cycloheteroalkyl, $C_{3-8}$ cycloalkyl-$C_{1-3}$ alkyl and $C_{3-8}$ cycloheteroalkyl-$C_{1-3}$ alkyl;

$R^4$ is a member selected from the group consisting of H, halogen, $C_{1-4}$ alkyl, $C_{2-6}$ alkenyl, $C_{1-4}$ hydroxyalkyl, $C_{1-4}$ alkoxy, $C_{1-4}$ alkoxy-$C_{1-4}$ alkyl, $C_{1-6}$ haloalkyl, and mono- or di-($C_{1-4}$ alkyl)amino;

$R^5$ is a member selected from the group consisting of $CF_3$, halogen, cyano, $C_{1-4}$ alkyl, $C_{2-6}$ alkenyl, $C_{1-4}$ hydroxyalkyl, $C_{1-5}$ alkoxy, $C_{1-4}$ alkoxy-$C_{1-4}$ alkyl, $C_{1-4}$ alkoxy-$C_{1-4}$ alkoxy, $C_{3-8}$ cycloalkyl, $C_{3-8}$ cycloalkyloxy, $C_{3-8}$ cycloheteroalkyl, $C_{3-8}$ cycloheteroalkyl-$C_{1-3}$ alkyl and mono- or di-($C_{1-4}$ alkyl)amino;

$R^6$ is a member selected from the group consisting of hydrogen, halogen, cyano, $C_{1-4}$ alkyl, $C_{1-4}$ haloalkyl, $C_{2-6}$ alkenyl, $C_{1-4}$ hydroxyalkyl, $C_{1-5}$ alkoxy, $C_{1-4}$ alkoxy-$C_{1-4}$ alkyl, $C_{1-4}$ alkoxy-$C_{1-4}$ alkoxy, $C_{3-8}$ cycloalkyl, $C_{3-8}$ cycloalkyloxy, $C_{3-8}$ cycloheteroalkyl, $C_{3-8}$ cycloheteroalkyl-$C_{1-3}$ alkyl and mono- or di-($C_{1-4}$ alkyl)amino;

wherein alkyl, aryl and heteroaryl are unsubstituted forms of the indicated radical, except wherein any ring portions of $R^1$, $R^2$, $R^3$, $R^4$, $R^5$, and $R^6$, including the optional fused rings, are optionally substituted with from 1 to 3 substituents independently selected from the group consisting of halogen, $C_{1-4}$ alkyl, benzyl, oxo and $C_{1-6}$ alkoxycarbonyl, and any cycloalkyl and cycloheteroalkyl portions optionally have a double bond between ring vertices.

2. A compound of claim 1, wherein $R^6$ is $CF_3$.

3. A compound of claim 1, wherein $R^3$ is methyl.

4. A compound of claim 1, wherein $R^3$ is methyl, and $R^4$ is H or $C_{1-4}$ alkyl.

5. A compound of claim 1, wherein $R^2$ is H or $C_{1-8}$ alkyl, $R^3$ is methyl, and $R^4$ is H or $C_{1-4}$ alkyl.

6. A compound of claim 1, wherein $R^5$ is $CF_3$.

7. A compound of claim 1, wherein $R^3$ is methyl and $R^5$ is $CF_3$.

8. A compound of claim 1, having the formula:

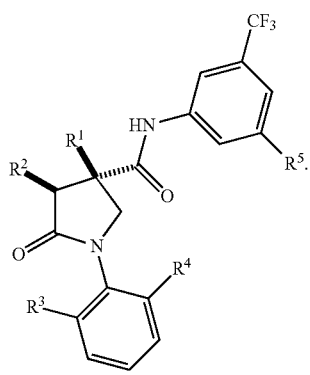

(Ib)

9. A compound of claim 8, wherein $R^1$ is selected from the group consisting of —$NR^aR^b$ and $R^aR^bN$—$C_{1-4}$ alkyl.

10. A compound of claim 9, wherein $R^1$ is $R^aR^bN$—$C_{1-4}$ alkyl.

11. A compound of claim 9, wherein $R^1$ is —$NR^aR^b$.

12. A compound of claim 8, wherein $R^3$ and $R^4$ are each methyl.

13. A compound of claim 12, wherein $R^5$ is selected from the group consisting of $CF_3$, CN and cyclopropyl.

14. A compound of claim 8, wherein $R^1$ is mono- or di-($C_{1-4}$ alkyl)amino-$C_{1-4}$ alkyl, and $R^3$ is methyl.

15. A compound of claim 14, wherein $R^1$ is di($C_{1-4}$ alkyl)aminomethyl.

16. A compound of claim 8, wherein $R^2$ and $R^3$ are each methyl.

17. A compound of claim 1, having the formula:

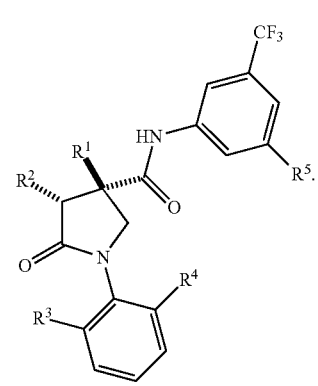

(Ic)

18. A compound of claim 17, wherein $R^2$ is H, and $R^3$ and $R^4$ are each methyl.

19. A compound of claim 18, wherein $R^5$ is $CF_3$.

20. A compound selected from the group consisting of:

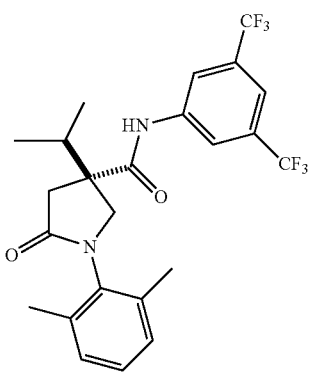

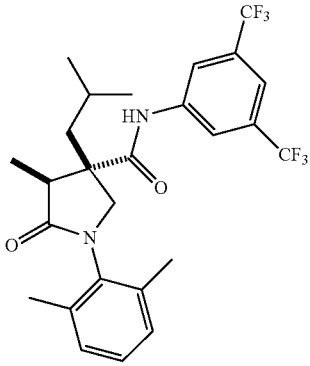

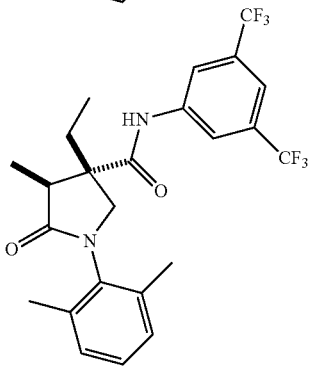

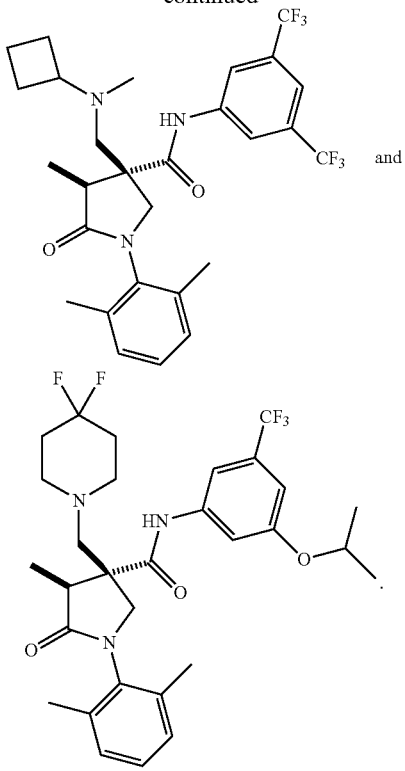

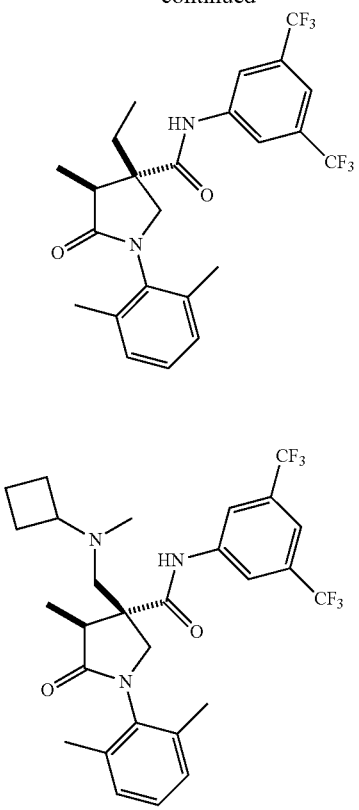

21. A pharmaceutical composition comprising a compound of claim 1 and a pharmaceutically acceptable excipient.

22. The pharmaceutical composition of claim 21, wherein the compound is selected from the group consisting of;

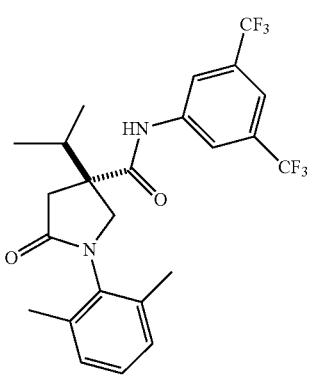

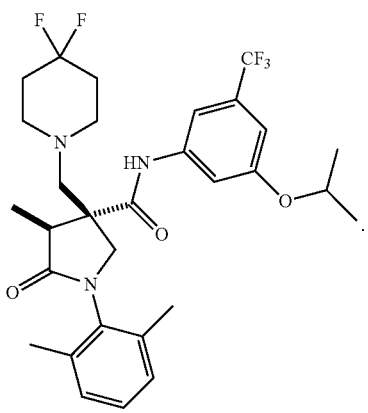

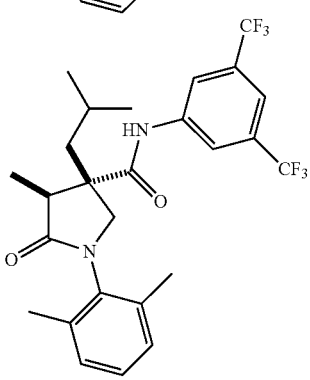

23. A method of treating an inflammatory condition in a mammal, said method comprising administering to said mammal a therapeutically effective amount of a compound of claim 1, for a period of time sufficient to treat said inflammatory condition.

24. The method of claim 23, wherein said mammal is a human.

25. The method of claim 23, wherein said inflammatory condition is selected from the group consisting of neural, skin or metabolic inflammatory conditions.

* * * * *